(12) United States Patent
Dougherty et al.

(10) Patent No.: US 9,795,374 B2
(45) Date of Patent: Oct. 24, 2017

(54) IMPLANT PLACEMENT SYSTEMS, DEVICES, AND METHODS

(71) Applicant: Tenjin LLC, Brazoria, TX (US)

(72) Inventors: Christopher P. Dougherty, Rogers, AR (US); Gary R. Heisler, Brazoria, TX (US); Robert A. Van Wyk, St. Pete Beach, FL (US)

(73) Assignee: Tenjin LLC, Brazoria, TX (US)

( * ) Notice: Subject to any disclaimer, the term of this patent is extended or adjusted under 35 U.S.C. 154(b) by 130 days.

(21) Appl. No.: 14/972,662

(22) Filed: Dec. 17, 2015

(65) Prior Publication Data

US 2016/0220242 A1 Aug. 4, 2016

Related U.S. Application Data

(63) Continuation of application No. 14/636,389, filed on Mar. 3, 2015, now Pat. No. 9,226,817.

(Continued)

(51) Int. Cl.
*A61B 17/04* (2006.01)
*A61F 2/08* (2006.01)
(Continued)

(52) U.S. Cl.
CPC .... *A61B 17/0401* (2013.01); *A61B 17/00234* (2013.01); *A61B 17/0485* (2013.01); *A61F 2/0805* (2013.01); *A61F 2/0811* (2013.01); *A61B 17/0482* (2013.01); *A61B 17/06061* (2013.01); *A61B 2017/00305* (2013.01); *A61B 2017/00309* (2013.01); *A61B 2017/00314* (2013.01); *A61B 2017/00353* (2013.01); *A61B 2017/00424* (2013.01); *A61B 2017/00477* (2013.01); *A61B 2017/044* (2013.01); *A61B 2017/0409* (2013.01); *A61B 2017/0412* (2013.01); *A61B 2017/0414* (2013.01); *A61B 2017/0445* (2013.01); *A61B 2017/0458* (2013.01); *A61B 2017/0464* (2013.01); *A61B 2017/0496* (2013.01);

(Continued)

(58) Field of Classification Search
CPC .......... A61B 17/0401; A61B 2017/044; A61B 2017/0445; A61B 2017/0409; A61F 2/0811; A61F 2002/0858
USPC .................................. 606/104, 148
See application file for complete search history.

(56) References Cited

U.S. PATENT DOCUMENTS 5,100,417 A 3/1992 Cerier
5,152,765 A 10/1992 Ross
(Continued)

OTHER PUBLICATIONS

Product Brochure for "SpeedBridge™ and SpeedFix™ Knotless Rotator Cuff Repair using the SwiveLock® C and FiberTape®: Surgical Technique", Arthrex, Inc., 2013.
(Continued)

*Primary Examiner* — Julian W Woo
(74) *Attorney, Agent, or Firm* — Chalin A. Smith; Smith Patent, LLC

(57) ABSTRACT

Described herein is a simplified placement system and method for a tissue graft anchor by which a surgeon may introduce one or more sutures into a hole in a boney tissue, apply tension to the sutures to advance a soft tissue graft to a desired location, and then advance the anchor into the bone while maintaining suture tension and without introducing spin to the suture.

8 Claims, 61 Drawing Sheets

Related U.S. Application Data

(60) Provisional application No. 61/966,744, filed on Mar. 3, 2014, provisional application No. 61/998,391, filed on Jun. 26, 2014, provisional application No. 61/998,766, filed on Jul. 7, 2014, provisional application No. 61/999,405, filed on Jul. 26, 2014.

(51) Int. Cl.
*A61B 17/00* (2006.01)
*A61B 17/06* (2006.01)

(52) U.S. Cl.
CPC ............ *A61F 2002/0841* (2013.01); *A61F 2002/0858* (2013.01); *A61F 2002/0888* (2013.01)

(56) References Cited

U.S. PATENT DOCUMENTS

| | | | |
|---|---|---|---|
| 5,217,486 A | 6/1993 | Rice | |
| 5,464,407 A * | 11/1995 | McGuire | A61B 17/15 606/104 |
| 5,584,860 A | 12/1996 | Goble | |
| 5,591,207 A * | 1/1997 | Coleman | A61B 17/0401 606/104 |
| 5,746,752 A * | 5/1998 | Burkhart | A61B 17/0469 606/139 |
| 5,827,291 A | 10/1998 | Fucci | |
| 5,948,000 A | 9/1999 | Larsen | |
| 6,402,759 B1 * | 6/2002 | Strong | A61B 17/068 606/104 |
| 6,544,281 B2 | 4/2003 | El Attrache et al. | |
| 6,641,597 B2 | 11/2003 | Dreyfuss | |
| 6,660,010 B2 * | 12/2003 | Gellman | A61B 17/0401 606/104 |
| 7,329,264 B2 | 2/2008 | Merves | |
| 8,435,264 B2 | 5/2013 | Sojka | |
| 8,758,367 B2 | 6/2014 | Philippon | |
| 8,814,905 B2 | 8/2014 | Sengun | |
| 8,858,596 B2 | 10/2014 | Robison | |
| 8,911,474 B2 * | 12/2014 | Howard | A61B 17/0401 606/104 |
| 9,095,331 B2 | 8/2015 | Hernandez | |
| 9,226,817 B2 | 1/2016 | Dougherty | |
| 9,370,351 B2 | 6/2016 | Sojka | |
| 2006/0100627 A1 | 5/2006 | Stone | |
| 2009/0306671 A1 | 12/2009 | McCormack | |
| 2009/0312795 A1 | 12/2009 | Barbieri | |
| 2014/0277128 A1 | 9/2014 | Moore | |

OTHER PUBLICATIONS

Product Brochure for "Healix Knotless™ Anchor", DePuy Mitek, Inc., 2012.
"Optimized Sports Medicine Solutions", Parcus Medical, LLC, 2013.
"ReelX STT™ Knotless Anchor System", Stryker® Corporation, 2010.
"PopLok 3.5 & 4.5 MM", ConMed Corporation, 2015.

* cited by examiner

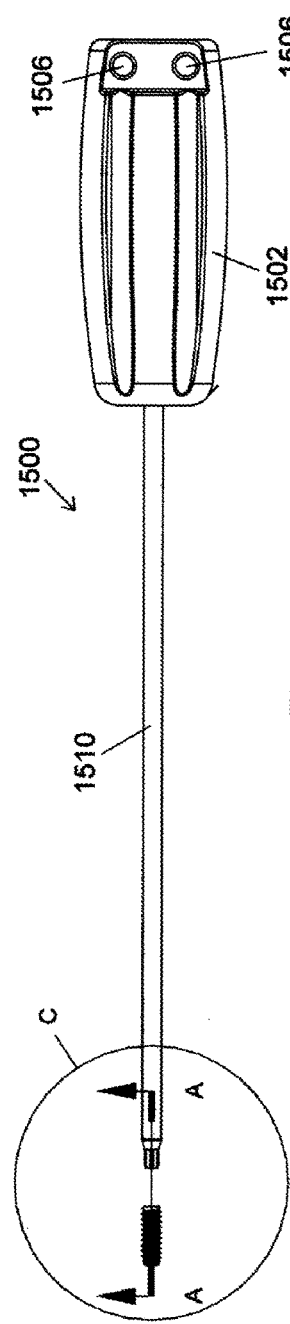
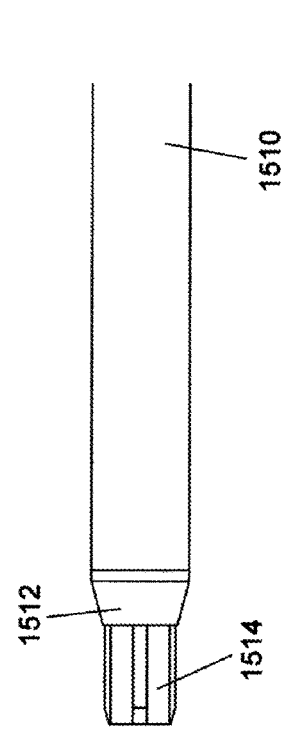
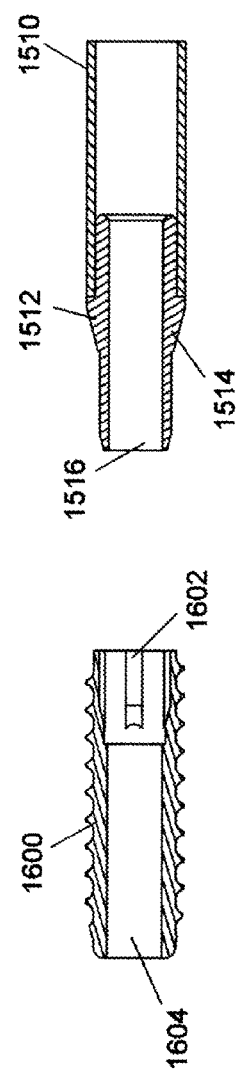
Fig. 1A
Fig. 1B
Fig. 1C

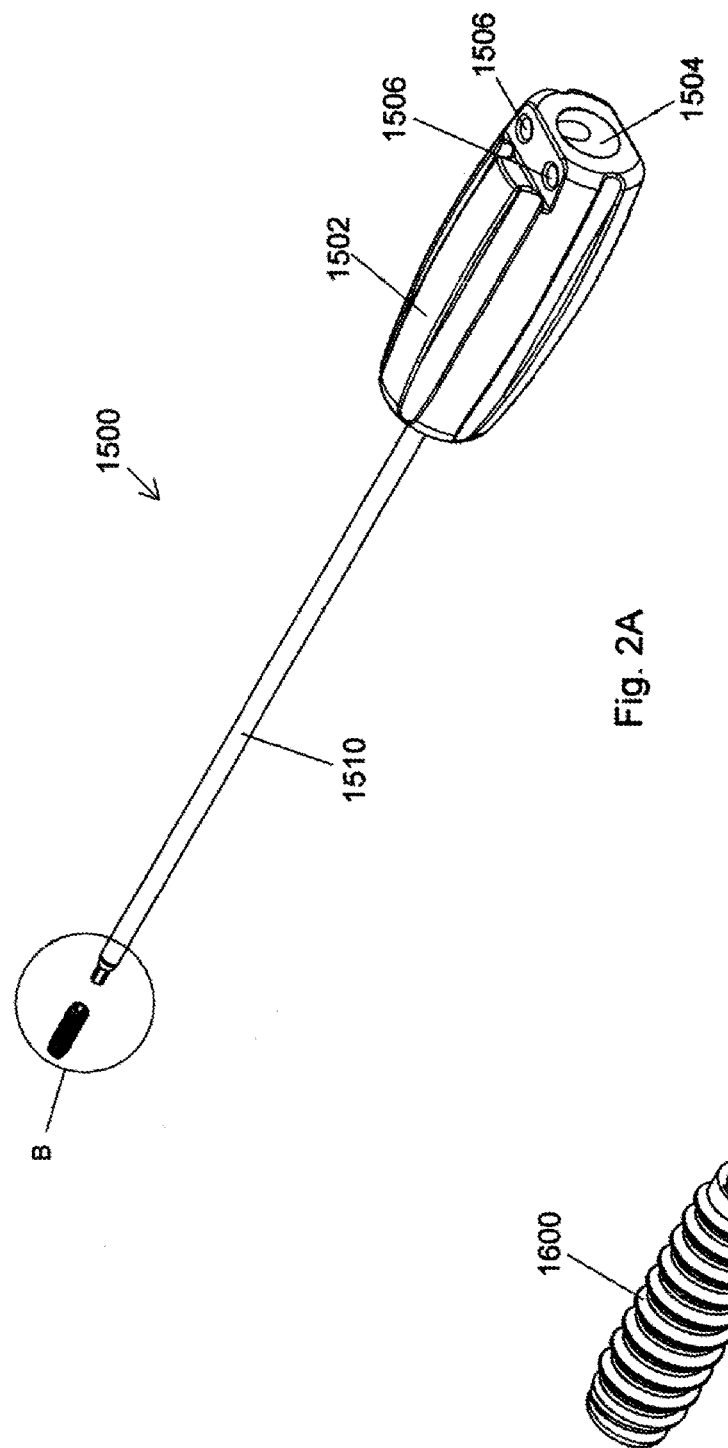
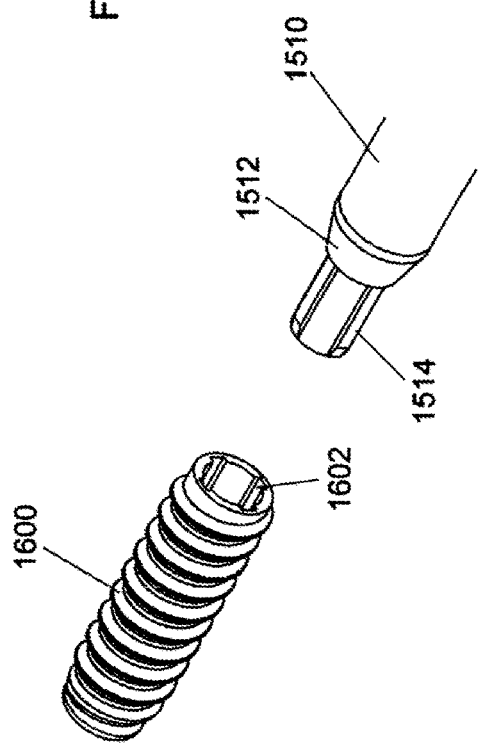
Fig. 2A
Fig. 2B

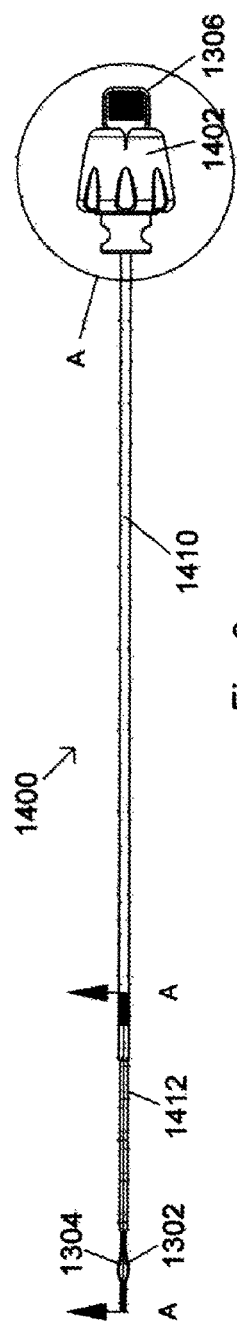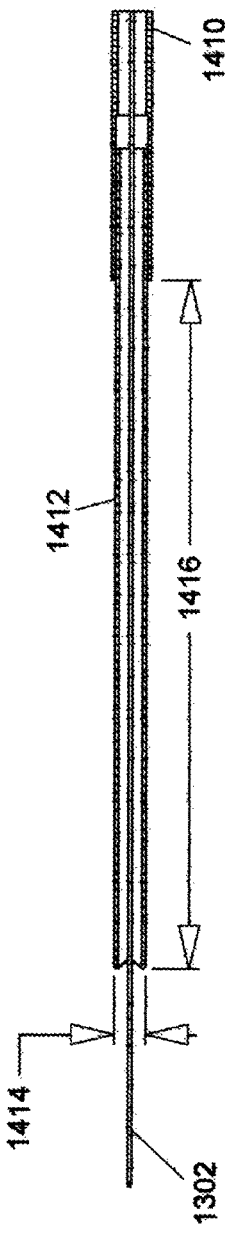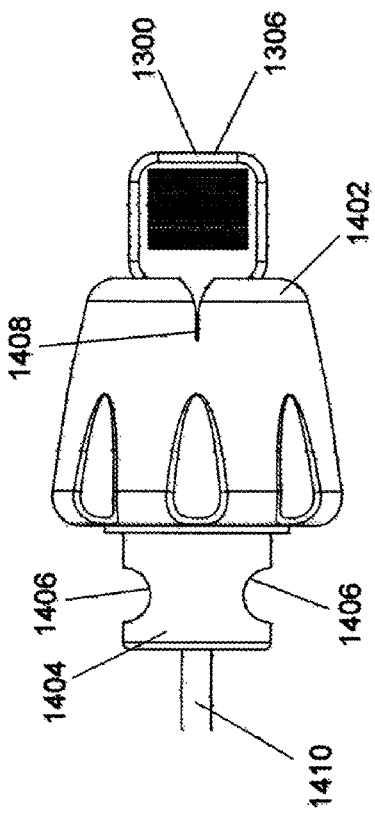
Fig. 3
Fig. 4
Fig. 5

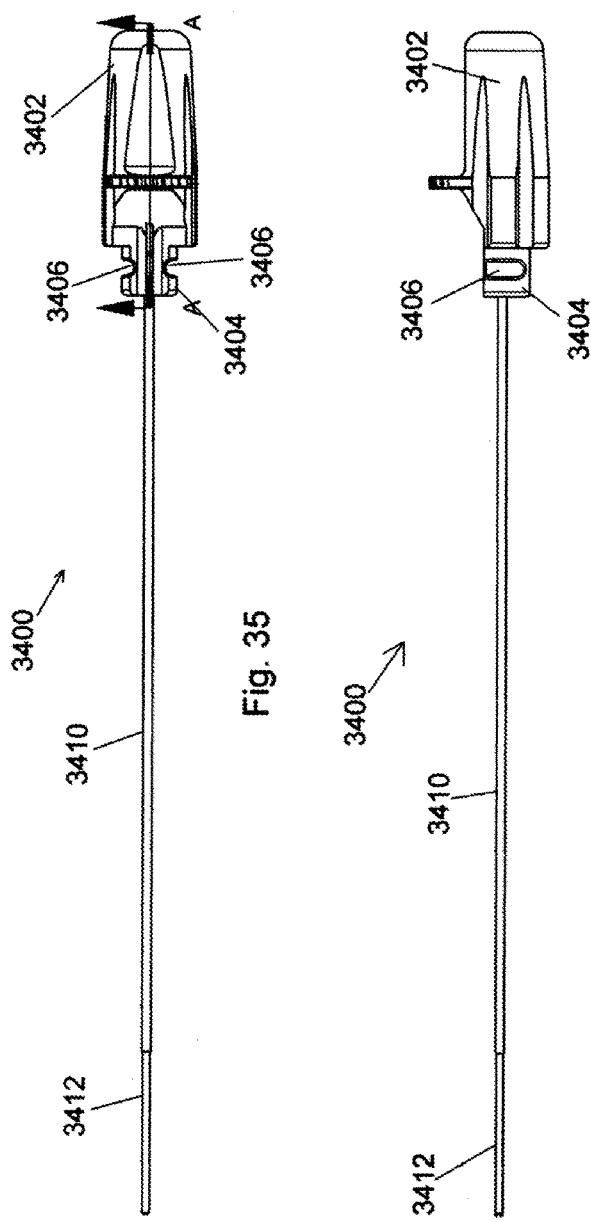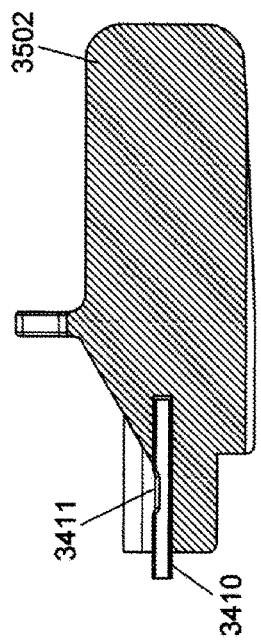

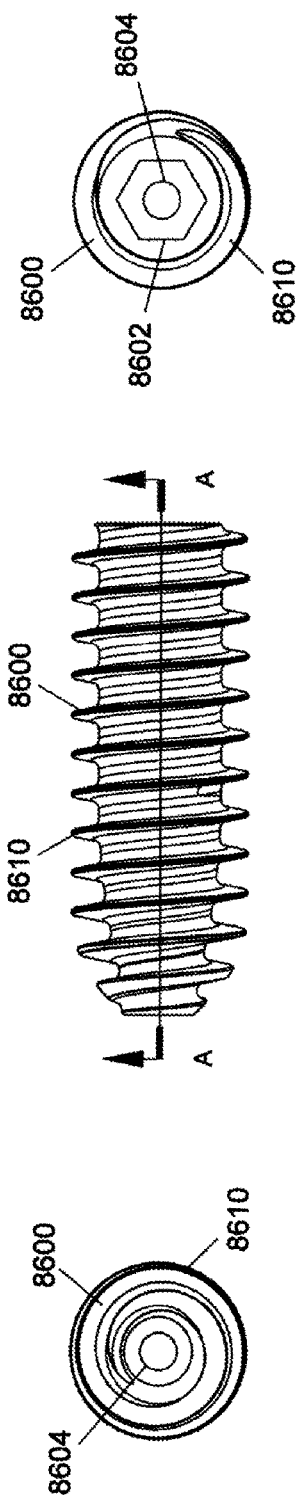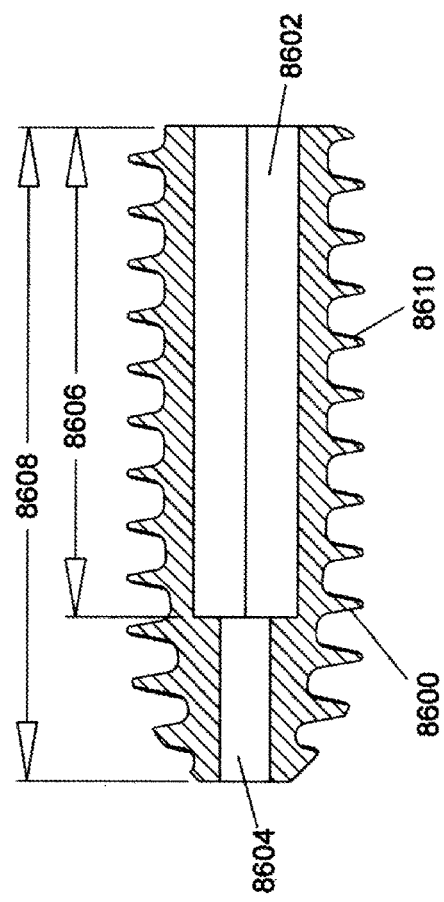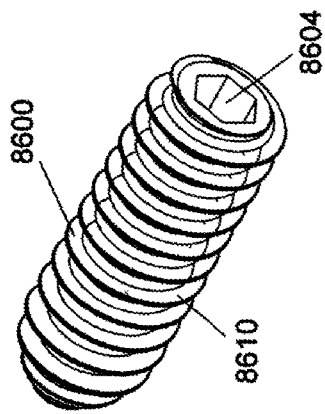

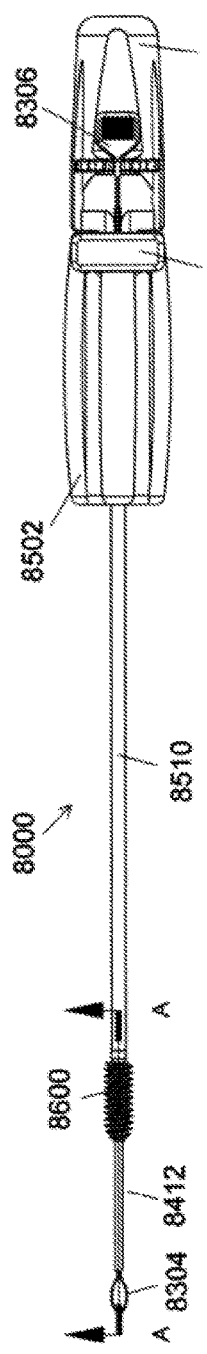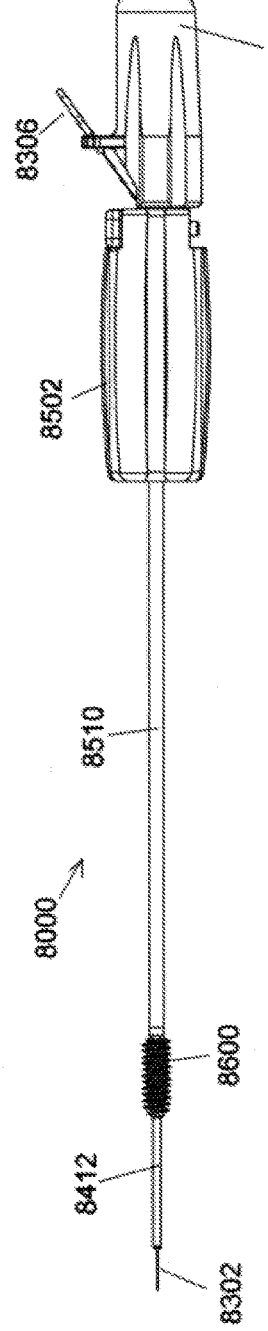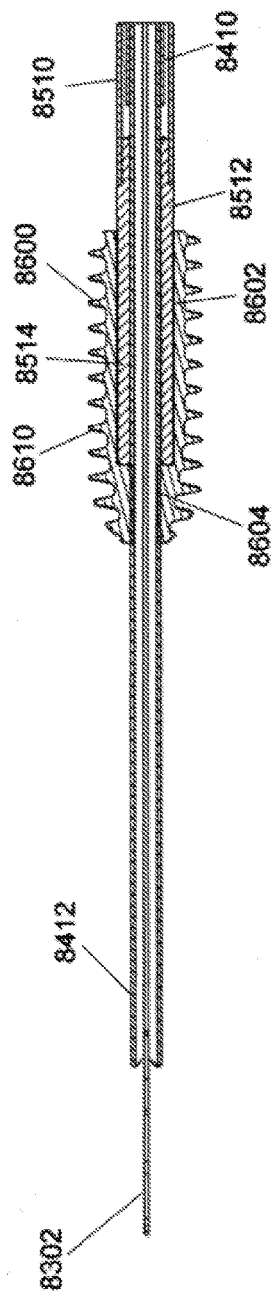

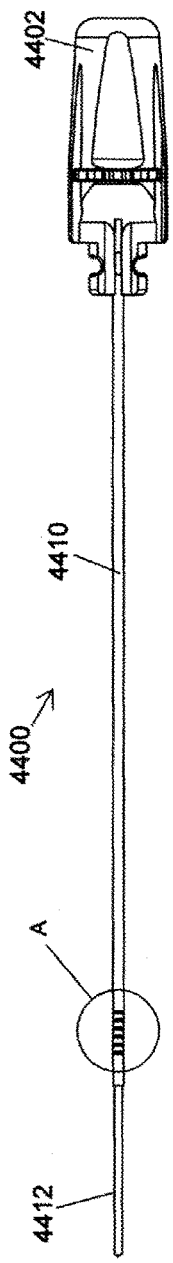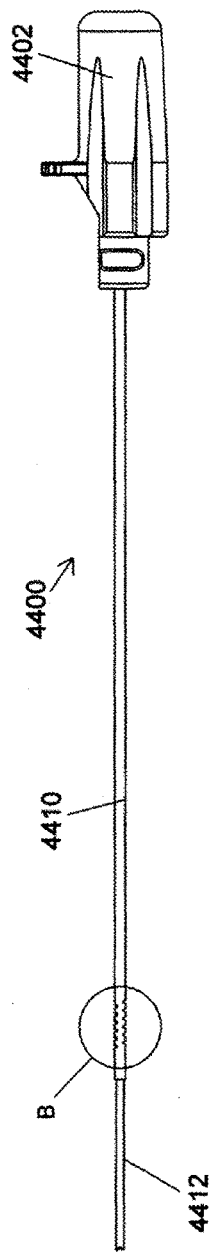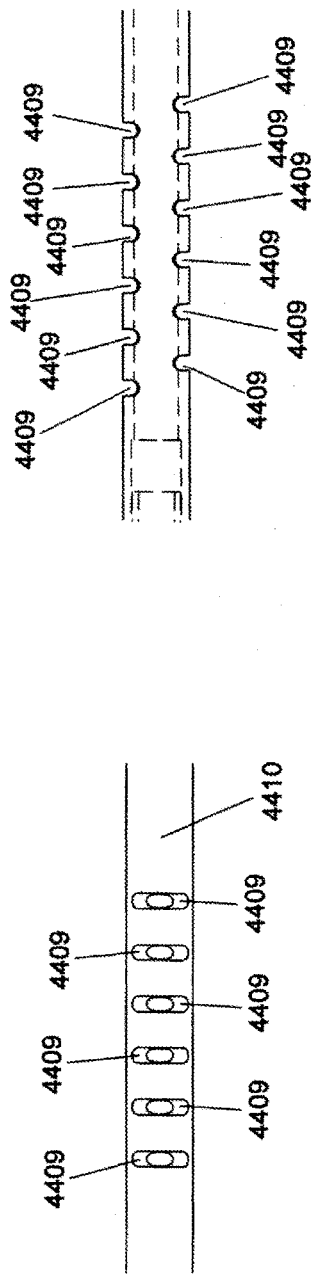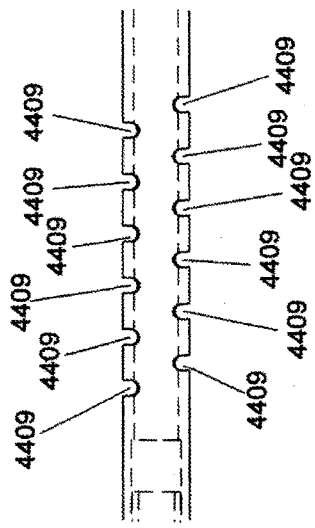
Fig. 61
Fig. 62
Fig. 63
Fig. 64

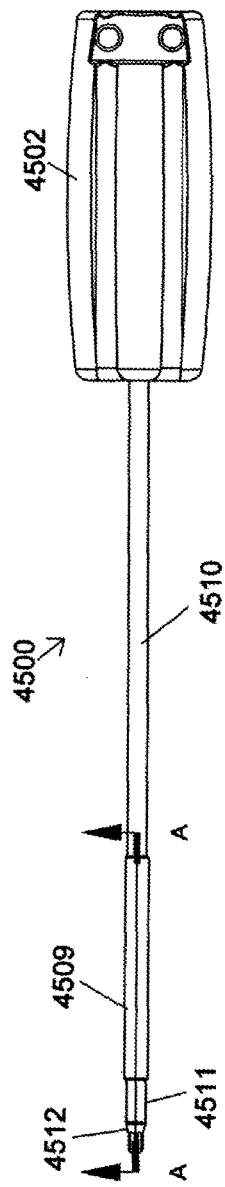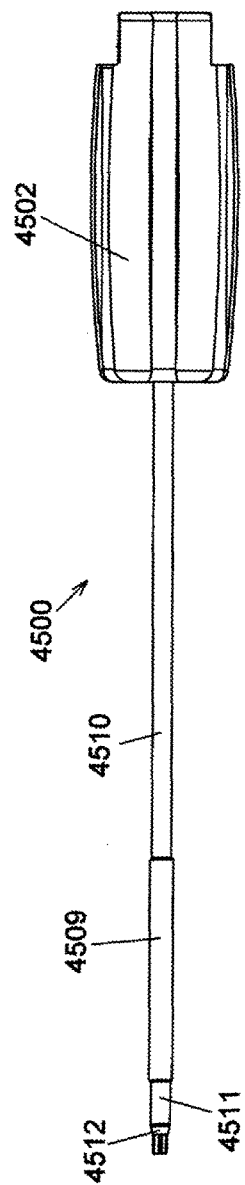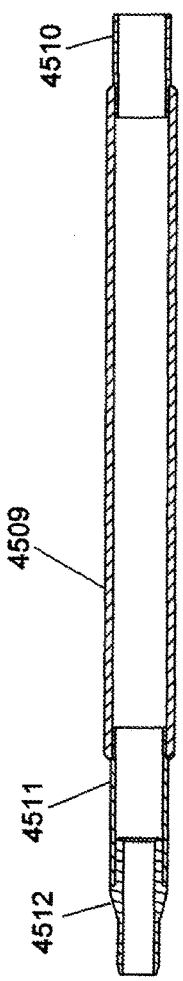

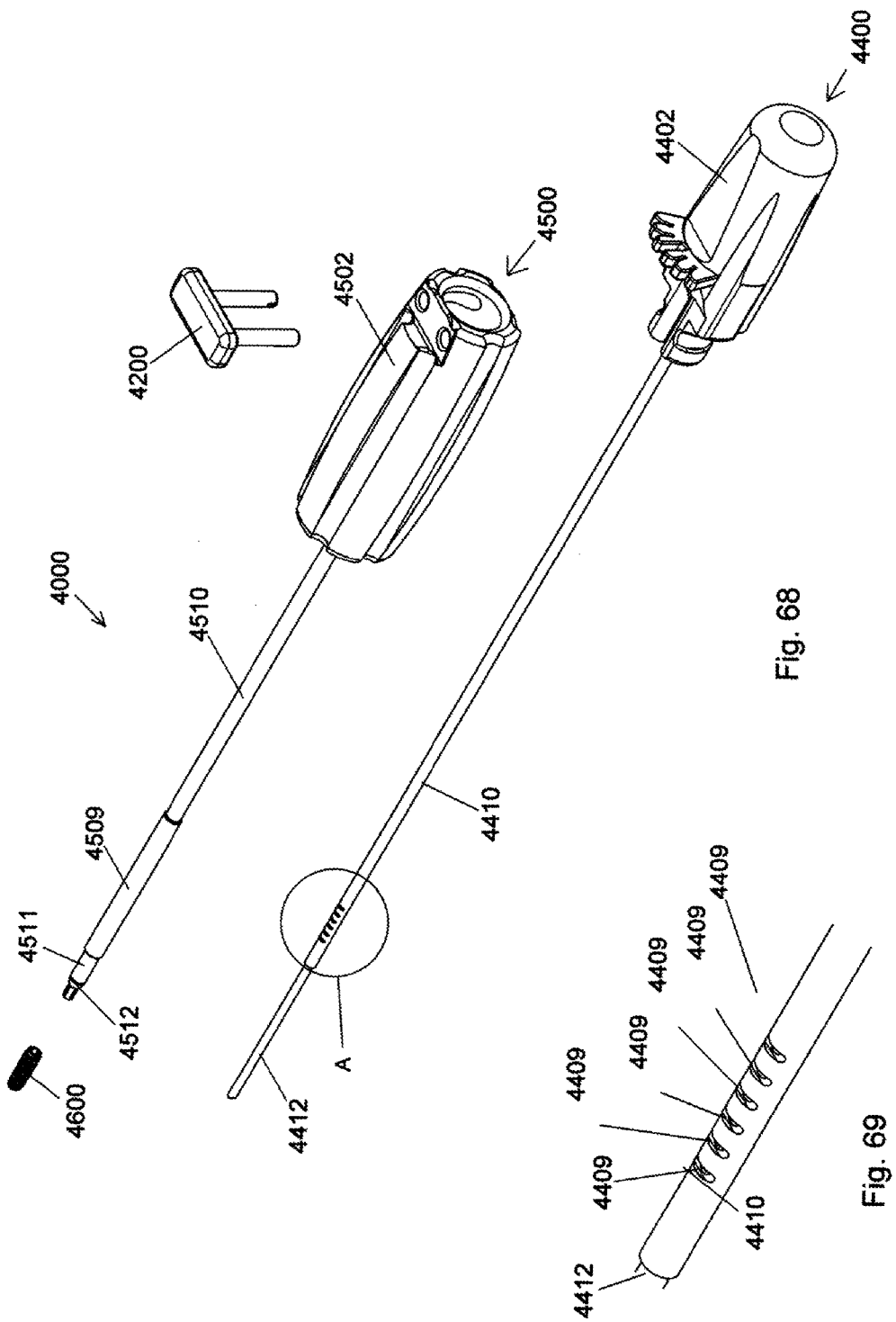

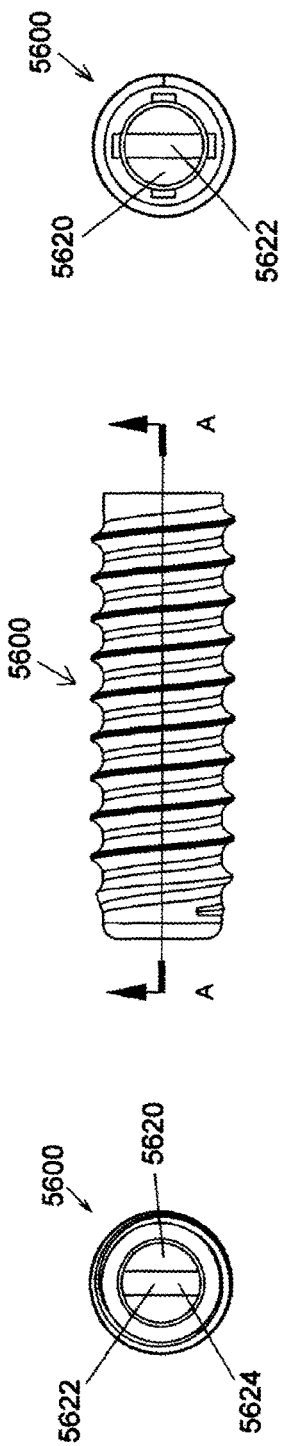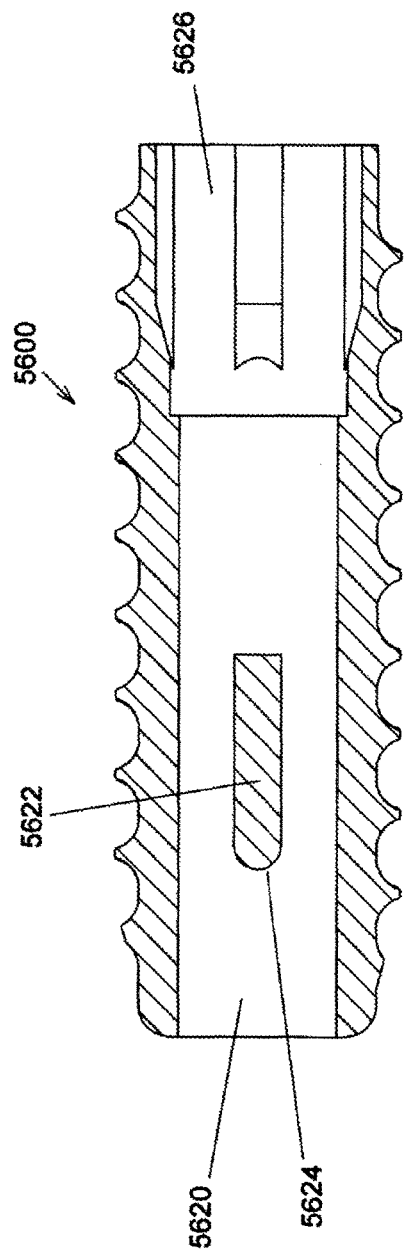

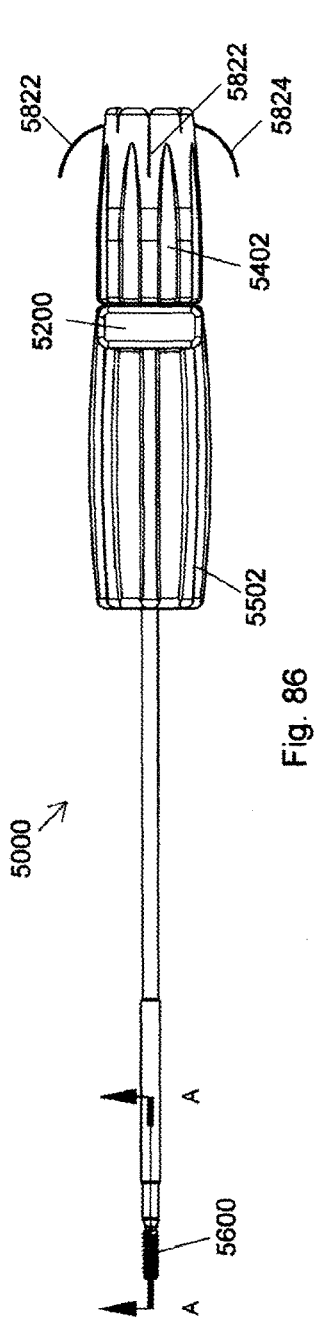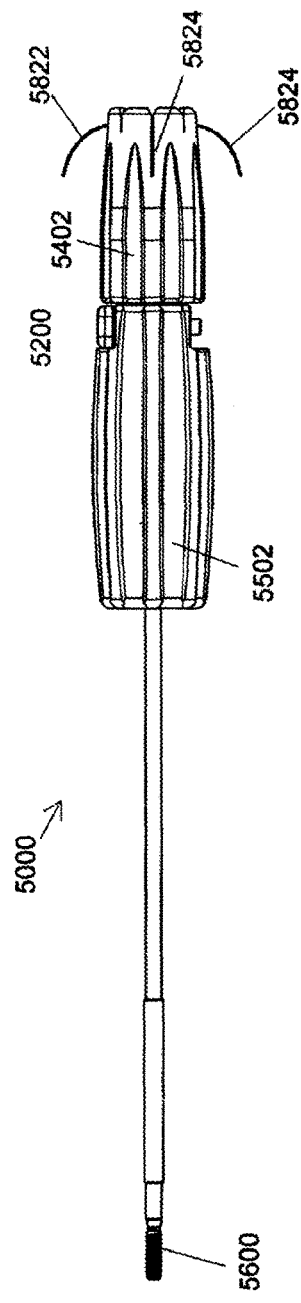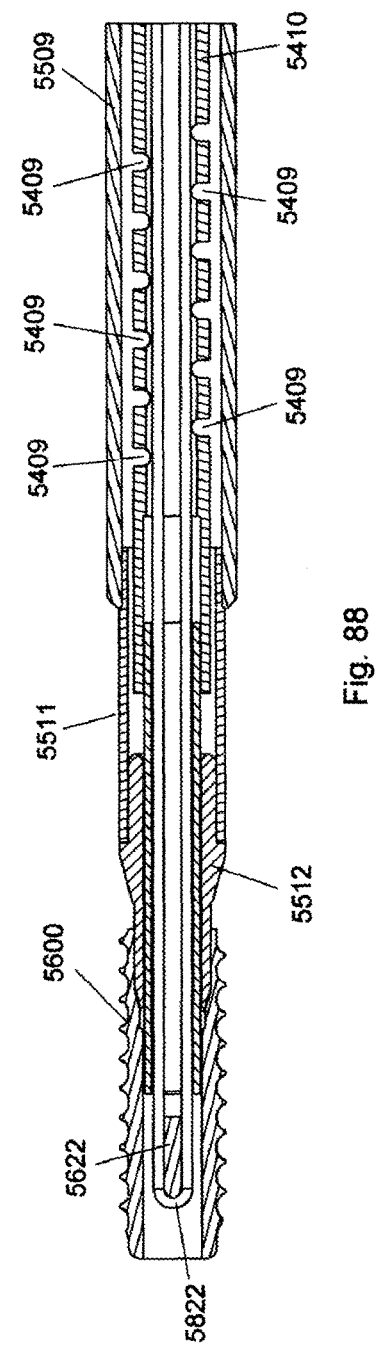
Fig. 86
Fig. 87
Fig. 88

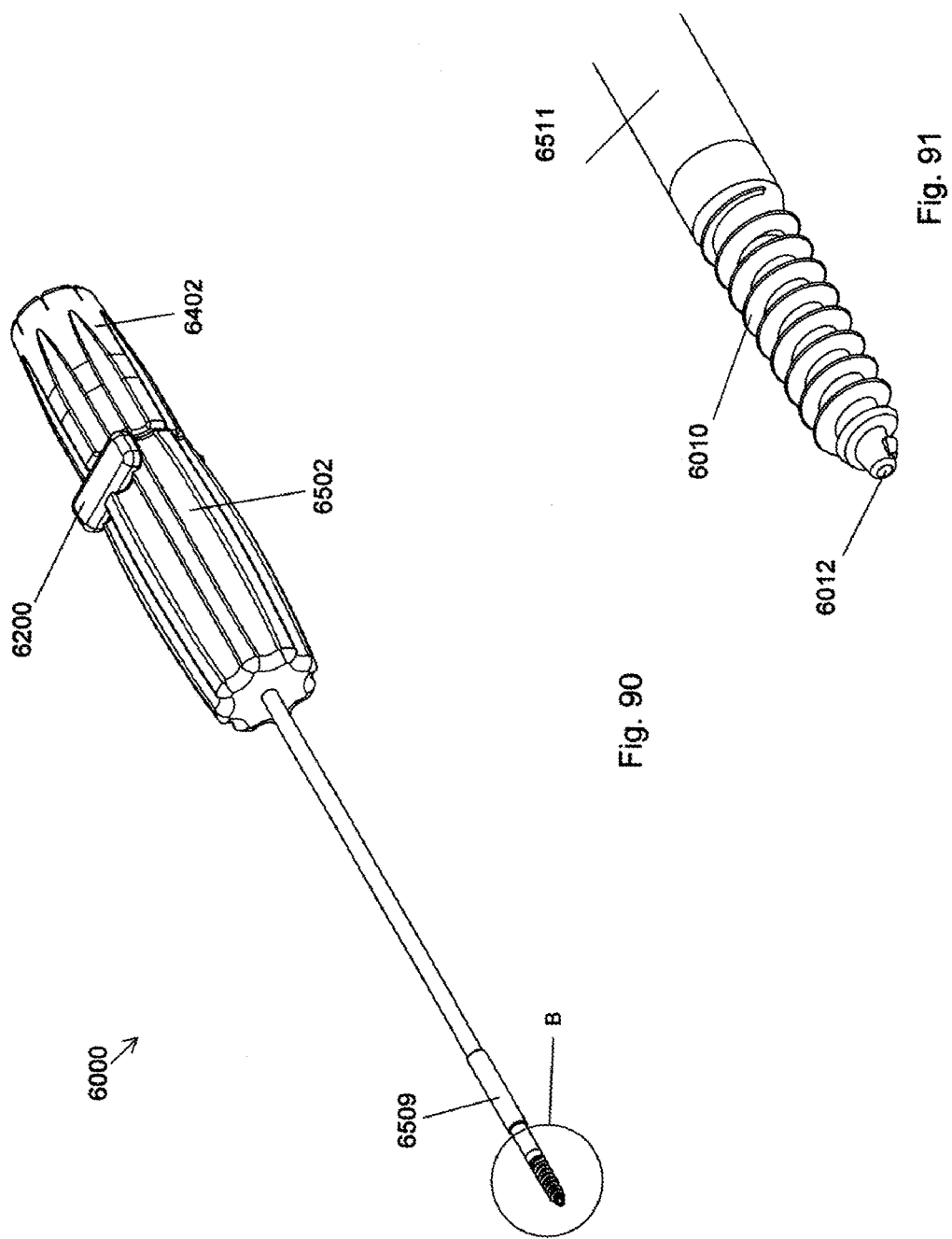

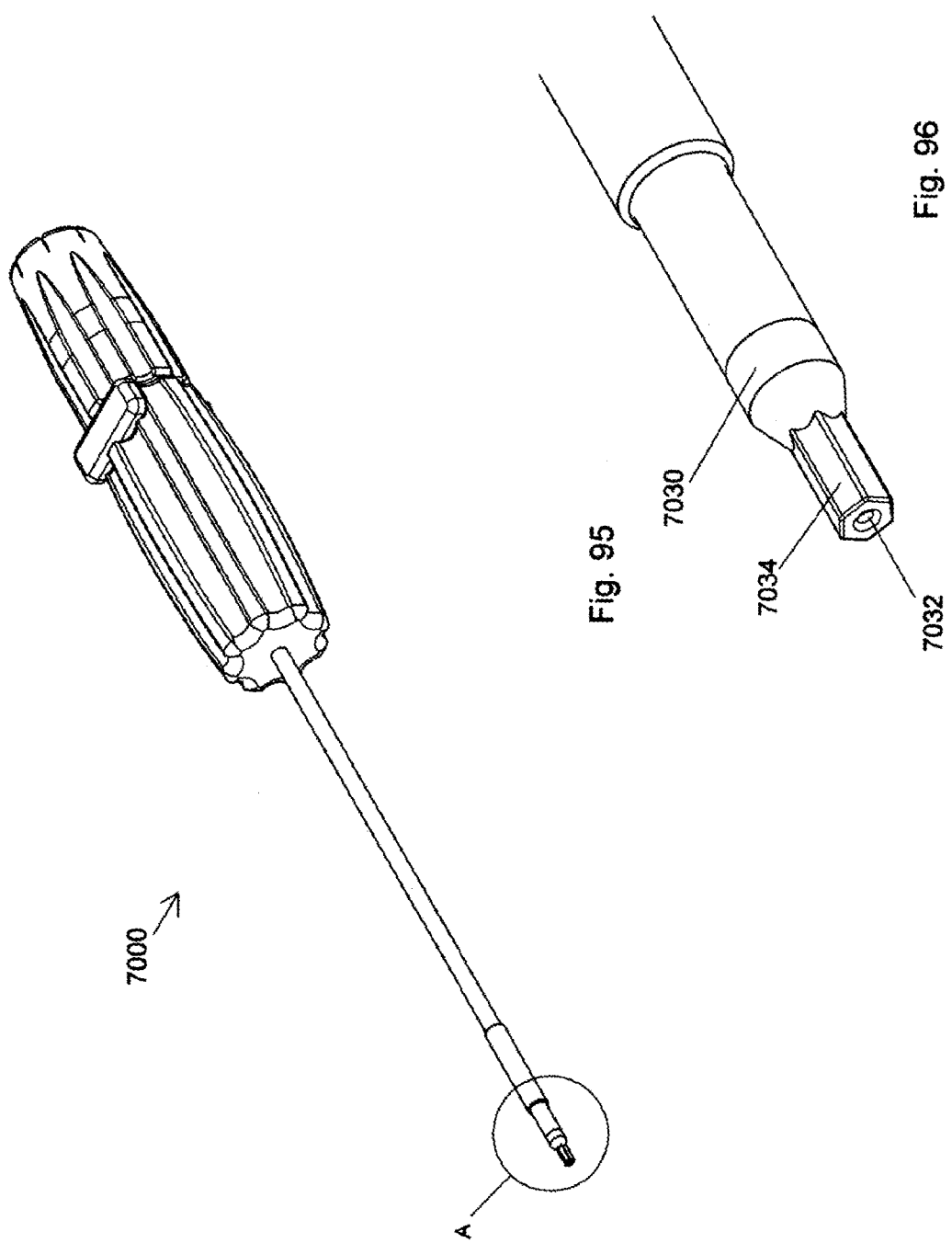

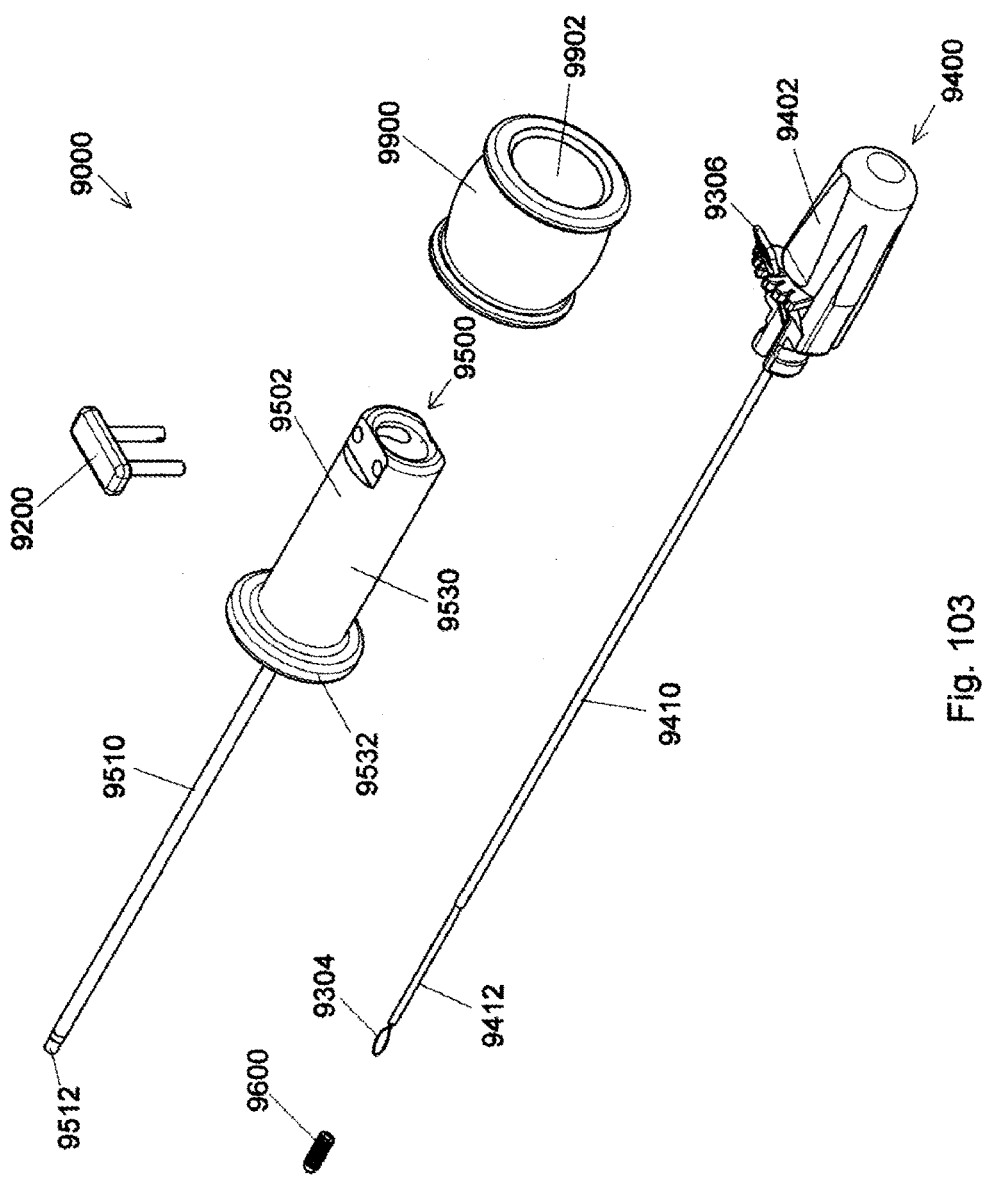

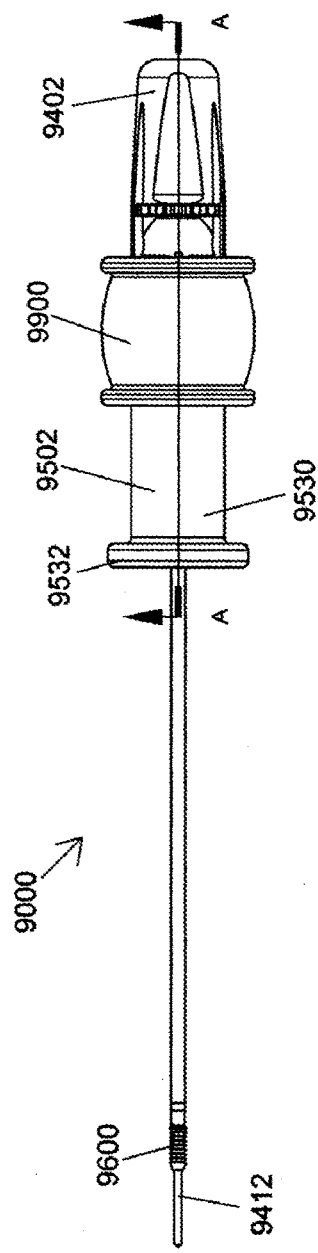
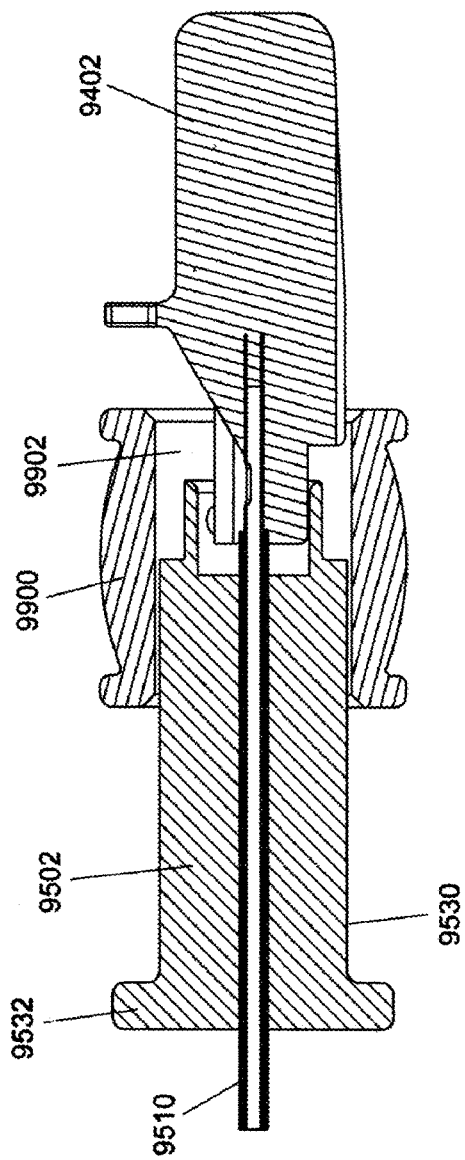

IMPLANT PLACEMENT SYSTEMS, DEVICES, AND METHODS

PRIORITY

This application is a continuation of U.S. patent application Ser. No. 14/636,389 filed Mar. 3, 2015, now U.S. Pat. No. 9,226,817, which, in turn, claims the benefit of U.S. Provisional Application Ser. No. 61/966,744 filed Mar. 3, 2014; 61/998,391 filed Jun. 26, 2014; 61/998,766 filed Jul. 7, 2014; and 61/999,405 filed Jul. 26, 2014, the contents of which are hereby incorporated by reference in their entirety.

TECHNICAL FIELD OF THE INVENTION

The present invention relates generally to the field of endoscopic and arthroscopic surgery and suture anchor systems for use therein. More particularly, the invention relates to a knotless suture anchor system utilized to secure a soft tissue to boney surface to preclude the need to tie surgical knots to secure the tissue in place with the device. Specifically, the invention relates to a simplified anchor placement system and method by which the surgeon may introduce one or more sutures into a hole in the bone, apply tension to the sutures to advance the soft tissue to a desired location, and then advance the anchor into the bone while maintaining suture tension.

BACKGROUND OF THE INVENTION

The use of implants to affix tissue grafts to bone is well known in the orthopedic arts. Common procedures in which such implants are used include, for example, the repair of rotator cuff tears, the repair of torn ligaments in the knee, among others. In these procedures, a socket is drilled or punched in the bone at the attachment site and a graft is secured to the bone using an implant placed in the socket. The graft may be secured to the implant by sutures, or, alternatively, an end of the graft may be placed in the socket and secured directly by an implant.

In rotator cuff repair implants commonly referred to as "anchors" are used. These anchors occur in two types: conventional anchors, in which the suture is passed through the cuff after anchor placement, and "knotless" anchors, in which the suture is passed through the cuff prior to anchor placement. In the former case, the graft is secured in place by tying knots in the suture after it has been passed through the cuff so as to secure the cuff in the desired location. Conversely, as the name implies, when using a knotless anchor, the sutures are passed through the cuff and through a locking feature of the anchor such that when the anchor is inserted into the socket, the suture position is secured by the anchor. The tying of knots is not required. This is particularly advantageous when performing endoscopic (arthroscopic) repairs since the tying of knots arthroscopically through a small diameter cannula may be difficult for some surgeons and, moreover, there is an opportunity for tangling of the sutures.

Knotless suture anchor fixation is a common way of repairing soft tissue that has been torn from bone. The procedure requires drilling or punching of holes into a properly prepared boney surface. After suture has been passed through soft tissue the suture anchor is introduced into the socket and driven into the socket using a mallet or by screwing the anchor into the socket using a driver device. These driver devices typically resemble a screwdriver in form, having a proximal handle portion for applying torque or percussive force, and an elongate rigid distal portion having at its distal end a torque or percussive force-transmitting configuration. In the case of torque transmitting drivers used with threaded anchors, the distal end of the driver typically has an elongate hexagonal or square distally extending portion that, through coupling with a lumen in the anchor having a complementary cross-section, transmits torque to the anchor. The lumen may extend through anchor so that the distal portion of the driver protrudes from the distal end of the anchor and rotates with the anchor during anchor placement. Illustrative examples of such "knotless" anchors include the SwiveLock® Knotless Anchor system by Arthrex, Incorporated (Naples, Fla.), the HEALIX Knotless™ Anchor by Depuy/Mitek, Incorporated (Raynham, Mass.), and the Knotless Push-In Anchors such as the Knotless PEEK CF Anchor by Parcus Medical (Sarasota, Fla.)). These anchors and their associated repair techniques have certain drawbacks, primarily stemming from difficulties in maintaining suture separation and preventing rotation of sutures during anchor placement. For example, in the case of the SwiveLock®, the suture is placed at the bottom of the socket via a PEEK (PolyEther Ether Ketone) eyelet that remains at the bottom of the hole. This eyelet can fracture at insertion resulting in a loss of rotational control of the sutures which, in turn, results in suture spin and variation in the tension as well as possible loss of fixation of the suture tension and loss of the suture from the eyelet, all of which add up to failure of the anchor. In the case of the HEALIX Knotless™ anchors, the sutures pass directly through the body of the anchor and, upon insertion of the anchor, the sutures spin around the anchor, thereby resulting in incomplete tension on the sutures as well as change in the suture tension—both of which can result in movement of the tissue through which the suture was placed.

In U.S. Pat. No. 6,544,281, ElAttrache et al. describe a cannulated driver having a rotating inner member and a stationary outer member, wherein the rotating inner member serves to drive the threaded anchor. The rotating member extends past the distal end of the anchor and is inserted into a prepared socket in the boney surface. Sutures attached to the graft, i.e., captured sutures, are used to draw the graft to the desired position prior to placement of the anchor. However, because the sutures are captured to or pass through the rotating inner member, the sutures are twisted during anchor insertion thereby changing the tension on the sutures and the graft position.

Other knotless anchors such as the ReelX STT™ Knotless Anchor System by Stryker® Corporation (Kalamazoo, Mich.) and PopLok® Knotless Anchors by ConMed Corporation (Utica, N.Y.) have complex constructions and require that the surgeon perform a sequence of steps to achieve a successful anchor placement with the desired suture tension and proper cuff position. The sequence of steps adds to procedure time and creates opportunities for failure of the placement procedure if a step is not performed properly.

Accordingly, there is a need in the art for a knotless anchor system that allows the surgeon to establish the graft position and, while maintaining that position, place the anchor without changing the suture tension or causing a shift in the graft position. Furthermore, if the anchor is threaded, placement of the anchor in the socket must occur without spinning of the suture.

If a graft is directly affixed to a bone by insertion of a graft into a socket (a technique referred to as "bio-tenodesis"), it is essential that the graft be fully inserted so as to engage with the full length of the implant. It is also important that the position of the graft be maintained during anchor insertion. Further, it is essential that the alignment of the implant (in this case referred to as an "interference screw") be coaxial, or if slightly shifted, parallel to the axis of the socket. It is also desirable for the sutures used to draw the graft into the socket not to spin or twist during anchor placement as this may change the position and tension of the graft from that intended by the surgeon. In sum, there is also a need in the suture arts for an interference screw and implant placement system in which graft position within the socket is maintained throughout the implant placement process, and in which suture spin or twisting is prevented.

Current placement systems for threaded implants use a driver that is rigidly coaxial throughout its proximal and distal portions and is coaxial with the implant. Of necessity, the implant is placed coaxially within the prepared socket. Because the sockets are formed using a punch or drill, an item that is itself rigidly coaxial throughout, placement of anchors in sockets so produced are not limited by the rigid coaxial nature of the implant driver devices. This limits the locations in which anchors and interference screws may be placed, particularly when procedures are performed arthroscopically. However, in U.S. Provisional Application Ser. No. 61/965,973 filed Feb. 13, 2014, the contents of which are herein included by reference in its entirety, the present inventors describe a drilling device in which the distal portion may be angularly offset by the surgeon so as to produce holes having an axis offset from that of the more proximal portions of the drilling device. Using devices so configured, it is possible to produce sockets for anchors in locations that cannot be accessed by drills or anchor driver systems in which the distal portion is not angularly offset. Accordingly, there is further a need in the suture arts for anchor systems, both conventional and knotless, and for interference screw placement systems in which anchors may be placed in sockets the axis of which is not coaxial with the driving assembly axis. That is, in which the anchor and the distal portion of the driving assembly are coaxial with the socket, but the other portions of the driver assembly are not. Further, since some implants require that threads be formed in the socket prior to placement of a threaded implant, there is a need in the art for a thread-forming device in which the axis of the rotating thread-forming portion is not coaxial with the proximal portions of the torque producing member. The availability of such "off-axis" drills and implant systems such as contemplated herein will greatly simplify commonly performed procedures, such as Anterior Cruciate Ligament (ACL) repair, since current methods are limited to constructs that can be produced by conventional coaxial drills and interference screw placement systems.

SUMMARY OF THE INVENTION

A primary objective of the present invention is to provide improved means and methods of attaching soft tissues (i.e., "grafts") to bone in situ. The embodiments of the instant invention are described hereinbelow as a system and method for producing a matrix of implants for the anchoring of a graft to bone. Any graft fixation system which uses a driver with a cannulated non-rotating inner assembly and a movable outer assembly to tension sutures in a prepared socket for the placement of a simple one-piece cannulated anchor are contemplated by the present invention. Illustrative aspects and embodiments of the present invention in accordance with the foregoing objective are as follows:

In a first aspect, the present invention provides prosthetic implants and systems for their placement in a target boney surface for the knotless securing of a soft tissue graft thereto. The instant invention contemplates a novel placement system including a non-rotating cannulated inner assembly coaxially positioned within a rotationally and axially movable outer assembly. In a preferred embodiment, a tubular distal element of the inner assembly extends beyond the distal end of the movable outer assembly. A cannulated threaded implant or cannulated interference plug-type anchor may then be positioned on the distal portion of the cannulated inner assembly that extends distally beyond the distal end of the outer assembly, distally adjacent to the distal end of the movable outer assembly. If a threaded implant is used, the distal end of the movable outer assembly preferably includes torque-transmitting features that, together with complementary features formed in the proximal portion of the implant or anchor, allow the transmission of torque thereto. If an interference plug-type anchor is used, the distal end of the movable outer assembly is preferably configured to transmit axial force to the anchor, the distal end of which has suitable complementary features to enable secure attachment.

In operation, sutures placed in the graft are drawn into the distal end of the cannulated inner member. The elongate distal portion of the inner member is inserted into a properly prepared socket in the target boney surface so that the distal end of the inner assembly with its sutures is positioned at the bottom of the socket. Tension is then applied to the sutures by pulling on their proximal ends, which extend beyond the proximal portion of the inner cannulated assembly to move the graft into the desired position, namely into the prepared socket adjacent to the distal element of the inner assembly. The desired tension may be maintained by cleating proximal portions of the suture(s) into slots optionally formed in the handle of the cannulated inner assembly. The anchor (or interference screw) may be then threaded or driven into the socket, thereby trapping the sutures between the anchor exterior surface and the socket wall. Critically, twisting of the sutures is prevented by the stationary inner member. In addition, tension on the sutures and the position of the graft are maintained throughout the procedure. After anchor placement, the placement system is withdrawn and the sutures trimmed to complete the procedure.

The system and method of the instant invention provide a simplification over other currently available anchoring methods and hardware in that fewer steps are required and moreover the anchor has a simple, single-piece construction. The anchor system is scalable and, due to its simple construction, may be used with anchors smaller than those permitted using other currently available systems. The composition and construction in the anchor may be readily modified simply by changing the material from which it is constructed, by increasing or reducing the diameter or length of the anchor, by increasing or decreasing the wall thickness of the anchor, by modifying the profile of the exterior, or by any combination of these means. All such modifications are contemplated as within the scope of the present invention.

In another aspect, the present invention provides a method for affixing a soft tissue graft to a target boney surface, the method comprising the steps of:
  a. providing a placement system having a cannulated non-rotating inner assembly and a cannulated movable outer assembly,
  b. attaching a cannulated anchor to the distal end of the outer assembly, positioned over a distally extending element of the inner assembly, c. producing a suitably configured hole (i.e., "socket") in a prepared boney surface at a desired target location using a drill, tap, punch or equivalent hole-producing device,
d. drawing sutures from the graft into the lumen of the cannulated inner assembly,
e. inserting the distal end of the inner assembly into the socket,
f. applying tension to the sutures to draw the graft to a desired position,
g. placing the anchor (or interference screw) in the socket,
h. withdrawing the placement system,
i. trimming the suture tails, and
j. optionally repeating steps (c) through (i) as required.

In a further aspect, the present invention provides a system for placing anchors in a prepared socket in which the placement and orientation of the socket precludes placement of an anchor using a driver device in which the driver distal portion is rigidly aligned with the proximal portions. In this aspect, the present invention contemplates a novel driver assembly having a distal portion that may be adjusted to be angularly offset from the proximal portion of the driver so as to bring the anchor to be placed in coaxial alignment with the socket. In the context of the present invention, anchors placed may be either of the knotless configuration or may be conventional anchors pre-loaded with suture.

In accordance with the above additional aspect, the present invention also provides a method for securing a soft tissue graft to a boney surface through the placing of a threaded implant in a socket prepared in a boney surface, wherein the location of the socket precludes insertion using a rigidly coaxial drilling device. Accordingly, the present invention contemplates a method comprising the steps of:
(a) providing an implant placement system having a distal portion that may be angularly offset from the proximal portions;
 a. providing a cannulated threaded implant;
 b. forming a hole (i.e., "socket") in the prepared boney surface at a predetermined target location using, for example, a drill, tap, punch or equivalent hole-producing device;
 c. angularly offsetting the distal portion of the placement system to allow coaxial placement of the cannulated threaded implant;
 d. drawing sutures from a graft into the lumen of the cannulated inner assembly,
 e. inserting the distal end of the inner assembly into the socket,
 f. applying tension to the sutures to draw the graft to a desired position;
 g. placing the threaded implant in the socket,
 h. withdrawing the placement system,
 i. trimming the suture tails, and
 j. optionally repeating steps (b) through (i) as required.

These and other aspects are accomplished in the invention herein described, directed to prosthetic implants and systems for their placement in a target boney surface for the knotless securing of a soft tissue graft thereto. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 1A is a plan view of the outer assembly and anchor of an implant placement system constructed in accordance with the present invention.

FIG. 1B is an expanded view of the distal portion of the objects of FIG. 1A at location C.

FIG. 1C is a side elevational sectional view of the objects of FIG. 1A at location A-A of FIG. 1A.

FIG. 2A is a perspective view of the objects of FIG. 1A.

FIG. 2B is an expanded view of the distal portion of the objects of FIG. 2A at location B.

FIG. 3 is a plan view of the inner assembly of an implant placement system constructed in accordance with the present invention.

FIG. 4 is an expanded sectional view of the inner assembly of FIG. 3 at location A-A.

FIG. 5 is an expanded view of the proximal hub portion of the inner assembly of FIG. 3 at location A.

FIG. 35 is a plan view of an inner assembly for a third embodiment implant placement system constructed in accordance with the instant invention.

FIG. 36A is a side elevational view of the objects of FIG. 35.

FIG. 36B is an expanded sectional view of the objects of FIG. 35 at location A-A.

FIG. 46 is a distal axial view of an interference screw of the instant invention.

FIG. 47 is a side elevational view of the objects of FIG. 46.

FIG. 48 is a proximal axial view of the objects of FIG. 46.

FIG. 49 is an expanded sectional view of the objects of FIG. 47 at location A-A.

FIG. 50 is a perspective view of the objects of FIG. 46.

FIG. 51 is a plan view of a fourth embodiment implant placement system of the instant invention configured for the placement of the interference screw of FIG. 46.

FIG. 52 is a side elevational view of the objects of FIG. 51.

FIG. 53 is an expanded sectional view of the objects of FIG. 51 at location A-A.

FIG. 61 is a plan view of the inner assembly for a fourth embodiment implant placement system constructed in accordance with the present invention FIG. 62 is a side elevational view of the objects of FIG. 61.

FIG. 63 is an expanded view of the objects of FIG. 61 at location A.

FIG. 64 is an expanded view of the objects of FIG. 62 at location B.

FIG. 65 is a plan view of the outer assembly for the fourth embodiment implant placement system.

FIG. 66 is a side elevational view of the objects of FIG. 65.

FIG. 67 is a side elevational sectional view of the objects of FIG. 65 at location A-A.

FIG. 68 is an exploded view of the elements of the fourth embodiment implant placement system prior to assembly.

FIG. 69 is an expanded view of the objects of FIG. 68 at location A.

FIG. 76 is a distal axial view of an alternate embodiment suture anchor constructed in accordance with the instant invention.

FIG. 77 is a plan view of the objects of FIG. 76.

FIG. 78 is a proximal axial view of the objects of FIG. 76.

FIG. 79 is an expanded sectional view of the objects of FIG. 77 at location A-A.

FIG. 86 is a plan view of the objects of FIG. 85.

FIG. 87 is a side elevational view of the objects of FIG. 85.

FIG. 88 is an expanded sectional view of the objects of FIG. 86 at location A-A.

FIG. 90 depicts an alternate embodiment of the instant invention, which includes a tapping device for forming threads in a socket in bone, and which has a distal portion which may be angularly offset.

FIG. 91 is an expanded view of the objects of FIG. 90 at location B.

FIG. 95 is a perspective view of an alternate embodiment of the instant invention, which includes a driver device for applying torque to implants, and which has a distal portion which may be angularly offset.

FIG. 96 is an expanded view of the objects of FIG. 95 at location A.

FIG. 103 is an exploded view of the elements forming an alternate embodiment implant placement system formed in accordance with the principles of the present invention for the placement of the interference screw of FIG. 99.

FIG. 111 is a plan view of the objects of FIG. 110.

FIG. 112 is an expanded sectional view of the objects of FIG. 111 at location A-A.

FIG. 116 is an expanded perspective view of the objects of FIG. 115 at location A.

FIG. 117 is a perspective view of a second prior art driver and anchor with the anchor mounted to the driver in preparation for use.

FIG. 118 is an expanded perspective view of the objects of FIG. 117 at location A.

DETAILED DESCRIPTION OF THE PREFERRED EMBODIMENTS

Figure 6:
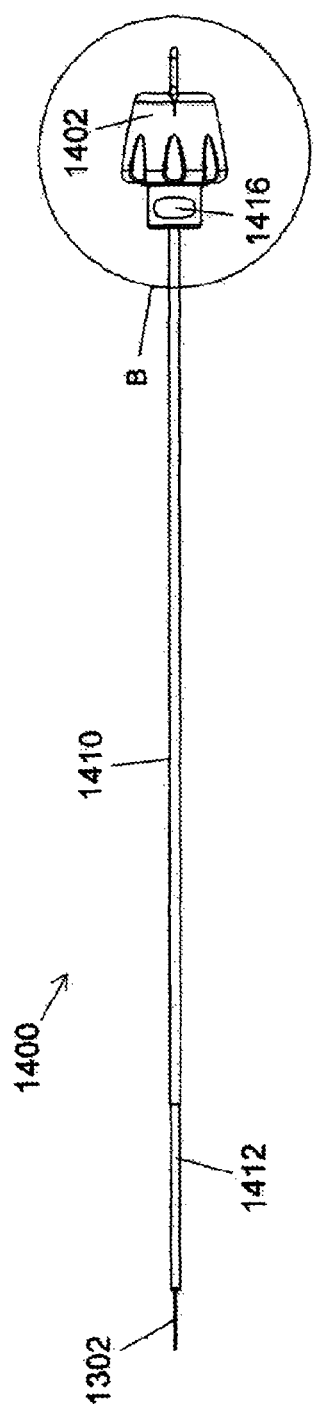
FIG. 6 is a side elevational view of the objects of FIG. 3.
Figure 7:
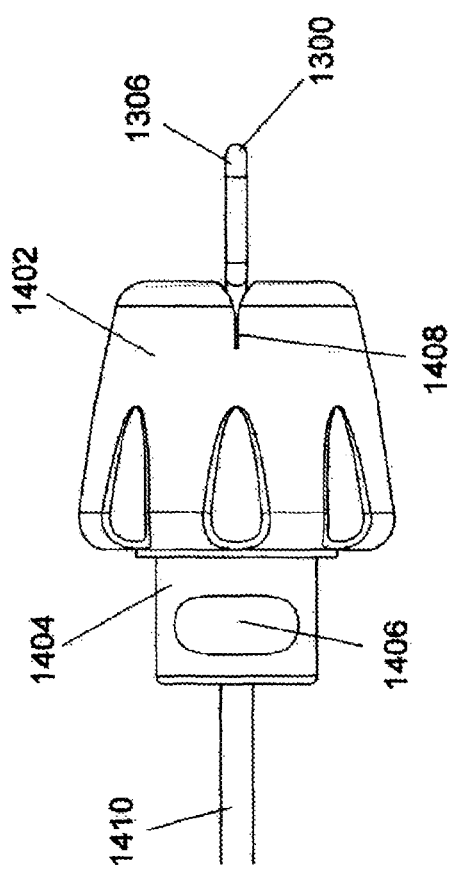
FIG. 7 is an expanded view of the objects of FIG. 6 at location B.
Figure 8:
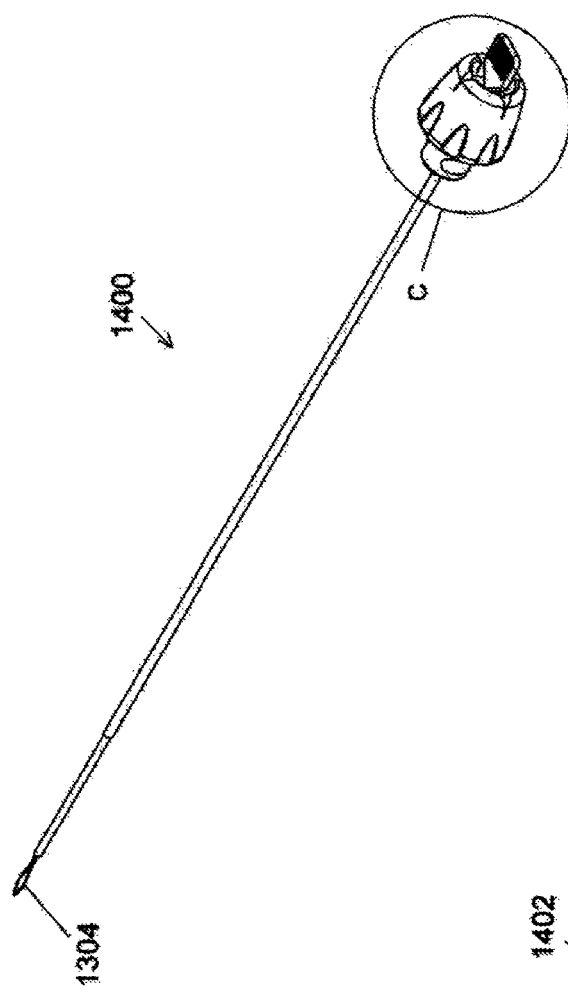
FIG. 8 is a perspective view of the inner assembly of FIG. 3.
Figure 9:
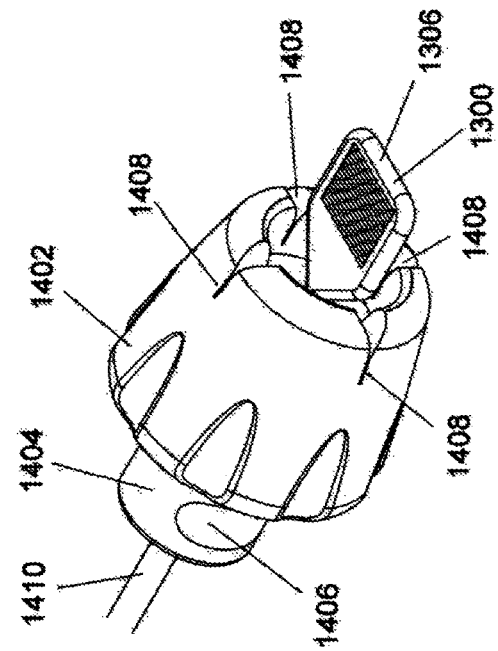
FIG. 9 is an expanded view of the objects of FIG. 8 at location C.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of the implant system of the present invention includes the driver and handle portions.

The term "distal" as used herein refers to that end or portion situated farthest away from the user of the device, closest to the target surgical site. In the context of the present invention, the distal end of the implant systems of the present invention includes components adapted to fit within the pre-formed implant-receiving socket.

In the context of the present invention, the terms "cannula" and "cannulated" are used to generically refer to the family of rigid or flexible, typically elongate lumened surgical instruments that facilitate access across tissue to an internally located surgery site.

The terms "tube" and "tubular" are interchangeably used herein to refer to a generally round, long, hollow component having at least one central opening often referred to as a "lumen".

The terms "lengthwise" and "axial" as used interchangeably herein to refer to the direction relating to or parallel with the longitudinal axis of a device. The term "transverse"

as used herein refers to the direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

As discussed above, when a tissue, more particularly a soft connective tissue in a joint space, becomes damaged or torn from its associated bone or cartilage, surgery is usually required to reattach the tissue or reconstruct the bone. The present invention is directed to various means and mechanisms for securing the displaced tissue to the boney tissue associated therewith.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the repair of connective tissues such as ligaments or tendons, particularly those of the shoulder, elbow, knee or ankle joint.

In a similar fashion, while the present invention is not restricted to any particular boney tissue, a term used herein to refer to both bones and cartilage, aspects of the present invention find particular utility in the repair or reattachment of connective tissues to the boney elements of the shoulder, elbow, knee or ankle joint.

When the damaged tissue is of sufficient quantity and quality, the damaged portion may simply be directly reattached to the bone from which it was torn so that healing back to the bone can take place. However, in other situations, a "graft" may be needed to stimulate regrowth and permanent attachment. In the context of the present invention, the term "graft" refers to any biological or artificial tissue being attached to the boney tissue of interest, including:

Autografts, i.e., grafts taken from one part of the body of an individual and transplanted onto another site in the same individual, e.g., ligament graft;

Isografts, i.e., grafts taken from one individual and placed on another individual of the same genetic constitution, e.g., grafts between identical twins;

Allografts, i.e., grafts taken from one individual placed on genetically non-identical member of the same species; and Xenografs, i.e., grafts taken from one individual placed on an individual belonging to another species, e.g., animal to man.

Autografts and isografts are usually not considered as foreign and, therefore, do not elicit rejection. Allografts and xenografts are recognized as foreign by the recipient thus carry a high risk of rejection. For this reason, autographs and isografts are most preferred in the context of the present invention.

Surgical interventions such as contemplated herein generally require the boney tissue to be prepared for receiving the graft. In the context of the present invention, such preparation includes the formation of a "socket", i.e., a hole punched or drilled into the bone into which a prosthetic device such as an implant may be received. The socket may be prepared at the desired target location using conventional instruments such as drills, taps, punches or equivalent hole-producing devices.

While certain procedures contemplate directly attaching the graft to the bone, the more common route involves the employment of an implant specially configured to hold and/or enable attachment of the graft to the boney tissue. As used herein, the term "implant" refers to a prosthetic device fabricated from a biocompatible and/or inert material. In the context of the present invention, examples of such "implants" include conventional and knotless anchors of both the screw-threaded and interference-fit variety.

The preferred implant system of the present invention is comprised of a cannulated inner assembly (e.g., the insertion device) slidably received within the lumen of a cannulated outer assembly (e.g., the implant driver) that together serve to tension sutures in a prepared socket for the placement of a simple one-piece cannulated anchor. In the Examples below, the present invention makes reference to various lock-and-key type mating mechanisms that serve to establish and secure the axial and rotational arrangement of these device components. It will again be readily understood by the skilled artisan that the position of the respective coordinating elements (e.g., recessed slots and grooves that mate with assorted projecting protrusions, protuberances, tabs and splines) may be exchanged and/or reversed as needed.

The present invention makes reference to insertion devices commonly referred to in the art as "drills" and "drivers", i.e., devices that "drill" the socket and "drive" the implant into the socket. In the context of the present invention, the drills and drivers may be conventional, e.g., rigidly linear as previously herein described, or, as discussed in detail herein, "off-axis", e.g., having an angularly offset distal portion adapted to drill off-axis sockets in boney tissues that are remote and difficult to access and drive therein the corresponding implant, such as an anchor or interference screw.

The present invention contemplates securing the graft to the implant via sutures. In the context of the present invention, the term "suture" refers to a thread-like strand or fiber used to hold body tissues after surgery. Sutures of different shapes, sizes, and thread materials are known in the art and the present invention is not restricted to any particular suture type. Accordingly, in the context of the present invention, the suture may be natural or synthetic, monofilament or multifilament, braided or woven, permanent or resorbable, without departing from the spirit of the invention.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

FIGS. 113 through 116 depict a typical prior art driver device 100 for the placement of an implant 110 for the purpose of securing a graft to a boney surface. Driver 100 has a proximal handle portion 102 and an elongate rigid linear distal portion 104 having a distal portion 106 configured to transmit torque to anchor 110. Anchor 110 has a central lumen 112 with a cross-section complementary to that of distal portion 106 of driver 100. While distal portion 106 of driver 100 and lumen 112 of anchor 112 are depicted with hexagonal cross-sections, other complementary cross-sections such as splines, regular polygons, or slots may be used. Lumen 112 of anchor 110 extends for the entire length of the anchor. In other anchors, lumen 112 extends a predetermined distance from the proximal end of anchor 110. Lumen 112 may have a constant cross-section throughout its length, or may have a proximal portion with a first cross-section configured for the transmission of torque, and a second distal portion having a second cross-section such as, for instance, a cylindrical cross-section.

Figure 117:
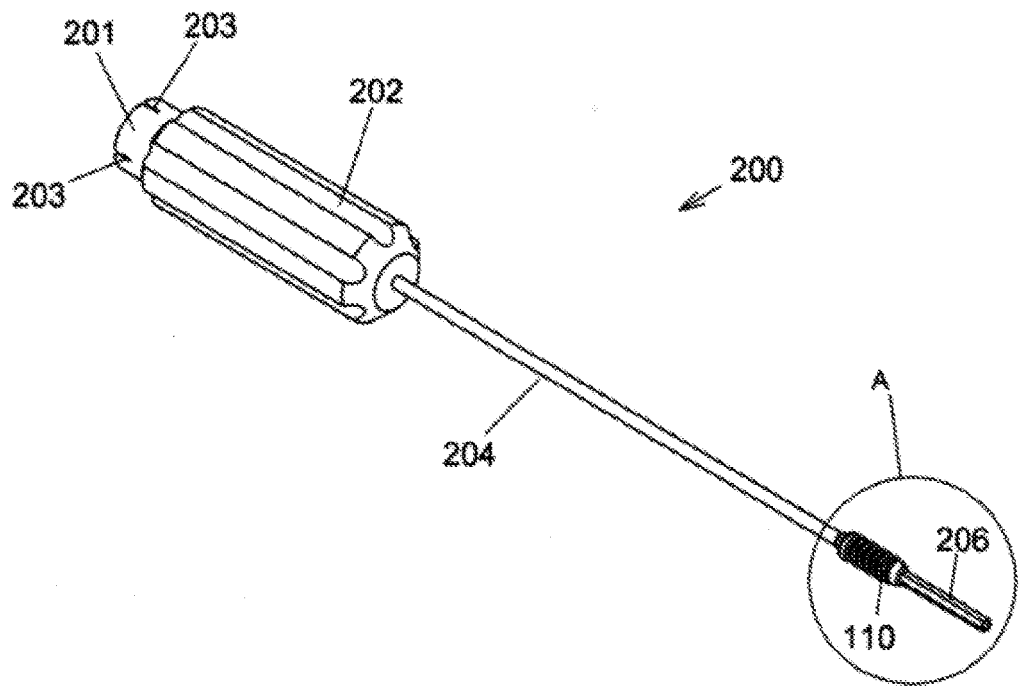
Figure 118:
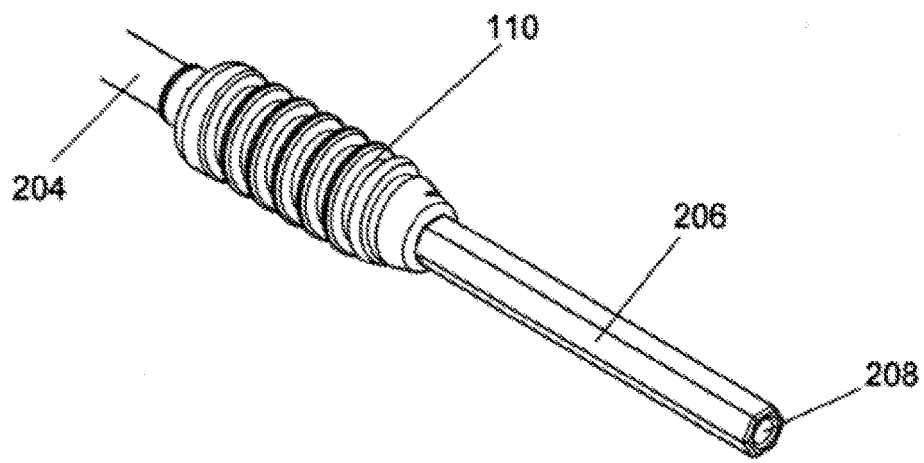

FIGS. 117 and 118 depict a second prior art driver device 200 configured for the placement of anchor 110 in a prepared socket in a boney surface. Device 200 is identical to device 100 except as subsequently described. Distal portion 204 of device 200 has formed therein lumen 208 extending from the distal end of distal portion 206 to the proximal end 201 of handle 202. Proximal end 201 of handle 202 has formed therein slots 203 which function as cleats for the secure retention of sutures placed therein. Distal portion 206 of distal portion 204 has an extended length such that when anchor 110 is mounted thereto for placement in a prepared socket, distal portion 206 protrudes distally beyond anchor 110. In use sutures are drawn into lumen 208 and therethrough to proximal end 201 of handle 202 and secured in cleats 203 so as to maintain their axial positioning relative to driver 200. In a first method of use, the sutures are attached to a graft to be secured to a boney surface using anchor 110. Distal portion 206 of driver 200 is inserted into the socket and the graft is drawn into the desired position by pulling on the proximal portion of the sutures extending beyond proximal end 201 of handle 202, and when the desired graft position is achieved, the sutures are secured in cleats 203. Anchor 110 is then moved distally so as to engage the socket and threaded into the socket by rotating driver 200. Because the sutures are retained within distal portion 206 of driver 200, which is then rotated for anchor placement, twisting of the sutures (also known as "suture spin") frequently occurs. This undesirable twisting of the sutures changes the tension in the sutures and may cause a shift in the position of the graft to an unsuitable or less optimal position.

In another method of use of prior art driver 200, a suture is loaded into the lumen of distal portion 204 with a central loop extending beyond the distal end of portion 206, and with the ends of the suture extending beyond the proximal end 201 of handle 202. The end of a graft to be placed in a prepared socket and secured therein is positioned within the suture loop and retained there by tension applied to the proximal end of the sutures which are then retained in cleats 203. Distal portion 206 of driver 200 with the graft captured thereto is inserted into the prepared socket and secured therein by anchor 210 which traps the graft portion between anchor 110 and the wall of the prepared socket. However, the threading of anchor 110 into the socket by rotation of driver 200 may frequently cause twisting of the distal suture loop and thereby shifting of the graft from its initial desired position to one that is less optimal.

In an attempt to solve this suture twisting problem and the frequent undesirable shift in graft position that results therefrom, manufacturers have mounted to the distal end of distal portion 206 various pivoting eyelets and other elements for graft and suture retention. When used with these distal elements, sutures do not pass through a central lumen, but rather remain exterior to the anchor and thus are trapped between the anchor exterior surface and the wall of the socket during anchor placement and are secured thereby. However, the eyelets or other distal elements are fragile and frequently fail during insertion. Also, in spite of the pivoting nature of their attachment to distal portion 206, the eyelets frequently spin, thereby twisting the sutures and causing the location shift in the graft. Attempts to solve the problem of suture tensioning and graft shift due to twisting of the sutures have been only partially successful. This has resulted in extended procedure times and suboptimal outcomes.

The present invention attempts to address these remaining problems in the art. To that end, FIGS. 1A through 1C and 2A and 2B depict a cannulated outer assembly 1500 for a knotless anchor system of the instant invention, assembly 1500 having a proximal handle 1502 in which is formed a proximal cylindrical recess 1504, and off-axis lateral holes 1506, and a tubular distal portion 1510 having at its distal end tubular drive element 1512. The distal portion 1514 of drive element 1512 is configured complementary to internal drive features 1602 in the proximal portion of the lumen of cannulated threaded anchor 1600 such that torque supplied by outer assembly 1500 is transmitted to anchor 1600. The distal portion of drive element 1512 may have a variety of sizes, configurations and lumen sizes to suit a variety of anchors 1600, the requirements for a particular anchor 1600 depending on its size, configuration and material properties. For example, the complementary drive elements may take the form of an internally or externally positioned hexagonal or square drive, an internal or external spline, or slots positioned internal or external to the anchor.

Referring now to FIGS. 3 through 9 depicting cannulated inner assembly 1400 having a proximal hub 1402 with a distal cylindrical portion 1404 in which are formed off-axis lateral grooves 1406, and cleats 1408 formed in the proximal rim of proximal hub 1402. Inner assembly 1400 has a tubular middle portion 1410, and a tubular distal portion 1412, distal portion 1412 having a diameter 1414 and length 1416. Diameter 1414 is selected such that distal portion 1412 may be slidably positioned within distal drive element 1512 of cannulated outer assembly 1500. Length 1416 is determined such that when inner assembly 1400 is positioned within outer assembly 1500, distal portion 1412 of inner assembly 1400 protrudes beyond distal drive element 1512 of outer assembly 1500 a sufficient distance so that when anchor 1600 is mounted on distal drive element 1512 and distal portion 1412 is inserted to the full depth of a suitable socket formed in bone, anchor 1600 is still proximal to and clear of the socket. Elongate wire element 1302 having at its distal end loop 1304 and at its proximal end polymeric element 1306 forming a pull tab forms a loading loop 1300 for drawing sutures into the lumens of tubular members 1410 and 1412.

Figure 11:
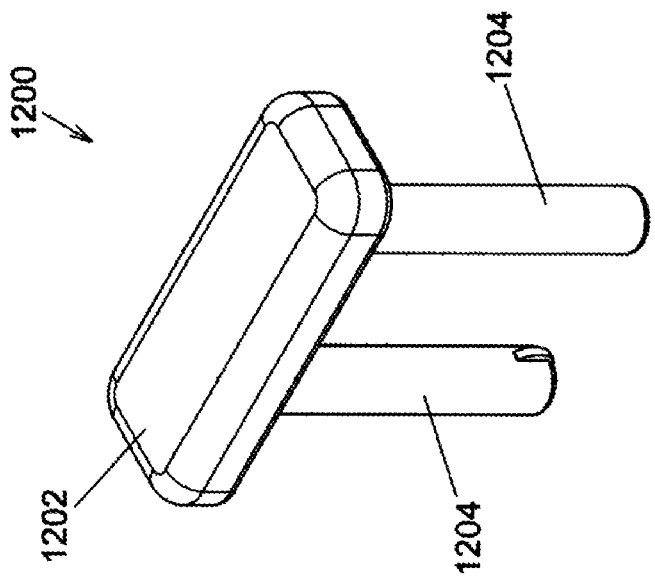
FIG. 11 is a perspective view of the objects of FIG. 10.
Figure 10:
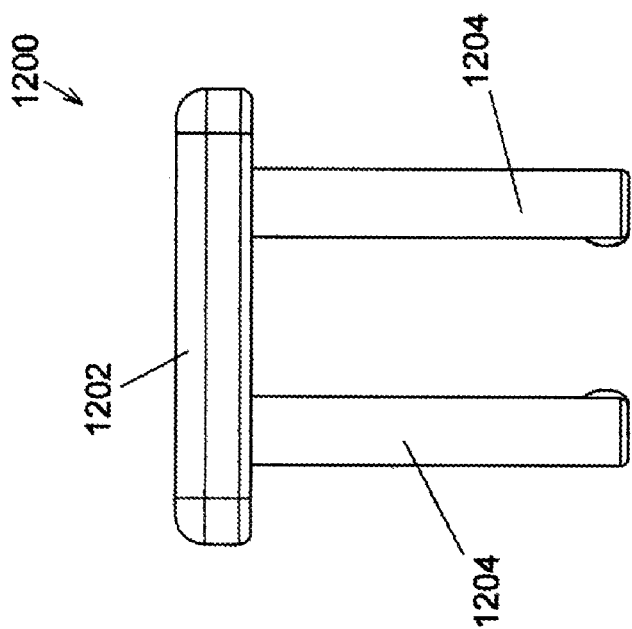
FIG. 10 is a side elevational view of a key for an implant placement system constructed in accordance with the present invention.

FIGS. 10 and 11 depict key 1200 having a planar portion 1202 and cylindrical portions 1204 which are sized and spaced such that cylindrical portions 1204 may be inserted into off-axis lateral holes 1506 of handle 1502 of cannulated outer assembly 1500.

Figure 12:
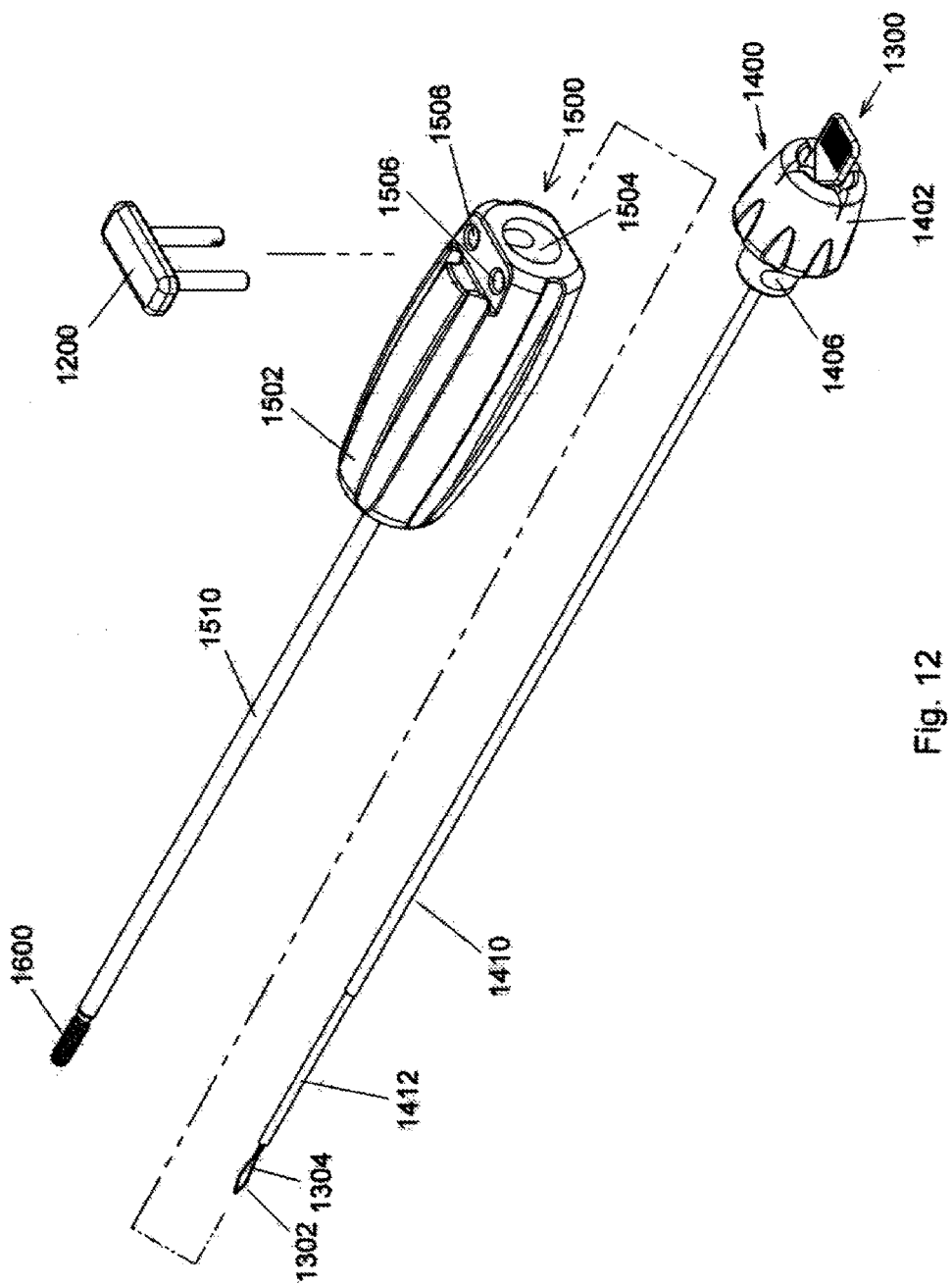
FIG. 12 is an exploded view of the assembly of a first embodiment of an implant placement system constructed in accordance with the present invention.
Figure 13:
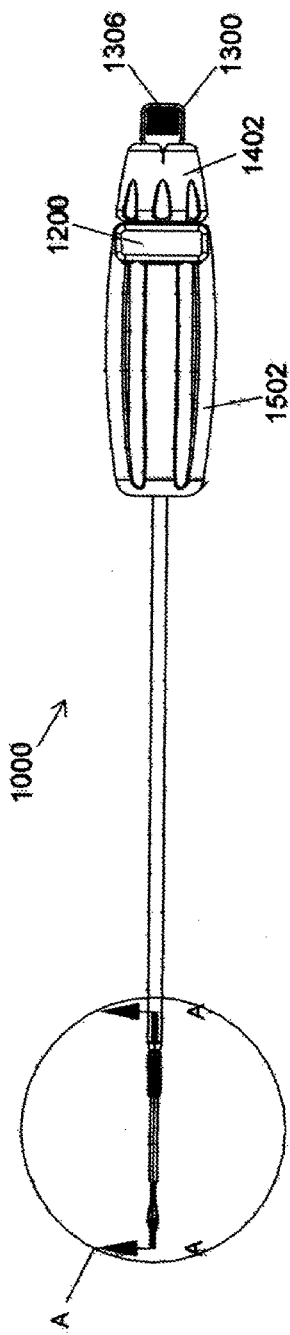
FIG. 13 is a plan view of a fully assembled first embodiment of an implant placement system constructed in accordance with the instant invention.
Figure 14:
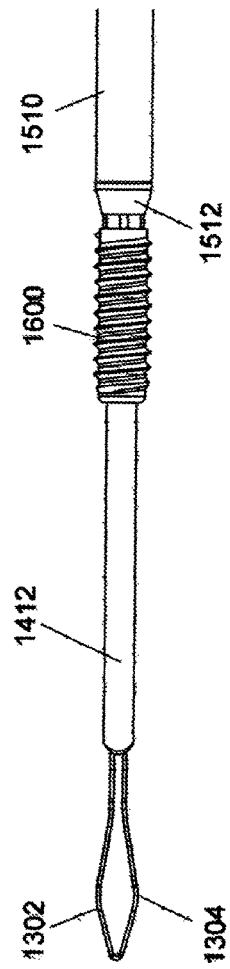
FIG. 14 is an expanded view of the distal portion of FIG. 13 at location A.
Figure 15:
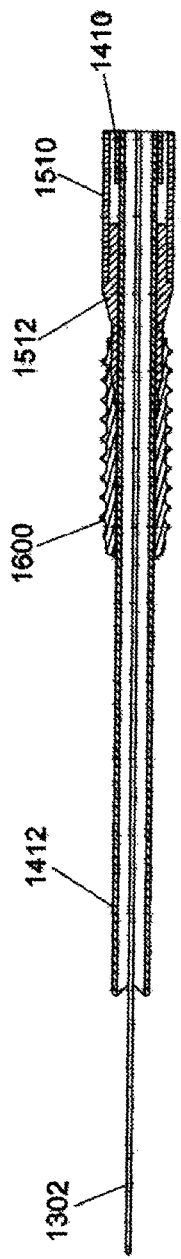
FIG. 15 is an expanded side elevational sectional view of the objects of FIG. 13 at location A-A.
Figure 16:
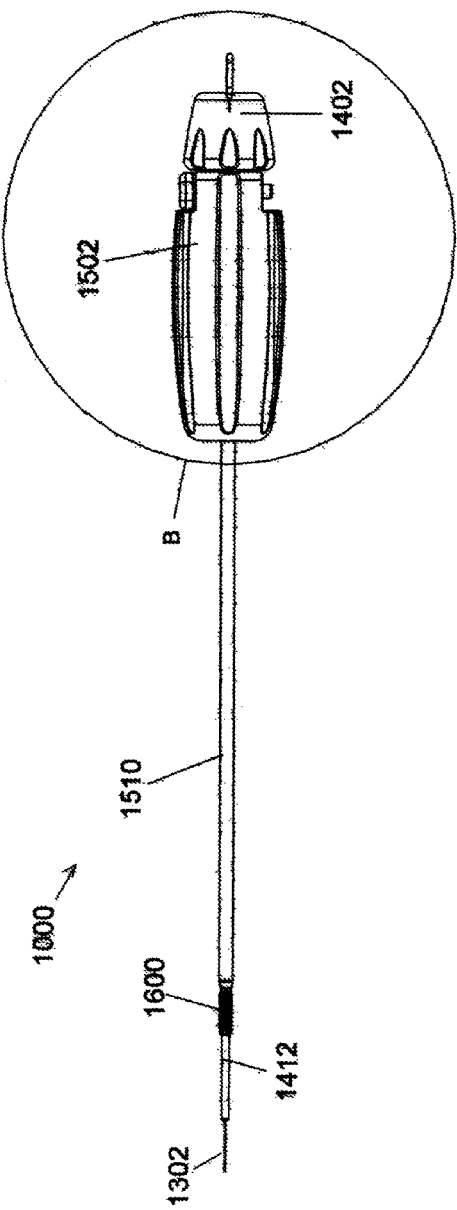
FIG. 16 is a side elevational view of the objects of FIG. 13.
Figure 17:
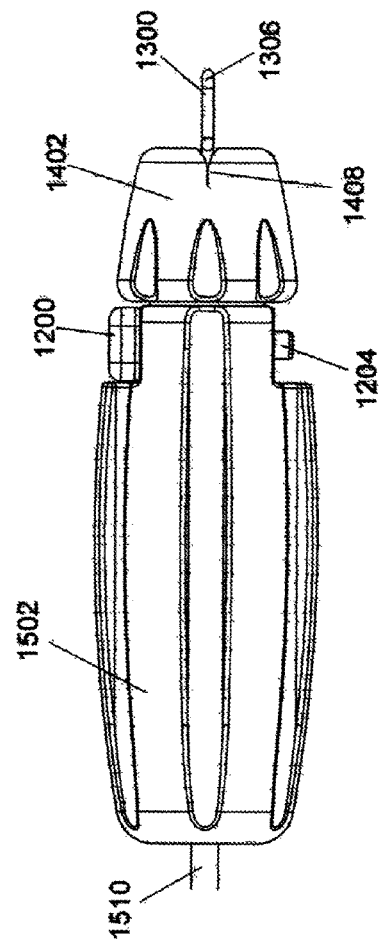
FIG. 17 is an expanded view of the objects of FIG. 13 at location B.
Figure 18:
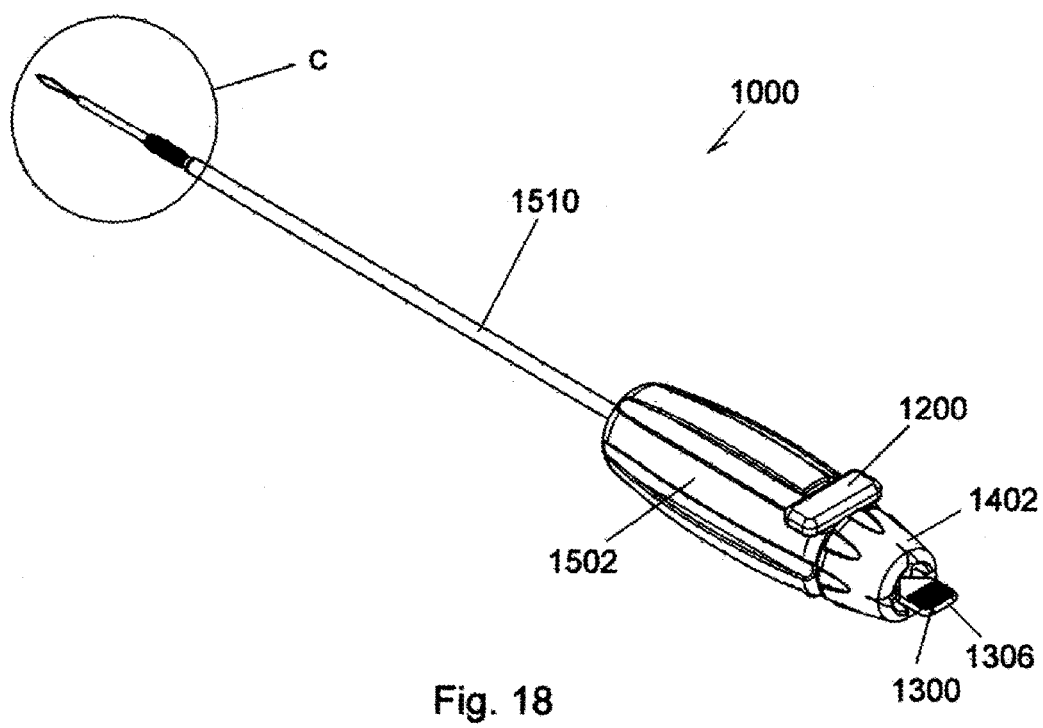
FIG. 18 is a perspective view of the objects of FIG. 13.
Figure 19:
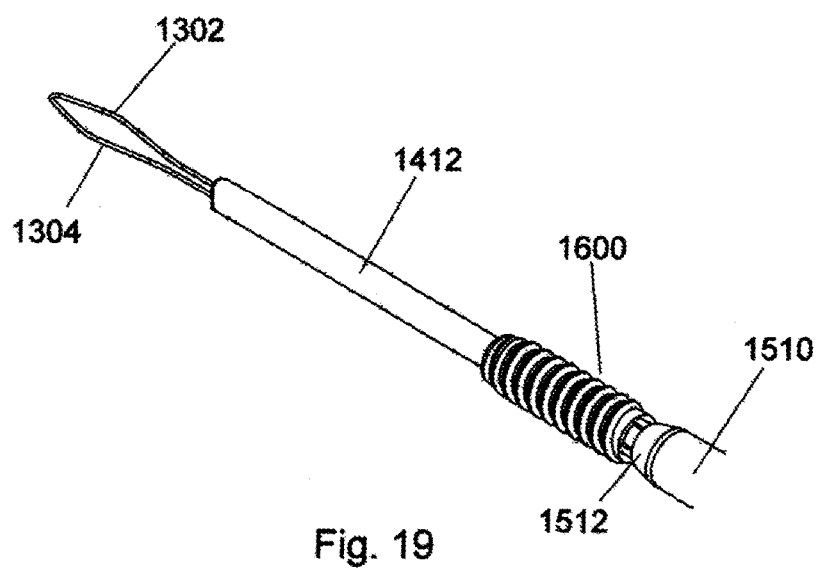
FIG. 19 is an expanded view of the objects of FIG. 13 at location C.

FIG. 12 depicts cannulated outer assembly 1500 with anchor 1600 loaded thereto, inner assembly 1400 with loading loop 1300 positioned for loading a suture, and key 1200 prior to mounting of outer assembly 1500 to inner assembly 1400 in preparation for use. When outer assembly 1500 is mounted to inner assembly 1400, off-axis slots 1406 of handle 1402 of inner assembly 1400 are aligned with off-axis holes 1506 of handle 1502 of outer assembly 1500 and cylindrical portions 1204 of key 1200 are inserted into the passages so formed. Positioning of key 1200 in this manner prevents axial and rotational movement of inner assembly 1400 relative to outer assembly 1500. FIGS. 13 through 19 depict knotless suture anchor system 1000 of the instant invention prepared for use with key 1200 and loading loop 1300 in place.

In the embodiment previously herein described, cannulated outer assembly 1500 is releasably maintained in axial and rotational position relative to inner assembly 1400 by key 1200 and complementary features of handles 1402 and 1502. Other embodiments are contemplated in which the relative positioning is releasably maintained by complementary releasable elements including sliding elements, push-buttons, or various releasable spring elements. Indeed, any mechanism for maintaining axial and rotational alignment between handles 1402 and 1502 which may be released by the surgeon during use falls within the scope of this invention.

Figure 20:
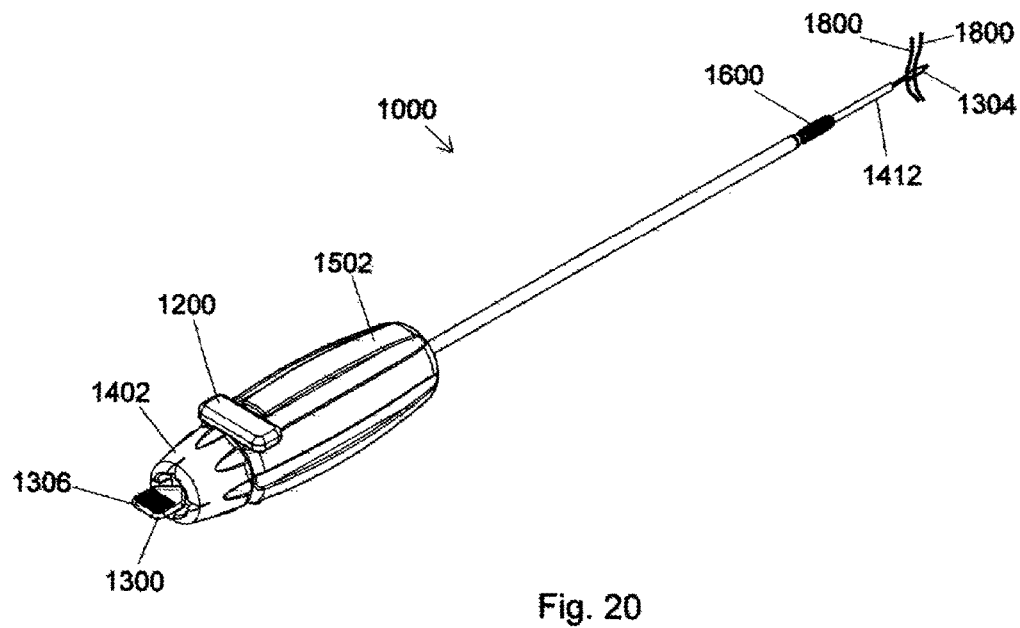
FIG. 20 is a perspective view of a first embodiment implant placement system with sutures being loaded into the system.
Figure 21:
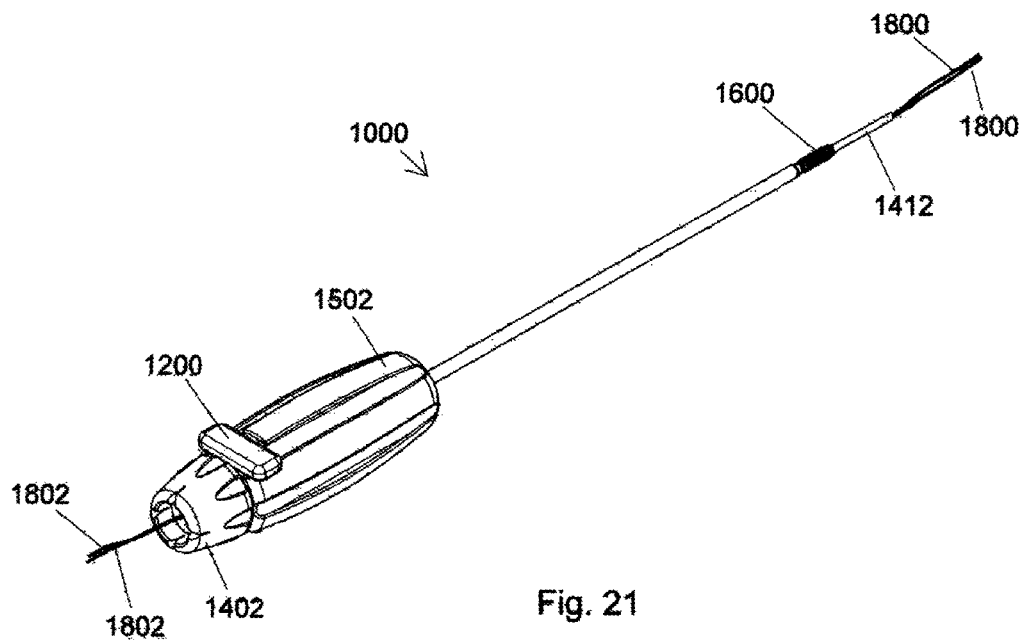
FIG. 21 is a perspective view of the first embodiment implant placement system with the sutures loaded.

Sutures 1800 are loaded into system 1000 by placing the proximal ends of sutures 1800 in distal loop 1304 of loading loop 1300 as depicted in FIG. 20. Tab 1306 of loading loop 1300 is withdrawn proximally until proximal ends 1802 of sutures 1800 extend proximally beyond hub 1402 of inner assembly 1400 as depicted in FIG. 21.

Figure 22:
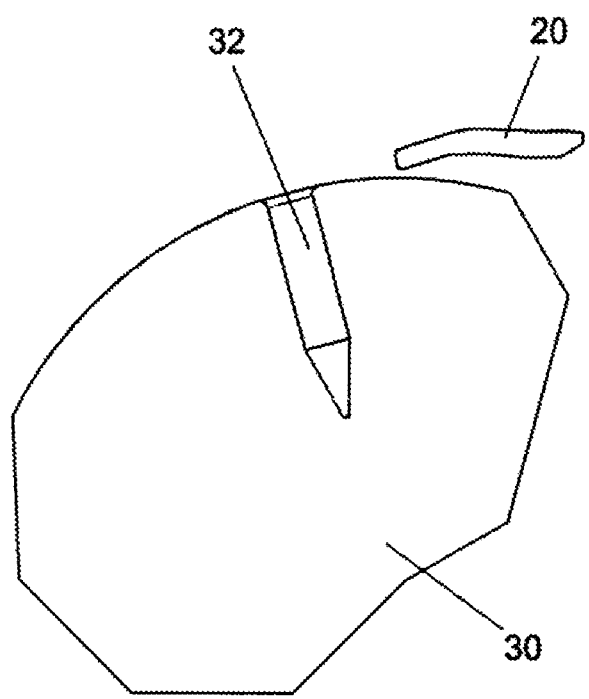
FIG. 22 schematically depicts a socket placed in a bone prior to the placement of an implant.
Figure 23:
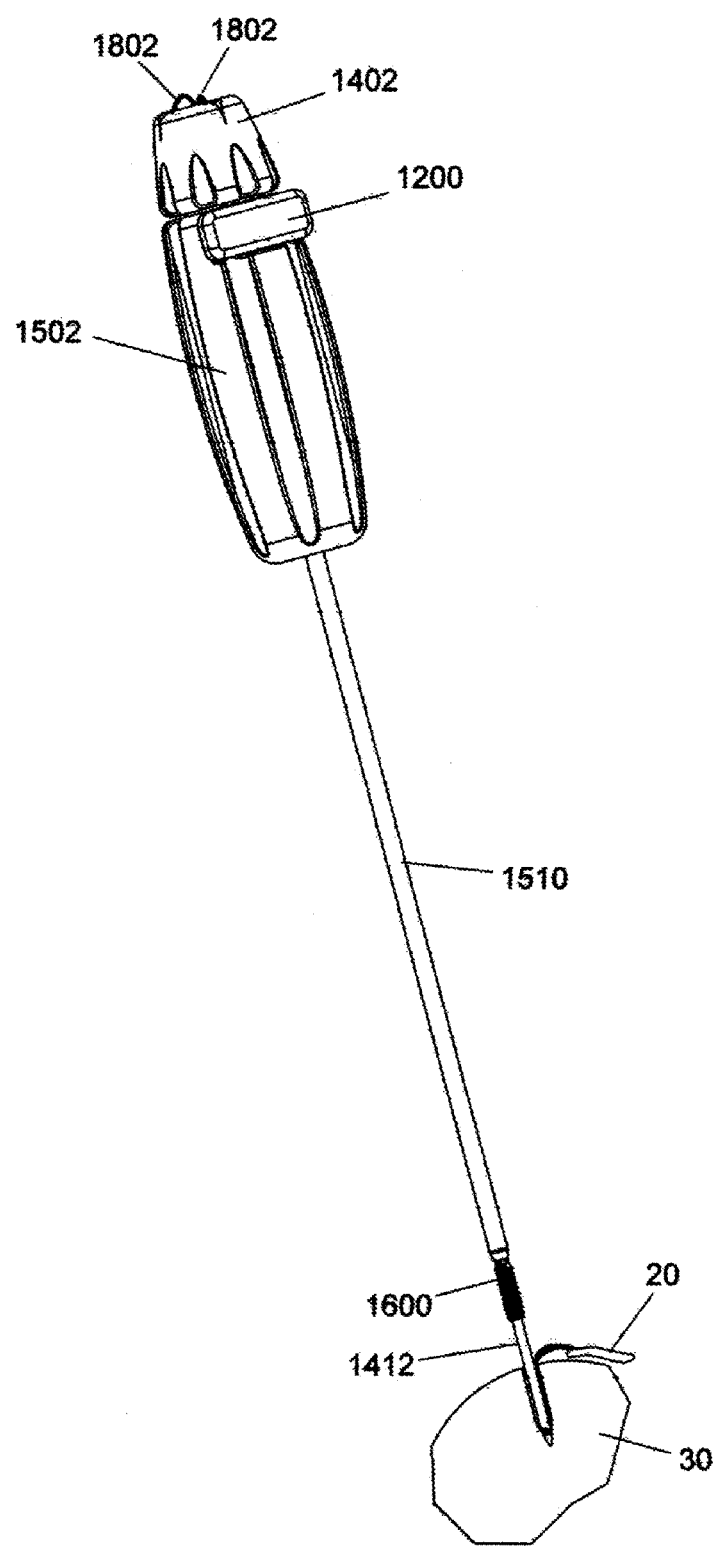
FIG. 23 depicts the first embodiment implant placement system positioned for the first step of implant placement.
Figure 24:
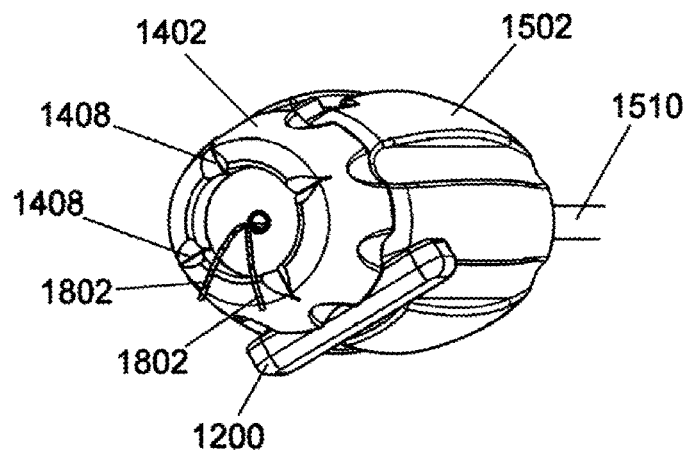
FIG. 24 depicts the proximal portion of the first embodiment implant placement system during the first step of implant placement.
Figure 25:
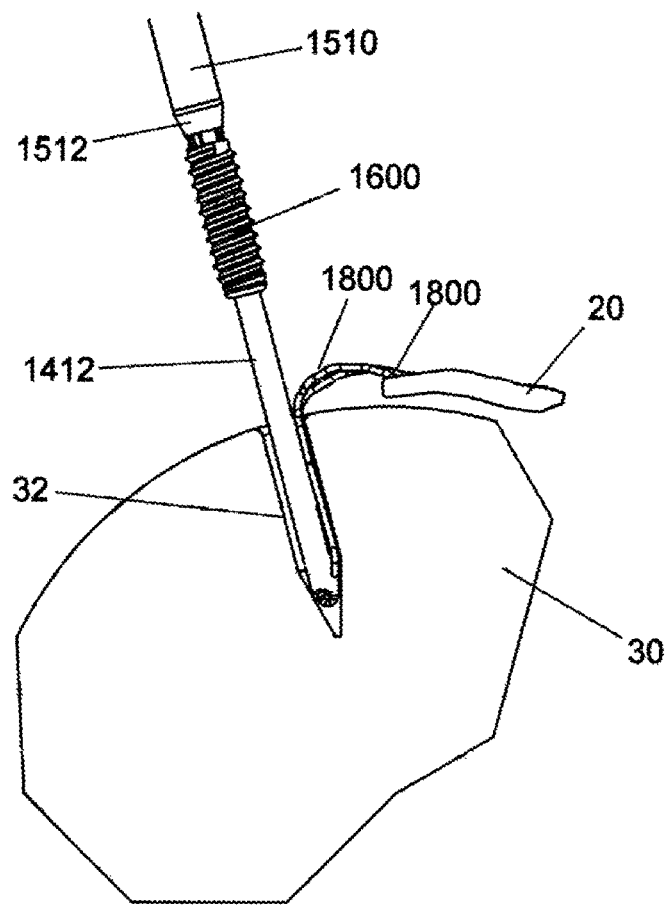
FIG. 25 depicts the distal portion of the first embodiment implant placement system during the first step of implant placement.
Figure 26:
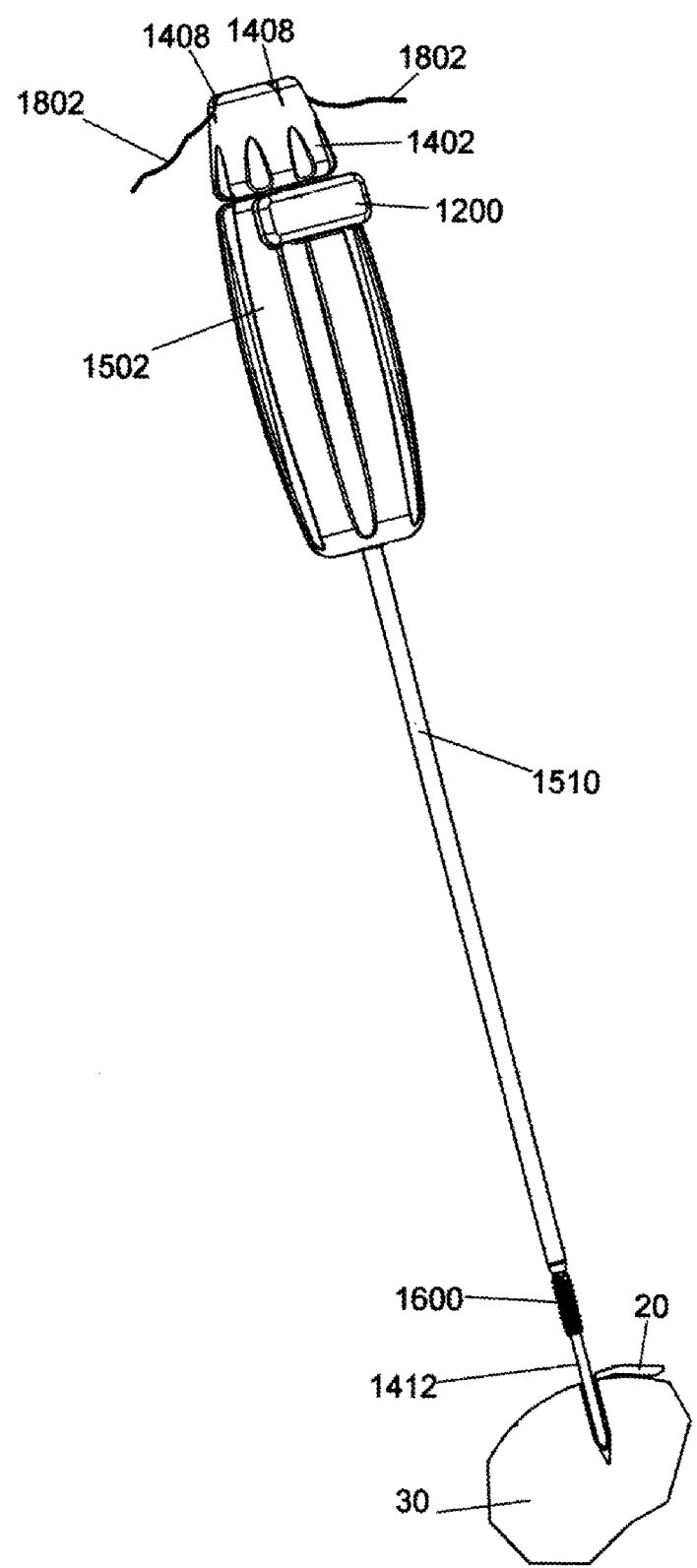
FIG. 26 depicts the first embodiment implant placement system positioned for the second step of implant placement.
Figure 27:
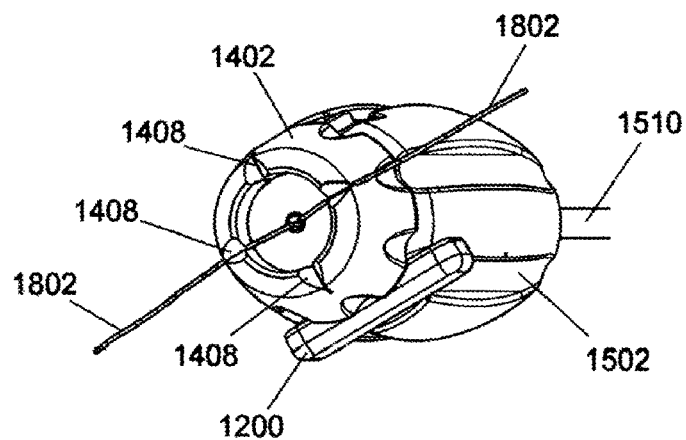
FIG. 27 depicts the proximal portion of the embodiment implant placement system during the second step of implant placement.
Figure 28:
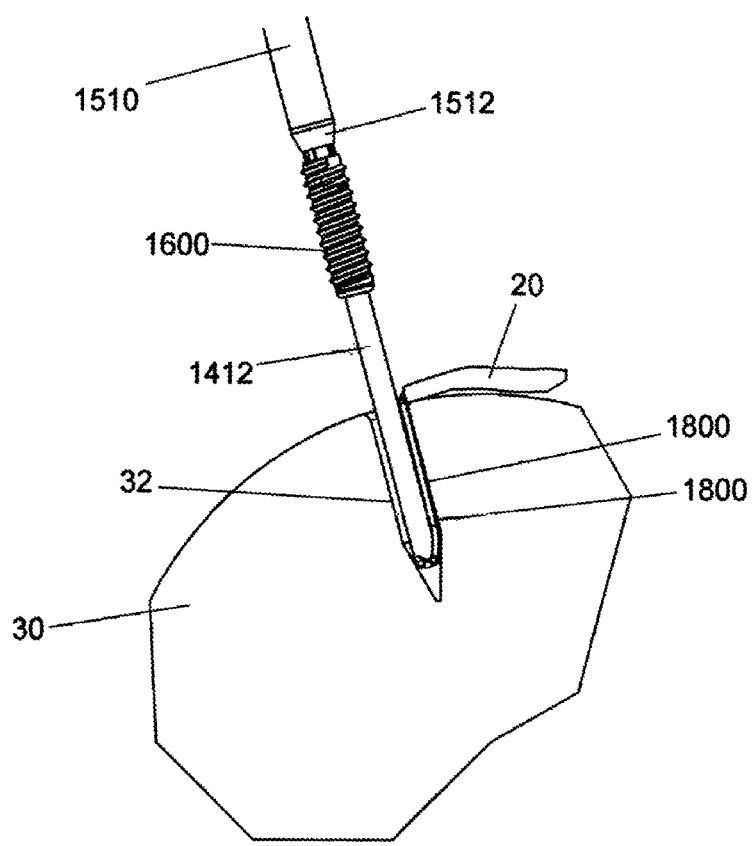
FIG. 28 depicts the distal portion of the first embodiment implant placement system during the second step of implant placement.
Figure 29:
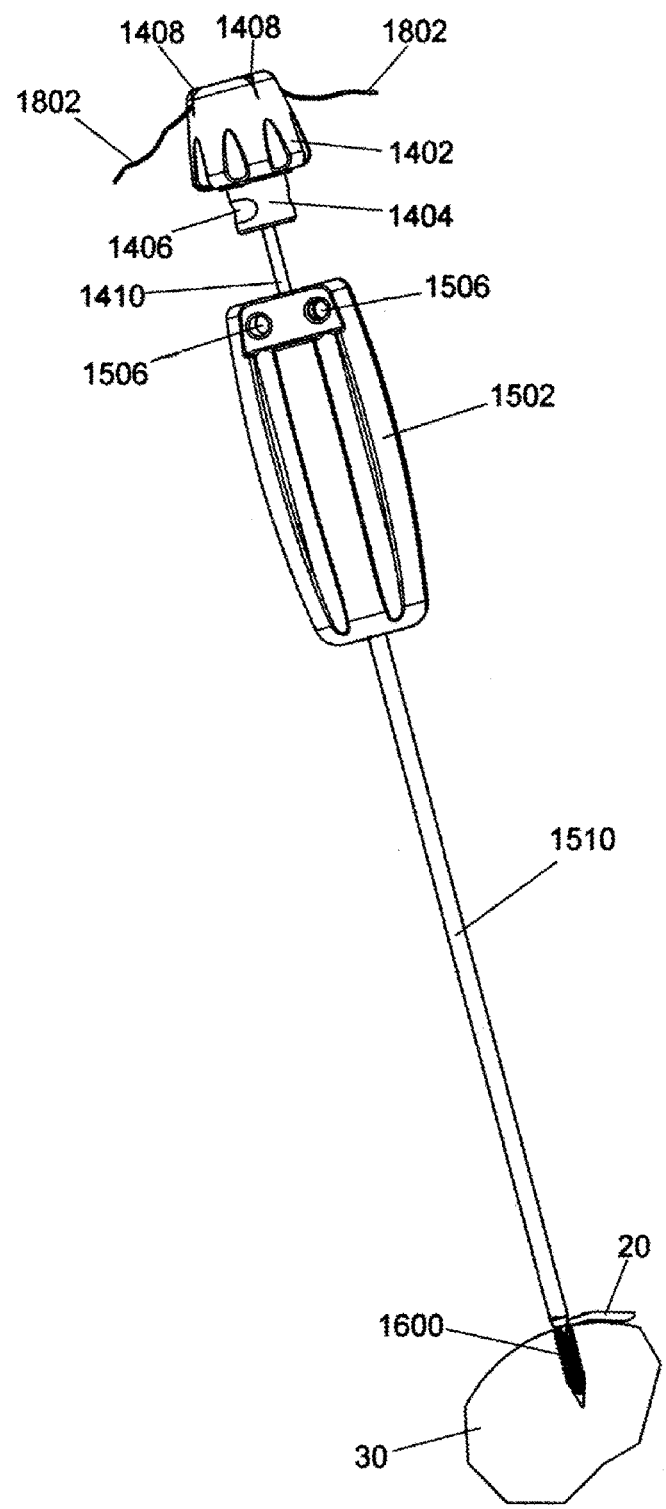
FIG. 29 depicts the first embodiment implant placement system positioned for the third step of implant placement.
Figure 30:
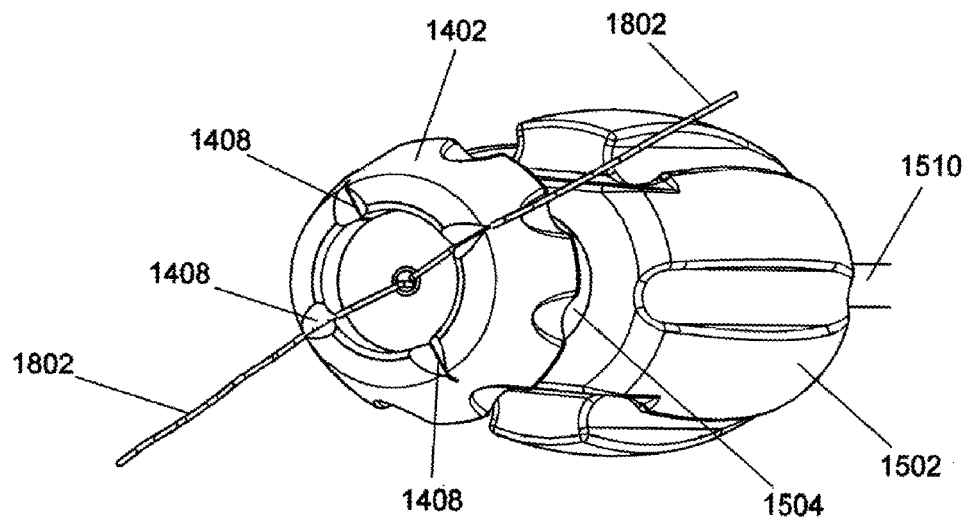
FIG. 30 depicts the proximal portion of the first embodiment implant placement system during the second step of implant placement.
Figure 31:
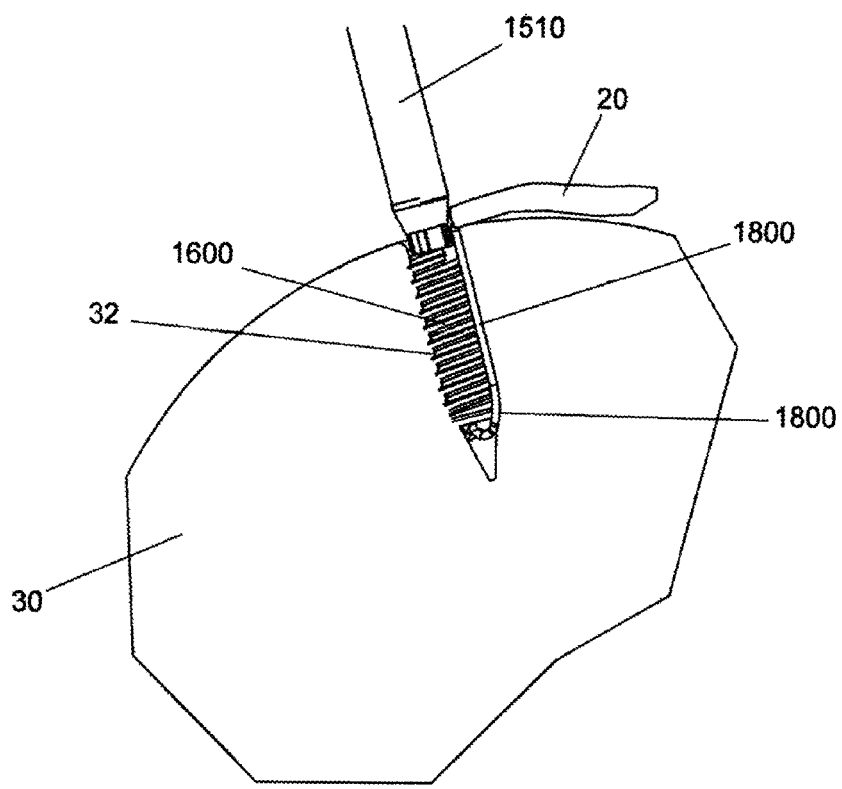
FIG. 31 depicts the distal portion of the first embodiment implant placement system during the third step of implant placement.
Figure 32:
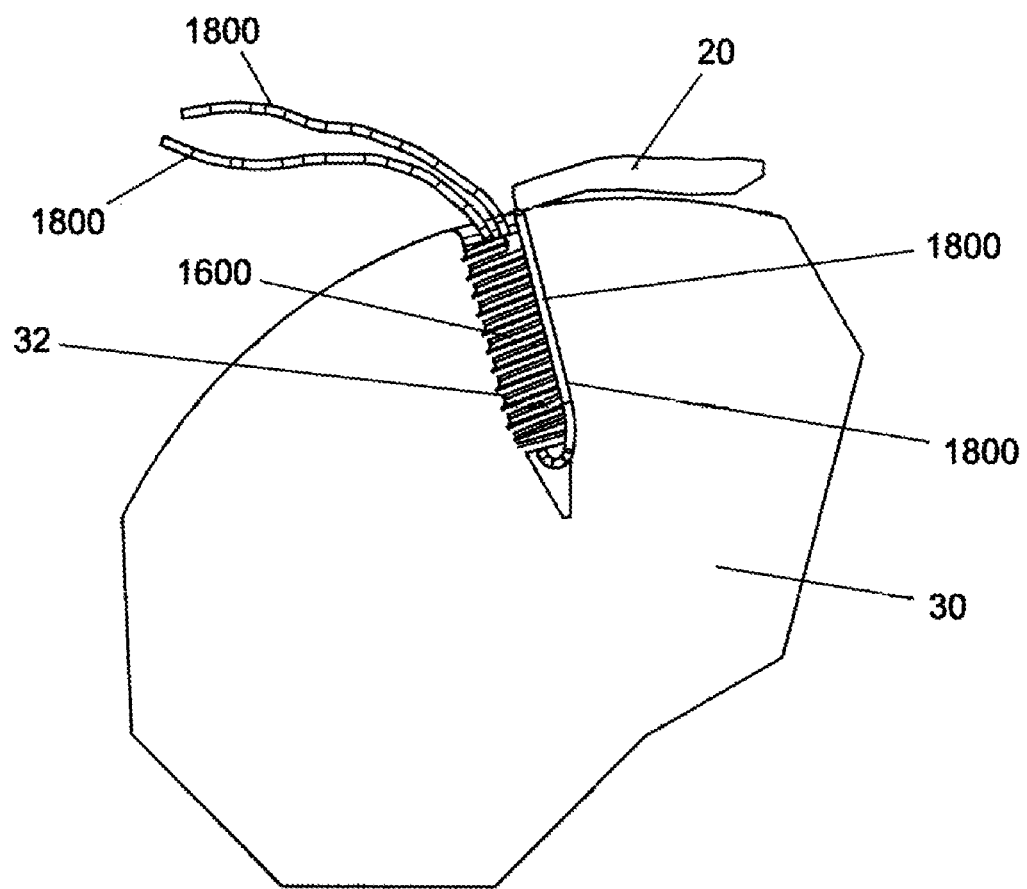
FIG. 32 depicts the site at the completion of implant placement using an implant placement system constructed in accordance with the instant invention.

The present invention may be used to secure any type of soft tissue, graft, or tendon, such as, for example, a biceps tendon or a rotator cuff. An illustrative method of fixation according to the principles of the instant invention is depicted in FIGS. 22 through 32. FIG. 22A schematically depicts a socket 32 formed by drilling or punching in bone 30, and a graft 20 to be affixed to bone 30. Sutures 1800 are passed through graft 20 in a usual manner; and the sutures loaded into system 1000 as previously described and depicted in FIGS. 20 and 21, such that suture proximal ends 1802 are accessible to the surgeon. Subsequently, distal tubular portion 1412 of inner assembly 1400 is inserted into socket 32 as depicted in FIGS. 23 through 25, the distal end of tubular portion 1412 contacting the bottom surface of socket 32. Thereafter, referring to FIGS. 26 through 28, the surgeon grasps proximal ends 1802 of sutures 1800 and withdraws them proximally so as to advance graft 20 towards socket 32. When graft 20 is in the desired position, proximal ends 1802 of sutures 1800 are secured in cleats 1408 to maintain the graft position. So long as proximal ends 1802 of sutures 1800 remain securely cleated and the distal end of tubular element 1412 is maintained in contact with the bottom surface of socket 32, the position of graft 20 will not change. The surgeon may adjust sutures 1800 as required to achieve optimal placement of graft 20. When this optimal placement of graft 20 has been achieved, while maintaining contact between the distal end off distal tubular element 1412 and the bottom of socket 32, the surgeon removes key 1200 from system 1000 so as to allow axial and rotational movement of outer assembly 1500. The surgeon then advances anchor 1600 to socket 32 and screws the anchor into socket 32 so as to trap sutures 1800 between anchor 1600 and the wall of socket 32 in bone 30 as depicted in FIGS. 29 through 31. When anchor 1600 is fully inserted in socket 32, proximal ends 1802 of sutures 1800 are released from cleats 1408 and system 1000 is withdrawn from the joint, leaving the repair site as depicted in FIG. 32. Subsequently sutures 1800 are cut adjacent to anchor 1600 and the anchor placement is complete.

Figure 33:
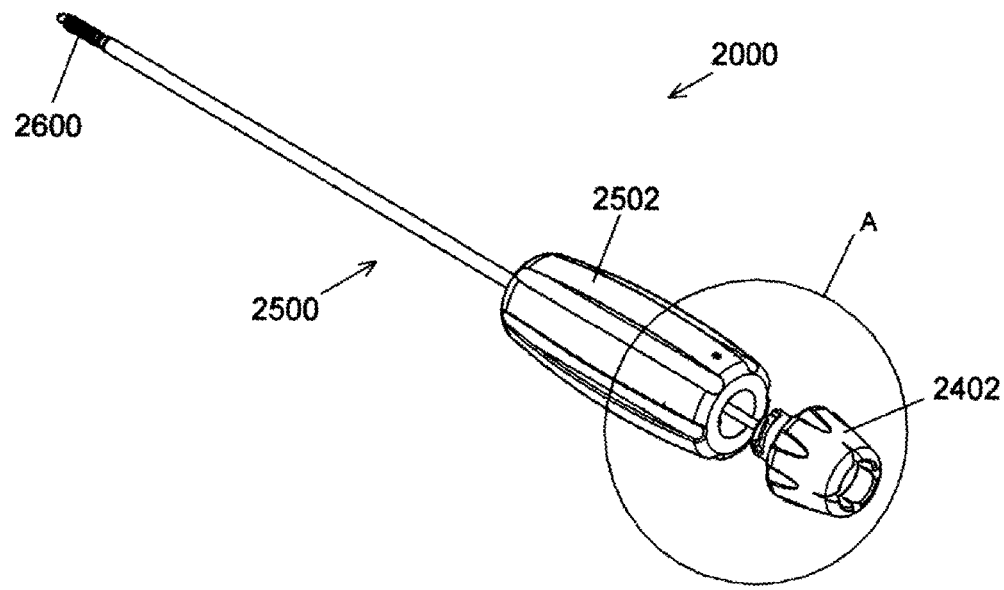
FIG. 33 is a perspective view of a second embodiment of an implant placement system constructed in accordance with the instant invention.
Figure 34:
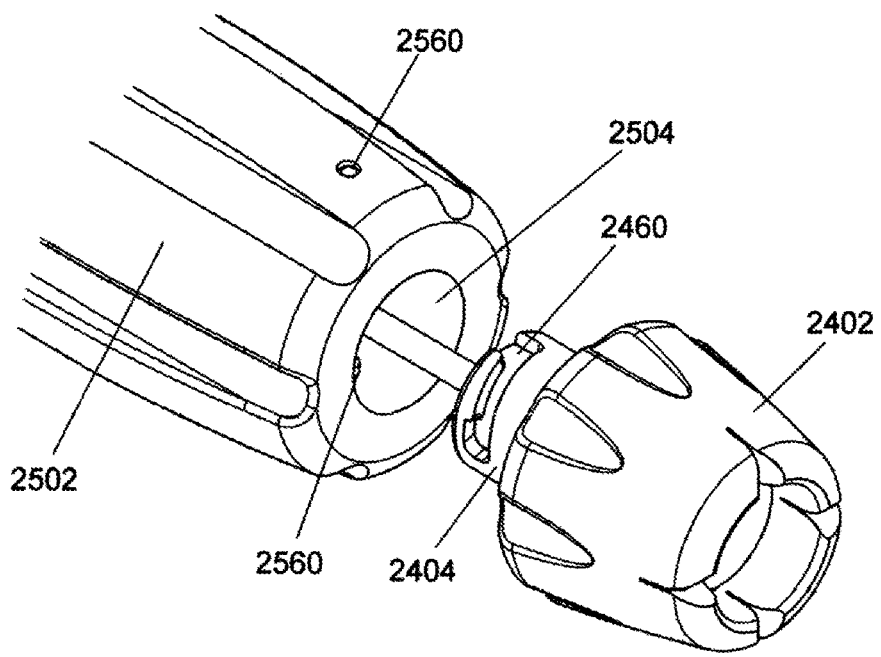
FIG. 34 is an expanded view of the objects of FIG. 33 at location A.
Figure 37:
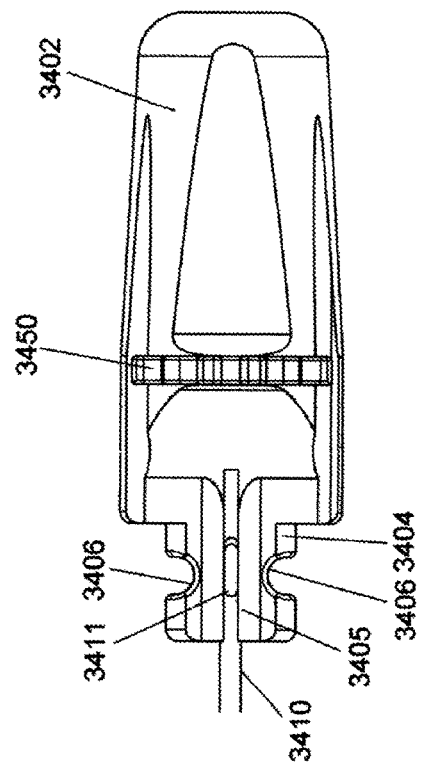
FIG. 37 is an expanded view of the proximal handle portion of the objects of FIG. 35.
Figure 39:
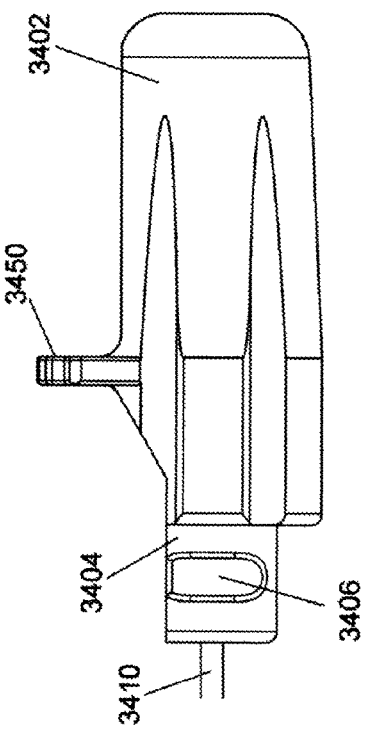
FIG. 39 is an expanded view of the proximal handle portion of the objects of FIG. 36.
Figure 38:
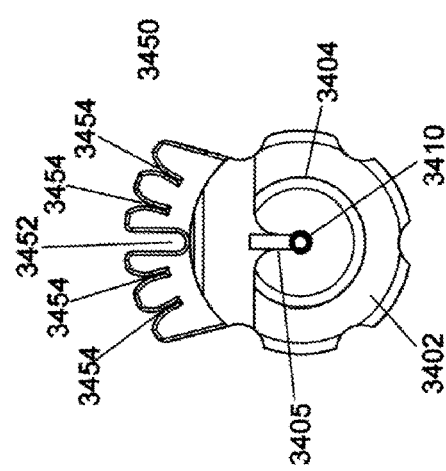
FIG. 38 is an expanded axial view of the objects of FIG. 35.
Figure 40:
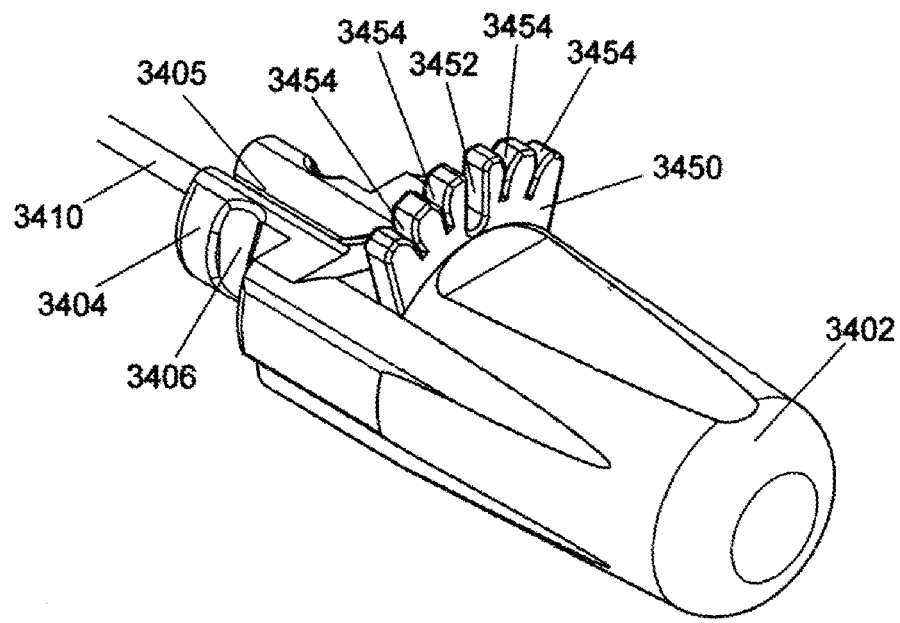
FIG. 40 is an expanded proximal perspective view of the proximal handle portion of the objects of FIG. 35.
Figure 41:
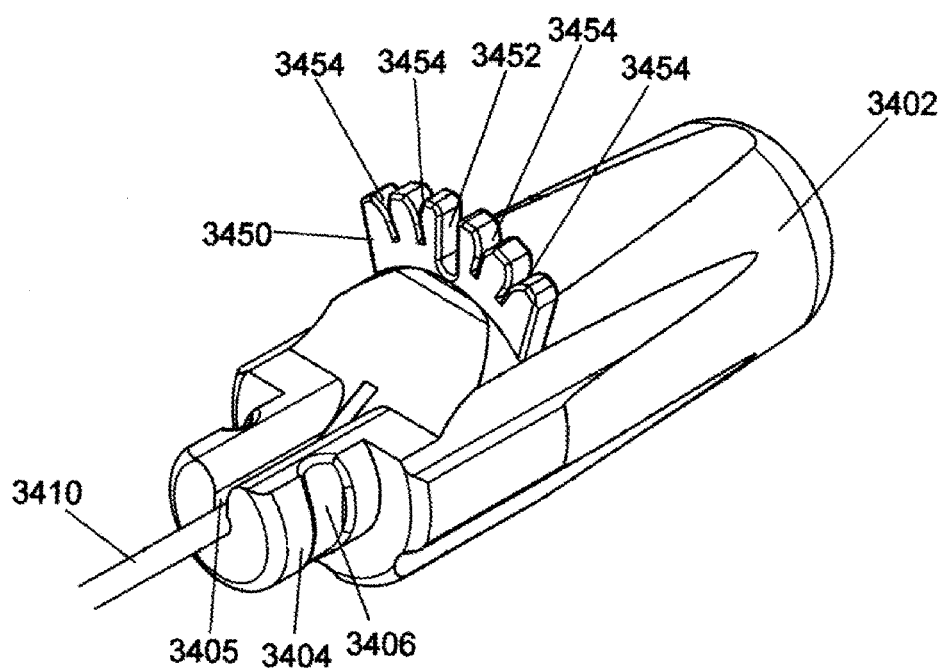
FIG. 41 is an expanded distal perspective view of the proximal handle portion of the objects of FIG. 35.

FIGS. 33 and 34 depict an alternate embodiment knotless anchor placement system 2000 constructed in accordance with the principles of the instant invention. Distal cylindrical portion 2404 of proximal hub 2402 of insertion device 2400 has formed therein shaped recesses 2460. Proximal cylindrical recess 2504 of proximal handle 2502 of outer driver assembly 2500 has protruding therein radially positioned pins 2560 sized and configured to cooperatively with shaped recesses 2460 limit axial and rotational motion of insertion device 2400 relative to driver 2500 when insertion device 2400 is assembled to driver device 2500 as when tensioning sutures in preparation for placement of anchor 2600. Rotating handle 2502 of driver 2500 clockwise relative to handle 2402 of insertion device 2400 allows driver 2500 to move axially and rotationally relative to insertion device 2400 so as to allow anchor 2600 to be advanced to the prepared socket and then threaded into the socket. In all other aspects, knotless anchor system 2000 functions in the same manner as system 1000.

In previous embodiments herein described, sutures are drawn through the central lumen of the insertion device and tension on the suture is maintained using cleats in the proximal rim of the insertion handle. While this allows a very simple construction, it places the tensioned sutures underneath the hand of the surgeon when using the device, and makes it necessary for the surgeon to change his grip on the insertion device handle when tensioning the sutures. This is particularly problematic when four sutures are being used with a single anchor. Also, because of the radial symmetry of the cleats, when four sutures are used with a single anchor, it may be problematic for the surgeon to identify which proximal end suture corresponds with a given passed suture viewed through the arthroscope.

The following preferred embodiment addressed these deficiencies by allowing the sutures to be maintained in a linear arrangement.

As seen in FIGS. 35 through 40, inner assembly 3400 has a proximal handle 3402 configured to overcome these deficiencies by retaining the sutures not in cleats in the proximal rim of the insertion handle, but in cleats in a flange 3450 positioned in the mid-region of handle 3402. The construction and functioning of inner assembly 3400 is like that of inner assembly 2400 in all aspects except as described hereafter, with like numbered features of the two devices functioning in the same manner. Flange 3450 has formed therein central slot 3452 configured to receive the distal cylindrical portion of the polymeric proximal pull tab 3306 of loading loop 3300, and suture cleats 3454. Distal cylindrical portion 3404 has formed therein slot 3405, which is configured to allow sutures exiting from opening 3411 of insertion tubular member 3410 to be retained in cleats 3454.

Figure 42:
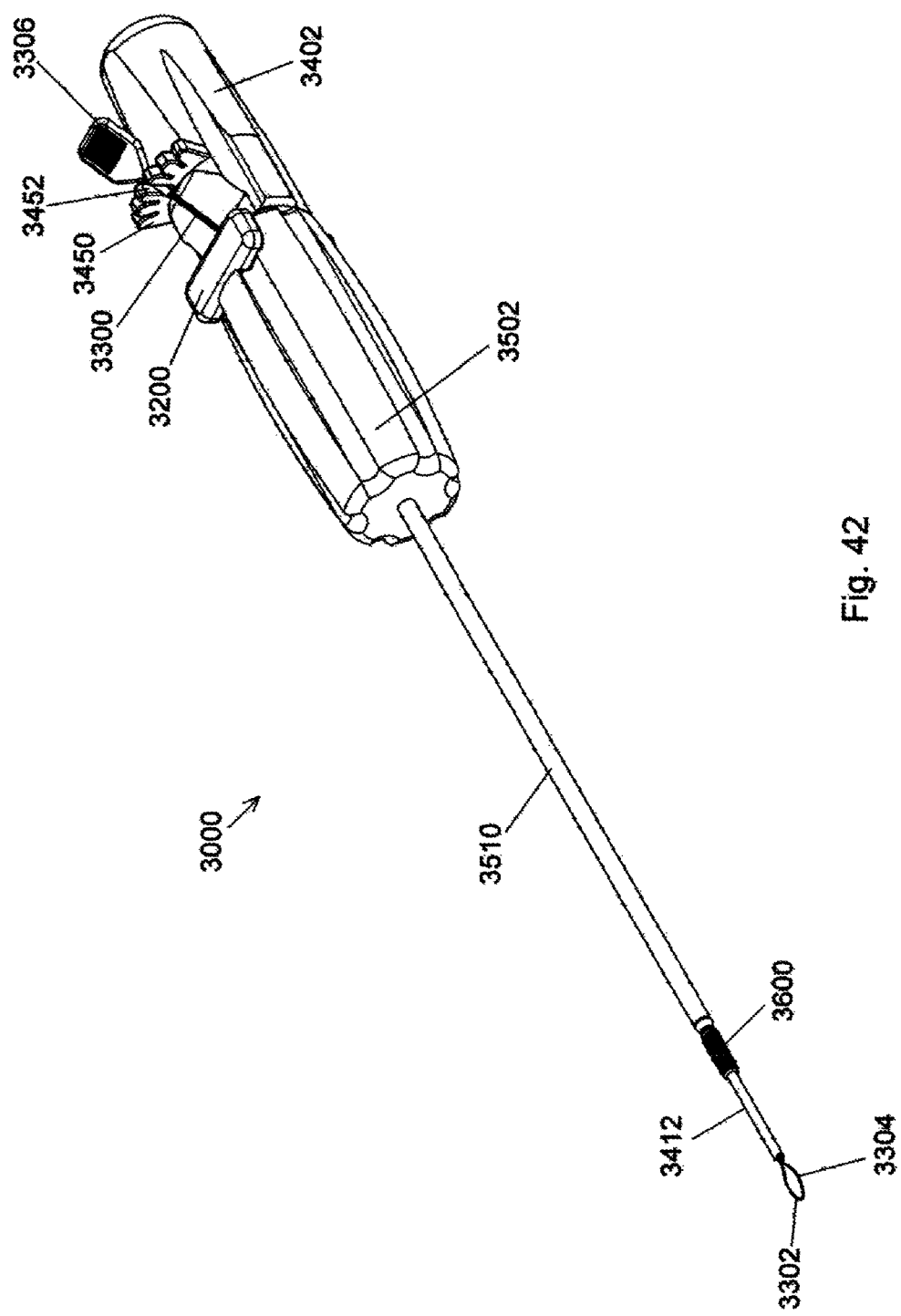
FIG. 42 is a perspective view of a third embodiment implant placement system constructed in accordance with the instant invention.

FIG. 42 depicts knotless suture placement system 3000 assembled and ready for use. Inner assembly 3400 is positioned within outer assembly 3500 with key 3200 maintaining axial and angular alignment between the devices. Anchor 3600 is loaded on distal drive element 3512. Loading loop 3300 is positioned within inner assembly 3400 with proximal pull-tab 3306 positioned within slot 3452 of flange 3450 of handle 3402.

Figure 43:
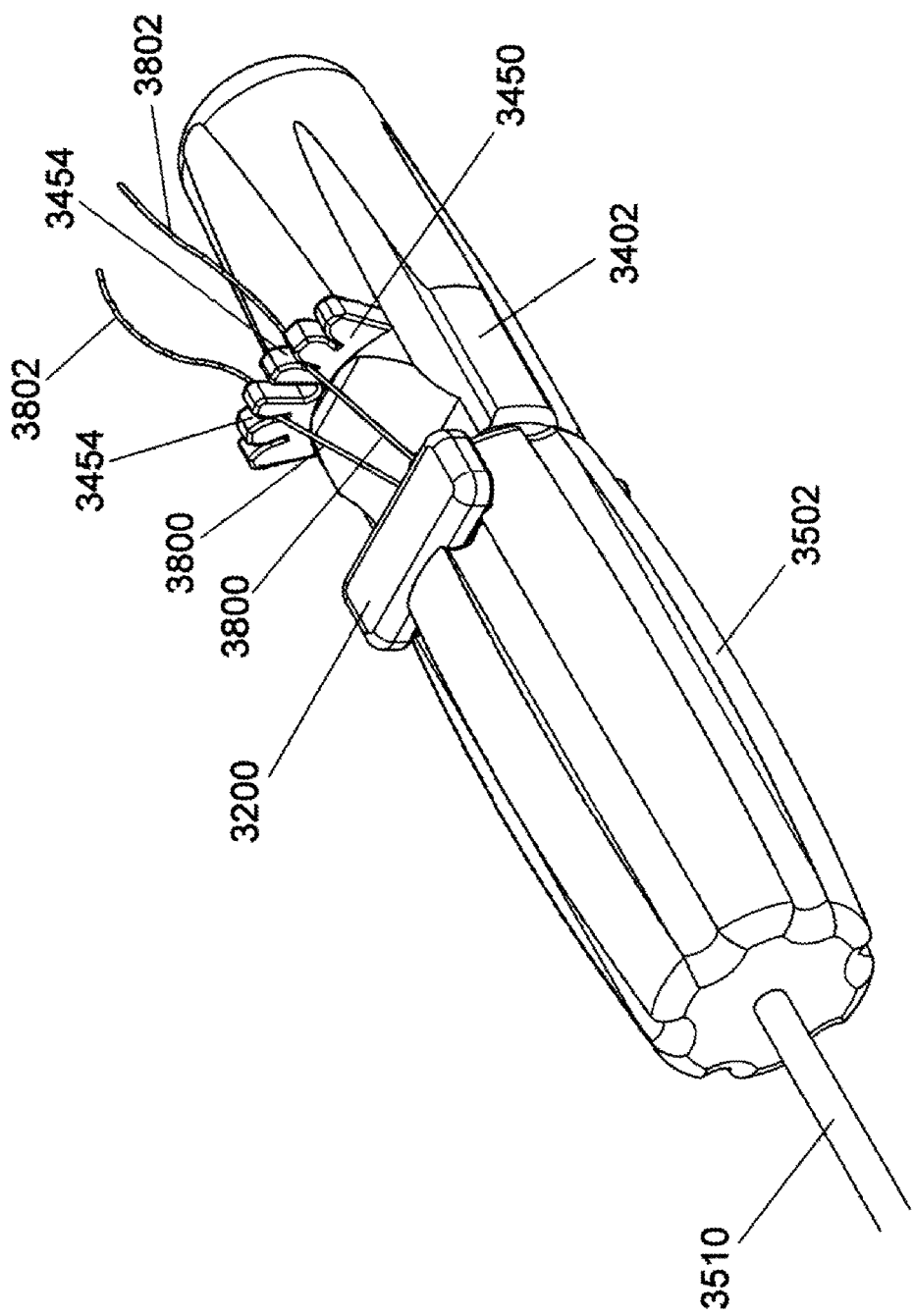
FIG. 43 is an expanded view of the proximal portion of the implant system of FIG. 42.
Figure 44:
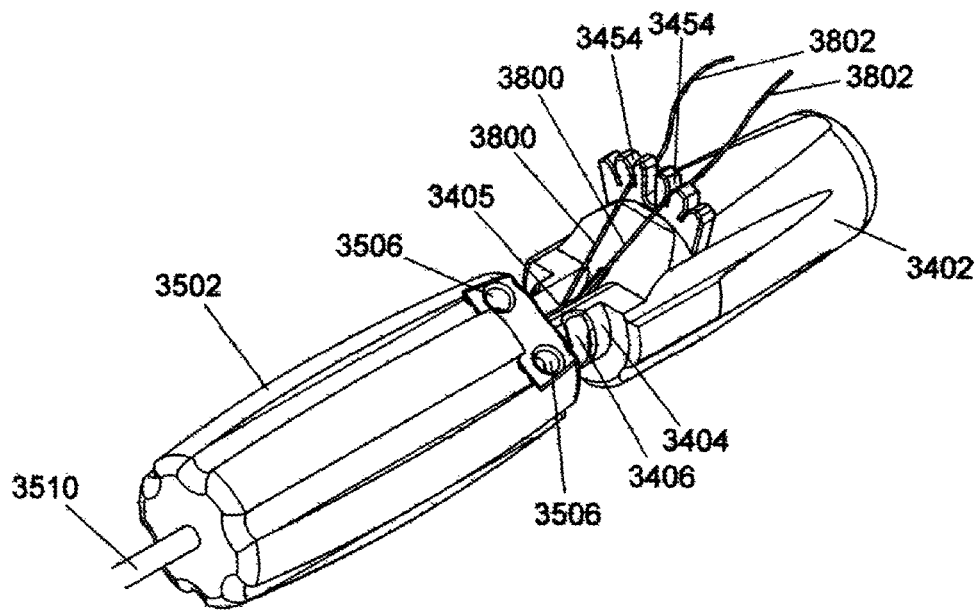
FIG. 44 is a distal perspective view of the third embodiment implant placement system of the instant invention positioned for the third step of implant placement.
Figure 45:
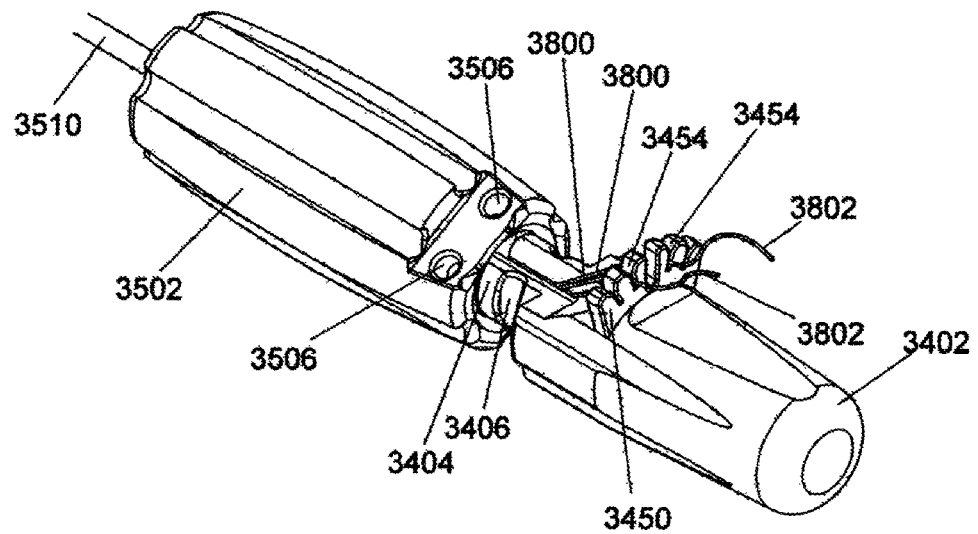
FIG. 45 is a proximal perspective view of the third embodiment implant placement system of the instant invention positioned for the third step of implant placement.
Figure 54:
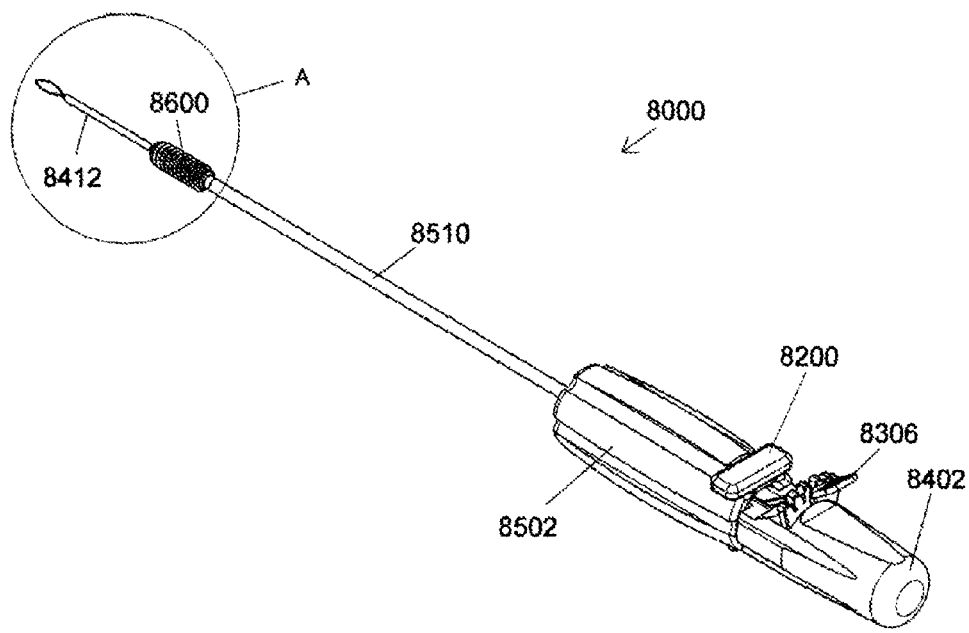
FIG. 54 is a perspective view of the objects of FIG. 51.
Figure 55:
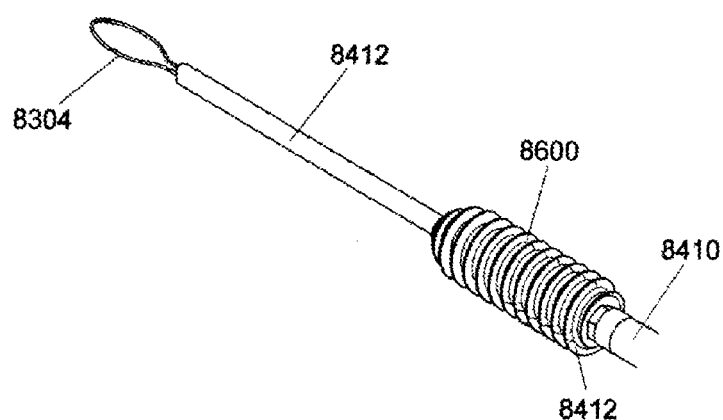
FIG. 55 is an expanded view of the objects of FIG. 51 at location A.

Operation of placement system 3000 proceeds in the same steps as when the previous embodiments are used. Suture is loaded into the system using loading loop 3300. Tensioning of the sutures is accomplished in the same manner except that the sutures are retained in slots 3454 of flange 3450 of handle 3402. FIG. 43 depicts proximal ends 3802 positioned within cleats 3454 as when tensioning of sutures 3800 is complete and graft 20 is properly positioned. In FIGS. 44 and 45, key 3200 has been removed to permit the outer assembly 3500 to be axially advanced and rotated so as to place anchor 3600 in prepared socket 32.

System 3000 has advantages over the systems 1000 and 2000. The size and configuration of handle 3402 and the placement of the cleats 3454 on flange 3450 rather than at the proximal end of handle 3402 allow the surgeon to conveniently and efficiently place distal end 3412 of insertion device 3400 in the prepared socket, to draw the graft to the proper position, and to remove key 3200 for advancement and placement of anchor 3600, all while maintaining control with a single hand position on handle 3402. When working with four sutures and a single anchor, the surgeon can arrange the sutures in cleats 3454 to match their position in the graft so as to minimize confusion and tangling of the sutures.

The anchor system of the instant invention may also be used for the placement of interference screws, that is for threaded implants in which tissue fixation is achieved through the trapping of tissue between the screw outer surface and the interior wall of the socket formed in the bone. Such interference screws are used as a fixation device for soft tissue grafts during ACL and PCL reconstruction procedures. Interference screws of the present invention are cannulated so as to allow the graft to be pulled into the socket by sutures attached thereto. An interference screw of the instant invention is depicted in FIGS. 46 through 50. Interference screw 8600 has a threaded exterior surface 8610, a distal cylindrical cannulation 8604 and a proximal interior drive portion 8602. Interference screw 8600 is depicted with a drive portion 8600 having a constant hexagonal cross-section. Other cross-sectional profiles may be used. For instance, the drive portion may have a cross-section that is a regular polygon, a spline, or slots formed in the interior wall. Any cross-section that allows the transmission of torque from a drive element to interference screw 8600 may be used. Similarly, while the cross-section of proximal drive portion 8602 is constant (as best seen in FIG. 49), the cross-section of the drive portion 8602 may be tapered or stepped so as to allow length 8606 of drive portion 8602 to be increased relative to length 8608 of interference screw 8600. Maximizing the length 8606 of proximal drive portion 8602 relative to anchor length 8608 is desirable so that torque is supplied to the distal portions of anchor 8600 by the driving element of the outer assembly rather than transmitted to the distal portions by the body of anchor 8600 as would be the case if length 8606 were shorter. Transmitting torque to the distal portions through the body of anchor 8606 may cause fracturing of anchor 8600 if the torque requirement exceeds the torsional strength of anchor 8606 at a location distal to the distal end of the driving element.

A placement system 8000 for affixing a graft to bone using interference screw 8600 is depicted in FIGS. 51 through 55. System 8000 is identical to system 3000 and functions identically to system 3000 except as specifically indicated herein. Distal portion 8514 of driving element 8512 has an extended length to match length 8606 of proximal driving portion 8602 of anchor 8600.

Figure 56:
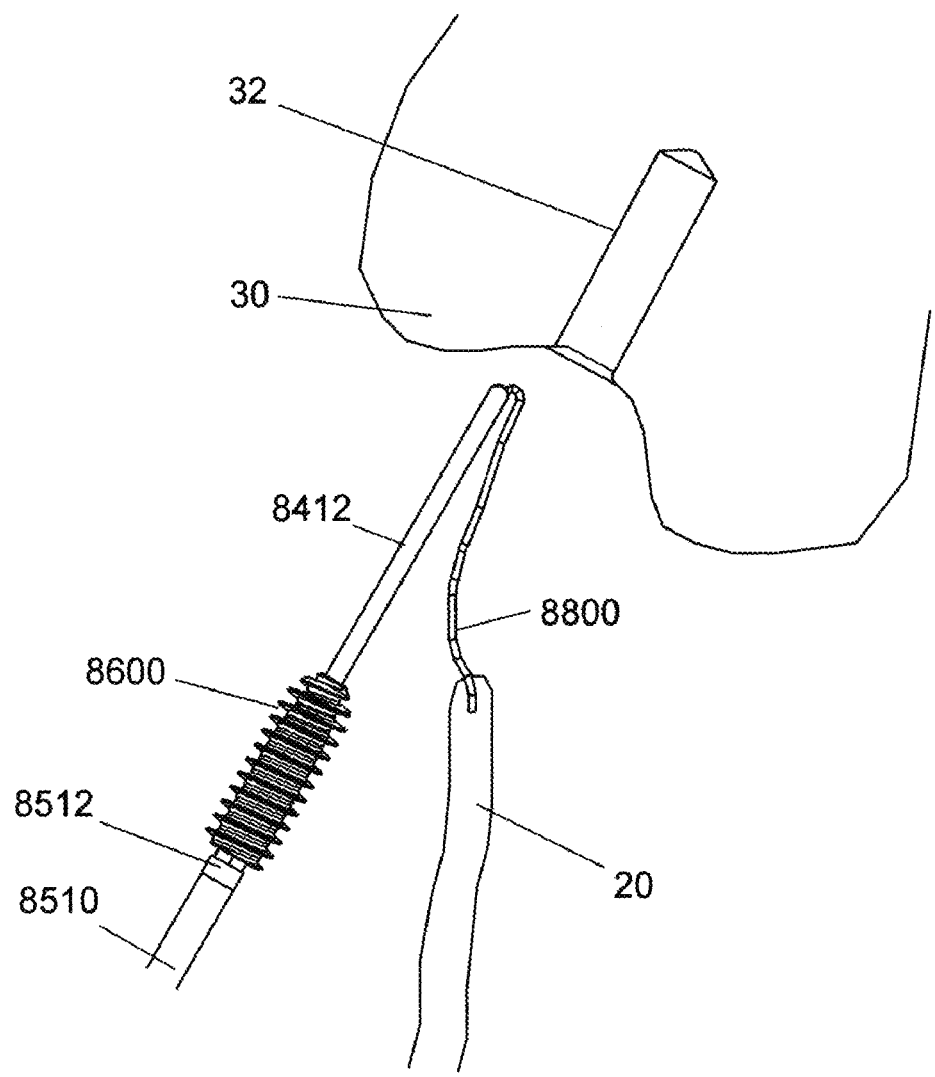
FIG. 56 is a schematic representation of a socket prepared in bone for securing of a graft using the interference screw of FIG. 46 and the placement system of FIG. 51.
Figure 57:
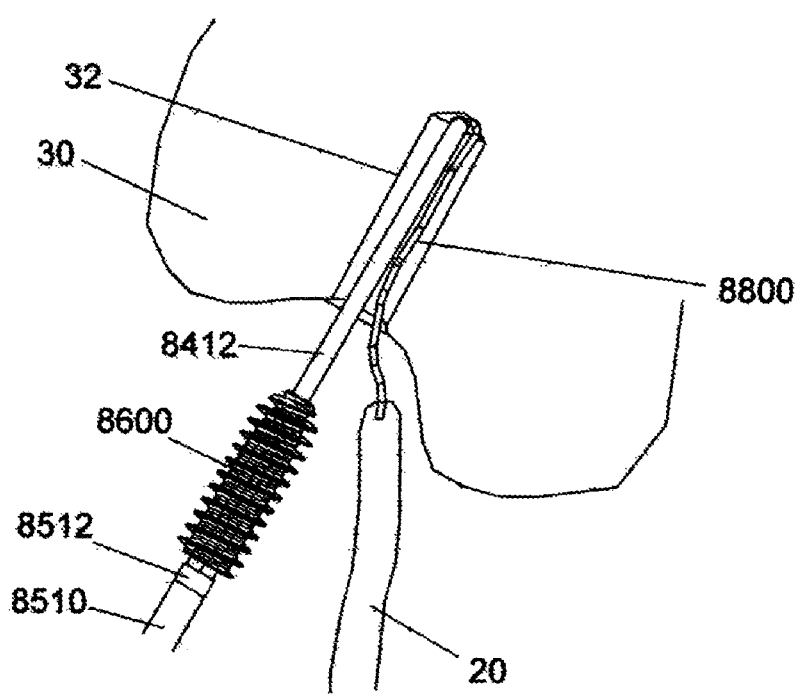
FIG. 57 depicts the first step in the placement of the interference screw.
Figure 58:
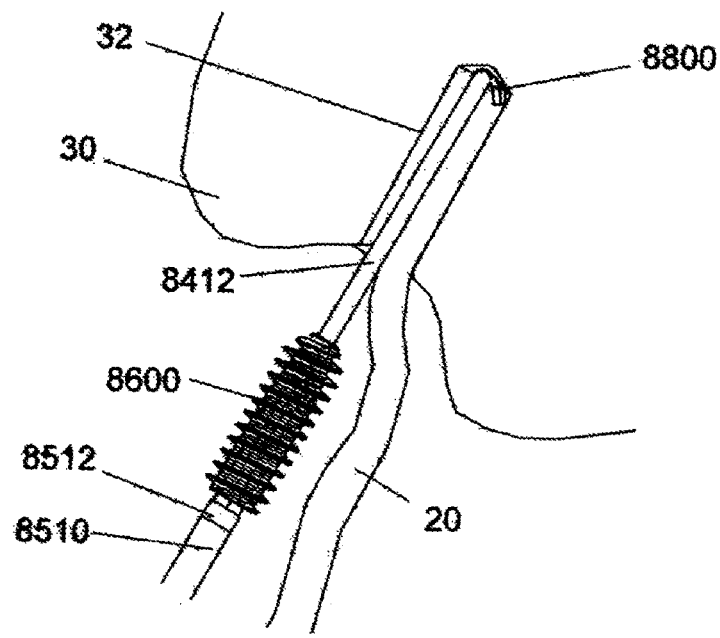
FIG. 58 depicts the second step in the placement of the interference screw.
Figure 59:
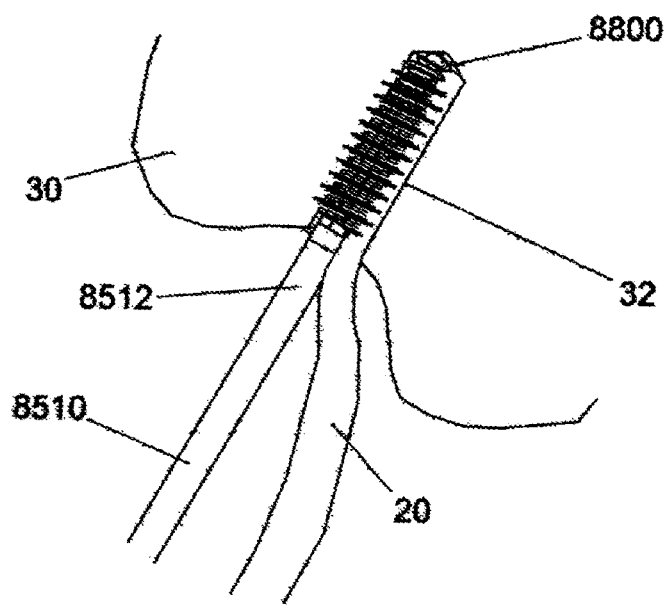
FIG. 59 depicts the third step in the placement of the interference screw.
Figure 60:
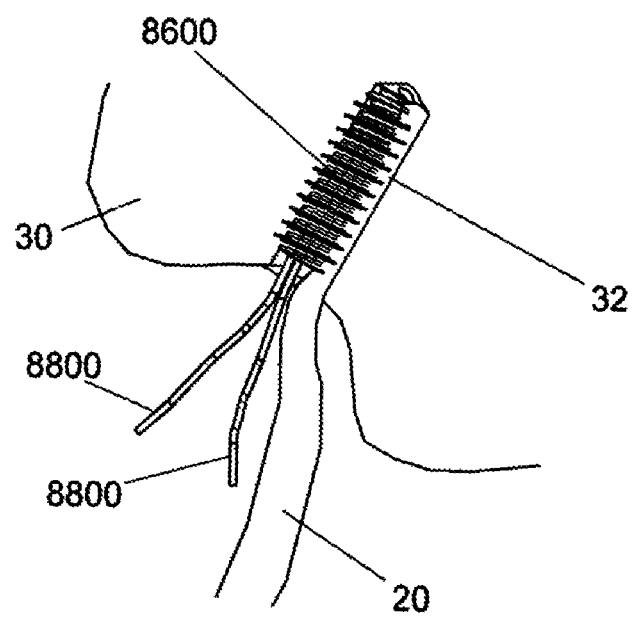
FIG. 60 depicts the site at the completion of the placement of the interference screw.

FIGS. 56 through 60 depict the affixing of graft 20 to bone 33 using placement system 8000. In the schematic representation of the figures, bone 30 is a femoral condyle in which socket 32 has been previously drilled to a predetermined depth and graft 20 is an ACL graft. Referring to FIG. 56, one or more sutures 8800 are passed through graft 20 in a conventional manner and loaded into placement system 8000 as previously herein described. Referring now to FIG. 57, the distal end of distal tubular element 8412 is inserted into socket 32 until the distal end of distal tubular element 8412 contacts the back wall of socket 32. By pulling on the proximal ends of sutures 1800, graft 20 is drawn into socket 32 until the distal end of graft 20 contacts the distal end of distal inner tubular member 8412 as shown in FIG. 58. The proximal ends of sutures 8800 are secured in cleats as previously herein described. Key 8200 is then removed from insertion system 8000 allowing interference screw 8600 to be advanced to socket 32 and then threaded into socket 32 as previously herein described thereby trapping graft 20 between screw 8600 and the sidewall of socket 32 as depicted in FIG. 59. Thereafter, sutures 1800 are released from their cleats and the inserter system 8000 is withdrawn leaving the graft secured in socket 32 by interference screw 8600 as depicted in FIG. 60. Subsequently sutures 8800 are trimmed proximal to anchor 8600.

Fixation of a graft in this manner using placement system 8000 has advantages over current conventional methods. For example, in a conventional ACL reconstruction, the graft is pulled into the socket by a suture extending through a hole drilled through the femur. When the graft is seated in the femoral socket an interference screw is placed in the socket thereby trapping the graft between the interference screw and the wall of the socket. During placement of the screw the screw may angularly deviate from the axis of the socket thereby decreasing the engagement between the screw, the graft and the socket wall. In such cases, the risk for graft slippage and failure of the fixation is increased. This deviation by the screw may be prevented by placement of a guide-pin over which the cannulated screw may travel; however, placement of this guide-pin is an added step and requires additional time.

Use of system 8000 in the manner previously herein described decreases the number of steps required for fixation of the femoral portion of the graft when doing, for instance, an ACL repair since the drilling of a hole through the femur and placement of sutures therein for drawing the graft into the socket is eliminated and axial alignment of anchor 8600 with socket 32 is maintained by distal inner tubular member 8412. The elimination of the need for drilling through the femur and drawing sutures there through for the purposes of drawing the graft into the femoral socket decreases the risk of iatrogenic injury. The risk of iatrogenic injury is due to the need to drill a passing pin or rod through the bone and exiting to the exterior of the limb puncturing the skin. In this manner the pin is pulled out through the skin, pulling the sutures into the femoral socket in order to pull the graft into place. The guide pin for a screw is then placed allowing for the placement of a screw over the guide pin, and said guide pin is then later removed. The guide pin is at risk for fracture and detachment and can become a loose body within the joint and has been observed in clinical practice. Furthermore, these same steps must be repeated for the tibia with placement of the guide pin into the tibial socket. System 8000 obviates this step and provides the risk of pin fracture to be eliminated as well as skin puncture and provides for accurate coaxial screw placement within these sockets. Fixation of soft tissue grafts using and interference screw

8600 and insertion system 8000 may be advantageously used for other procedures including biceps tenodesis and soft tissue tenodesis with distinct advantages over current methods. Conventional systems use either a forked tipped detachable eyelet or septated detachable eyelet to introduce a graft into a socket and advance the tendon and tip into a socket and then pull the screw into a socket by means of a reverse thread. In these cases, the graft can often be left outside the socket due to slippage of the graft from the tip or conversely the screw can be left partially outside the socket due to the end of the reverse thread being reached and the screw detaching from distal end of the introducer. Furthermore, in all cases the screw can detach from the introducer and not be properly positioned into the socket, thereby resulting in failure of the construct. The graft may also twist on insertion as well as the sutures resulting in over-tension of the construct and result in failure of fixation. Using screw inner tubular member 8412 the tenodesis construct can be placed by insertion of the inner member to the depth of the socket and the graft drawn into the socket. Alternatively, the graft can be pushed into the socket by means of the tip of 8412 and the system 8000 used to advance the screw 8000 to depth. Thereby ensuring the graft is not extruded from the socket, nor can the graft suture construct spins on the screw at the insertion socket. Finally the inner member 8412 can be used to direct the suture and graft into the depth of the socket. The screw 8600 can be disengaged from the assembly proximally and advanced to depth within the socket securing both the graft and suture which has been shown to provide additional graft security, without externalizing the screw or graft, and allowing the screw to be seated fully to depth, and ensuring no graft or suture spin of the construct resulting in loss of desired alignment or fixation of the graft/tissue/suture construct.

In the preceding embodiments (and other anchor/driver systems currently available), the anchor and driver are coaxial during placement of an anchor into a coaxial socket. In such instances, the socket is prepared using a drill or awl in which the distal socket-forming portion of the device is coaxial with the body of the device. However, the present inventors in U.S. Provisional Application Ser. No. 61/965,973 filed Feb. 13, 2014 (the entire contents of which are hereby incorporated by reference) describe a drilling device in which the distal portion may be angularly offset by the surgeon so as to produce holes having an axis offset from that of the more proximal portions of the drilling device. Using this device, it is possible to produce sockets for anchors in locations that cannot be accessed by drills or anchor driver systems in which the distal portion is not angularly offset. There is a need for an anchor system in which anchors may be placed in sockets in which the socket axis is not coaxial with the driving assembly axis. That is, in which the anchor and the distal portion of the driving assembly are coaxial with the socket, but the other portions of the driver assembly are not.

An alternate embodiment of the anchor system of the present invention has a driver assembly in which the surgeon is able to angularly offset the distal portion of the driver on which the anchor is loaded so as to allow coaxial placement in a socket that cannot be accessed by a driver assembly that is coaxial throughout its entire length. Device 4000 has an inner inserter assembly 4400 depicted in FIGS. 48 through 51, and an outer assembly 4500 depicted in FIGS. 61 through 64. Device 4000 is identical in construction and function to device 3000 except as described hereafter, and functions in the same manner as other embodiments previously herein described except as noted below.

Referring to FIGS. 48 through 51, inner inserter assembly 4400 is of identical construction to inner assembly 3400 (FIGS. 35 through 41) except that notches 4409 have been formed in the upper and lower surfaces of tubular member 4410 near its distal end as depicted.

Referring to FIGS. 65 through 67, outer driver assembly 4500 is identical to outer assembly 3500 except that tubular member 3510 has been replaced by an assembly consisting of proximal tubular member 4510, flexible tubular member 4509, and distal tubular member 4511. Flexible tubular member 4509 is capable of transmitting torque and axial force sufficient to thread an anchor into a prepared socket. In a preferred embodiment, flexible tubular member 4509 is of a layered construction of interwoven stainless steel wires. In other embodiments, flexible member 4509 is polymeric, while in still others it is a coupler made of layers of helically wound stainless steel sheet material. Any tubular flexible member capable of transmitting torque and axial force sufficient for anchor placement falls within the scope of this invention. Similarly, flexible tubular member 4509 may be affixed to proximal tubular member 4510 and distal tubular member 4511 by welding, brazing, soldering, adhesive bonding, mechanical fastening or any method suitable for use with the chosen material for tubular member 4511. So long as the joining method provides torque transmission and axial force transmission sufficient for placing an anchor in a prepared socket the method falls within the scope of this invention.

FIGS. 68 and 69 depict the elements of driver assembly 4000 prepared for assembly along with anchor 4600 which will be mounted to driving element 4512.

Figure 70:
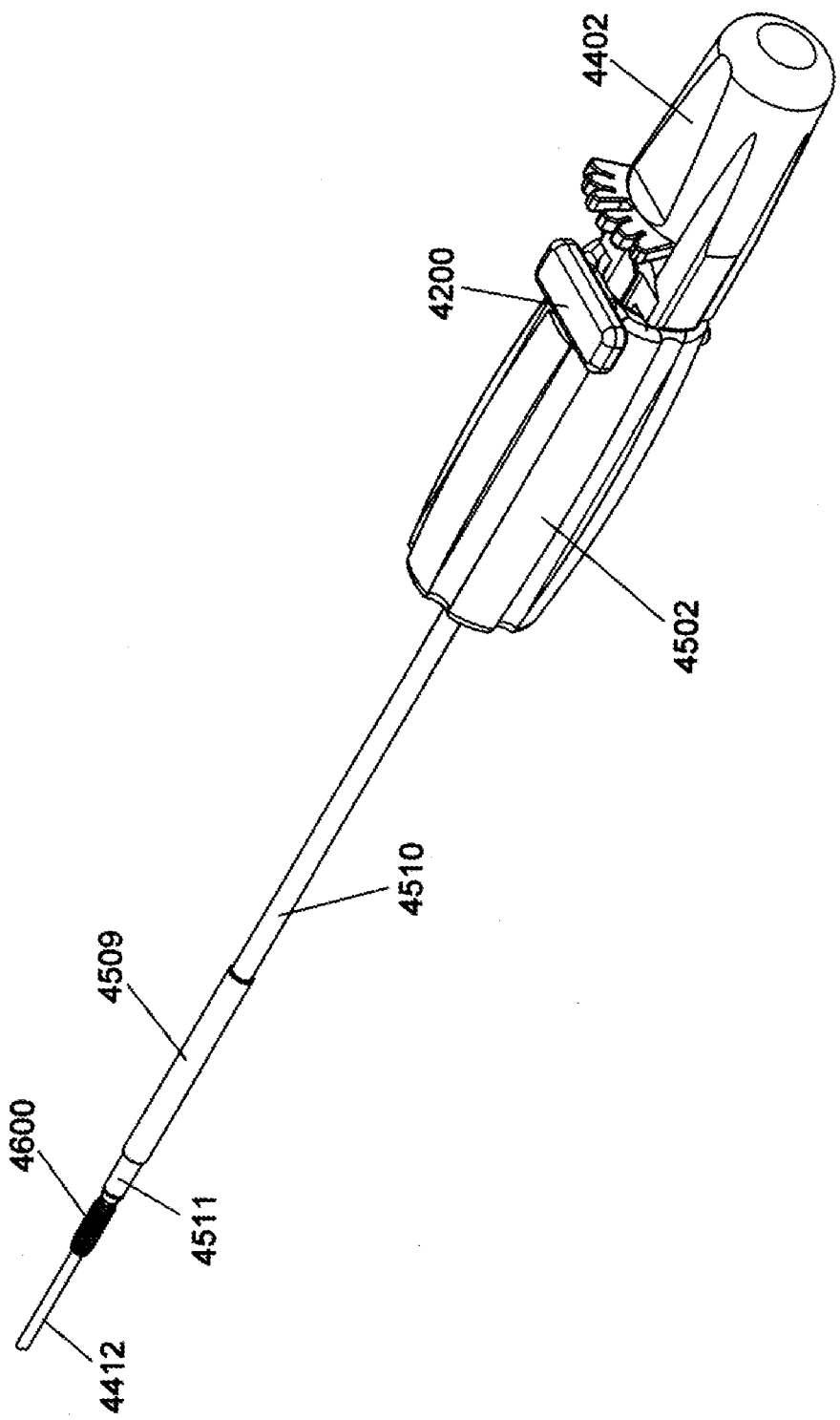
FIG. 70 is a perspective view of the fourth embodiment implant placement system assembled for use.
Figure 71:
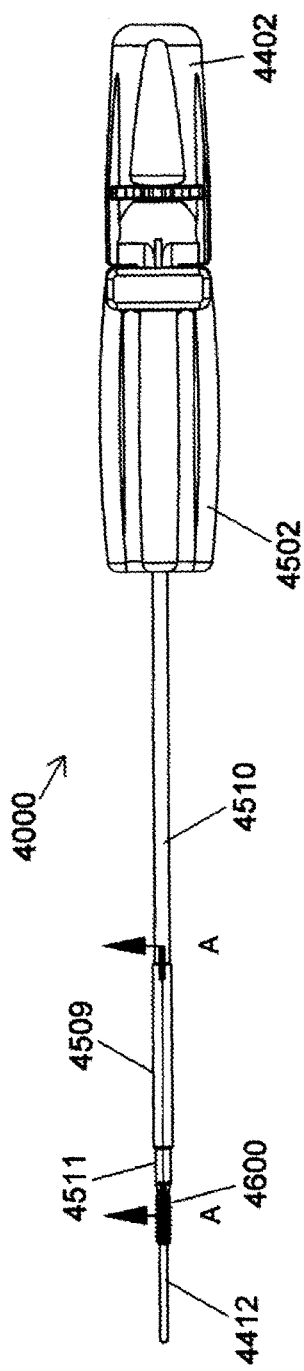
FIG. 71 is a plan view of the objects of FIG. 70.
Figure 72:
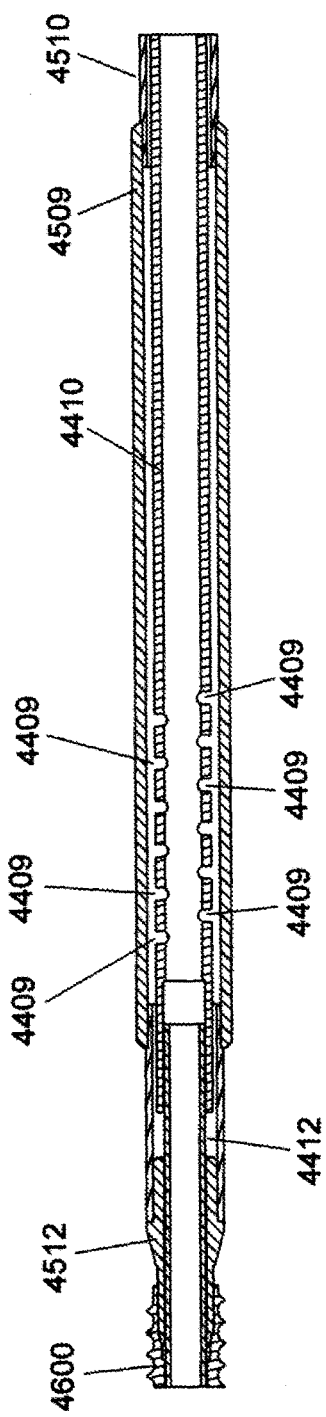
FIG. 72 is an expanded sectional view of the objects of FIG. 70 at location A-A.

As seen in FIGS. 70 through 72 depicting device 4000 assembled for use, notches 4409 formed in inner tubular member 4410 are axially positioned near the distal end of flexible tubular member 4509.

Figure 73:
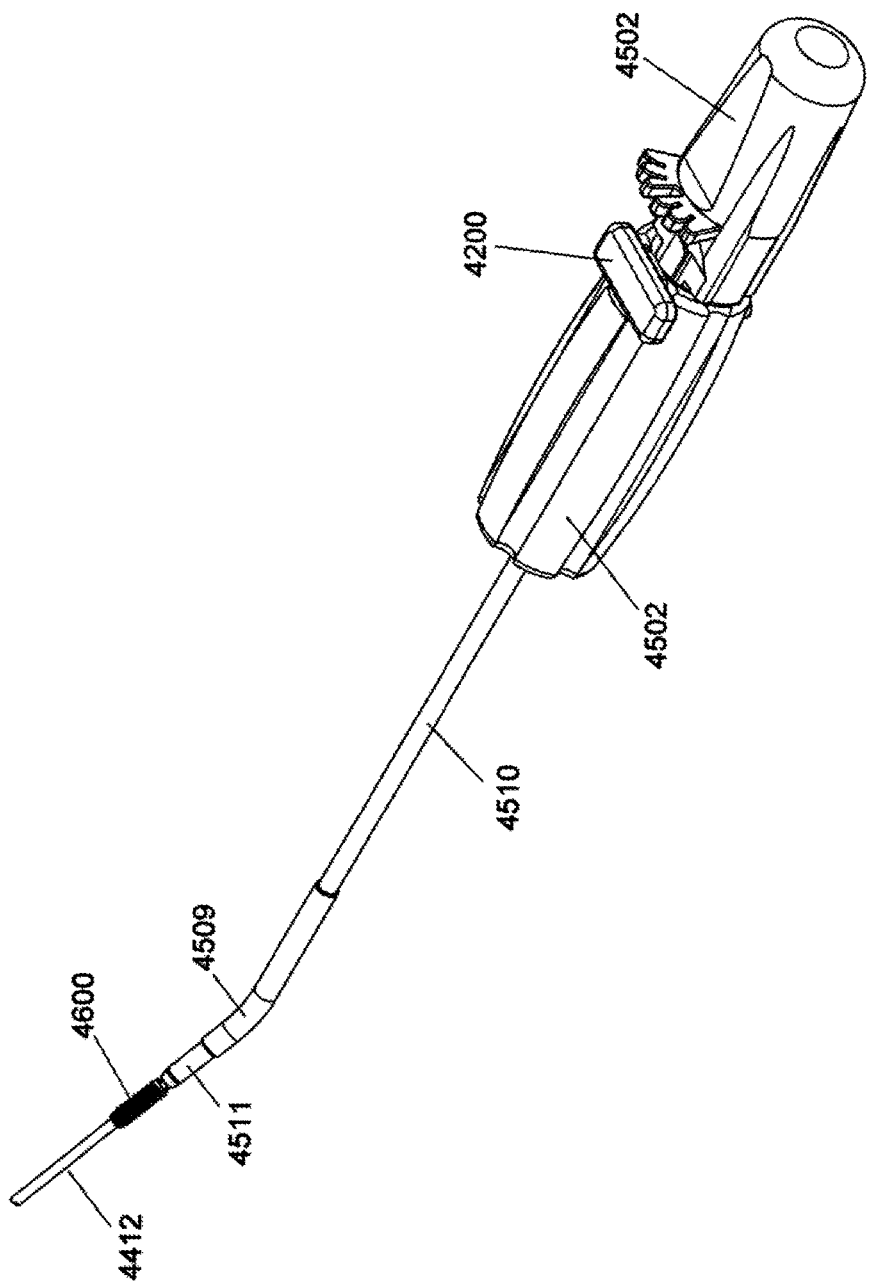
FIG. 73 is a perspective view of the fourth embodiment implant placement system with the distal portion angularly offset prior to use.
Figure 74:
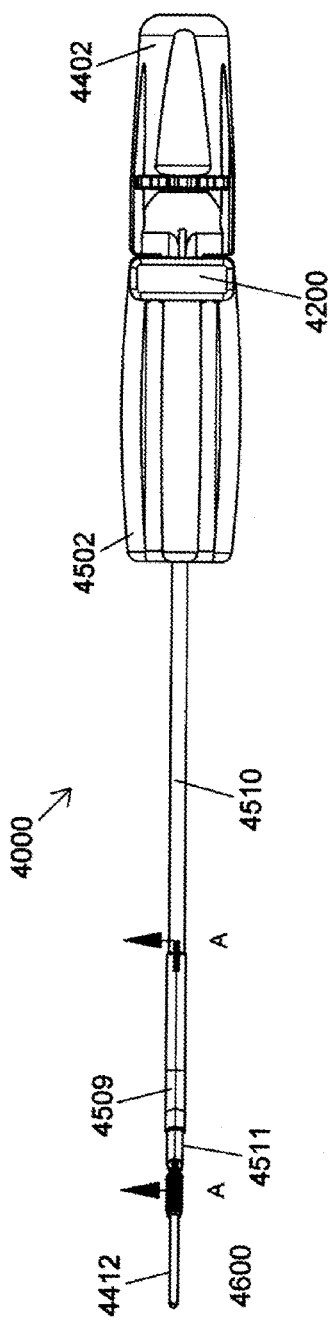
FIG. 74 is a plan view of the objects of FIG. 73.
Figure 75:
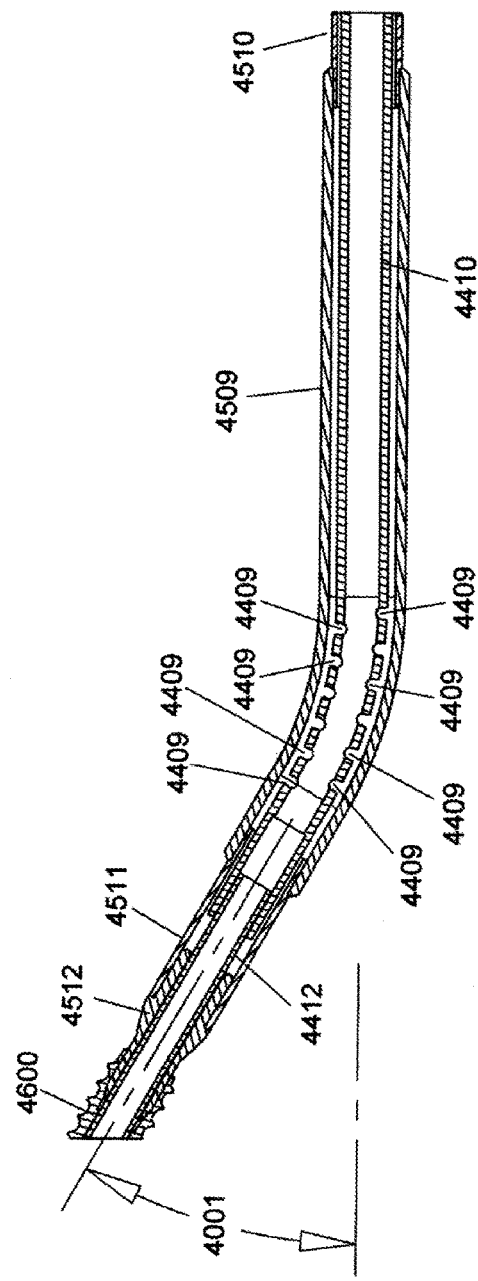
FIG. 75 is an expanded sectional view of the objects of FIG. 74 at location A-A.
Figure 80:
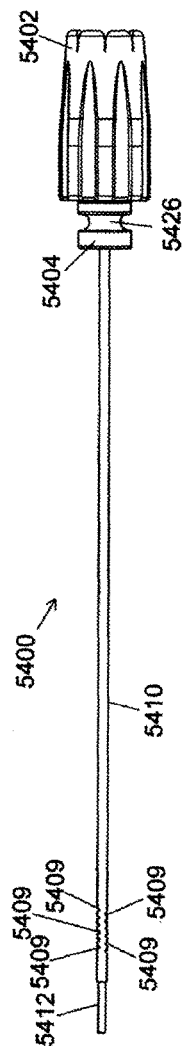
FIG. 80 is a plan view of the inner assembly of a fifth embodiment implant placement system constructed in accordance with the instant invention configured for placement of the anchor of FIG. 76.

In FIGS. 73 through 75, device 4000 is prepared for use in placing an anchor in a socket which cannot be coaxially accessed using a driver with a rigidly linear form, that is, wherein the distal insertion portion and distal driver portion of the device are coaxial with the axis of the proximal portions of the device. In preparation for tensioning of the sutures and placement of anchor 4600 the surgeon has axially offset the distal portion of device 4000 to angle 4001 using a bending device (not shown). As best seen in FIG. 75, the bend in inner tubular member 4410 is localized in the region of notches 4409 which have locally reduced the flexural strength of tubular member 4410 in the region for bending upwards or downwards. Removal of key 4200 will allow outer assembly 4500 to be advanced axially to bring anchor 4600 to the socket and rotation of outer assembly 4500 will thread the anchor into the socket in the manner previously herein described. Flexible tubular member follows the path formed by inner tubular member 4410, and distal tubular member 4412 acting upon driver element 4512 and distal tubular member 4511.

Inner tubular member 4510 has its flexural strength locally reduced by notches 4509. In other embodiments the flexural strength is reduced by localized annealing of tubular member 4510, by reducing the wall thickness in the region, or by a combination of these methods such as described in co-pending U.S. application Ser. No. 14/635,266 filed Mar. 2, 2015, the contents of which are hereby incorporated by reference herein. Localized reduction of the inner tubular member flexural strength by any method falls within the scope of this invention.

Driver system 4000 may be advantageously used for placing an implant during ACL repair as previously described using driver system 8000. Indeed, when combined with drilling systems that are able to produce off-axis sockets, ACL repairs according to the principles of this invention may be accomplished with significantly less external drilling of the tibia and femur and dramatically decreased risk of iatrogenic injury.

Embodiments of the instant invention previously herein described are knotless anchors, that is, anchor systems in which suture which has been passed through the tissue graft are fastened to bone by the act of placing an anchor, the suture not being affixed to the anchor by knots. Under certain conditions, it is desirable to first place an anchor with preloaded suture and, after passing suture legs through the graft, secure the graft to the anchor by joining opposite legs of each suture by knot tying. Such anchors are well known in the art; however, such current anchor systems are able to place anchors only in sockets that can be accessed with an anchor driver in which the axis of the anchor is coaxial with the axis of the driver body. Accordingly, there is a need for an anchor placement system for conventional preloaded anchors in which the anchor axis and the axis of the distal portion of the driver may be angularly offset from the axis of the driver device proximal portions.

This need is addressed by an alternate embodiment anchor system 5000. Anchor system 5000 enables the placement of a conventional preloaded anchor in which the axis of the prepared socket may be angularly offset from the axis of the anchor driver assembly. Anchor 5600, depicted in FIGS. 76 through 79, is identical in form and function to anchors 1600, 3600 and 4600 except that anchor 5600 has formed within its lumen 5620 laterally extending portion 5622 with radiused distal surface 5624. Portion 5622 is configured such that suture may be inserted into proximal end 5626 of lumen 5620, wrapped around distal surface 5624 of lateral extending portion 5622 and threaded out through proximal end 5626 of lumen 5620 such that the suture is retained in anchor 5600 but can slide freely.

Referring now to FIGS. 80 through 83 depicting an inner assembly 5400 for an anchor driver assembly for placing anchor 5600 with preloaded suture in a prepared socket in which the socket is not coaxial with the body of driver 5000, inner assembly 5400 is identical to inner assembly 4400 (FIGS. 61 through 64) except that distal tubular element 5412 has a shorter length than distal tubular member 4412 (FIGS. 61 and 62). Also handle 5402 incorporates the following changes from handle 3402 and handle 4402: flange 3450 with cleats 3454 has been removed; handle 5402 has a cylindrical proximal recess 5430 forming a proximal rim 5432 in which are formed cleats 5434, and; off-axis grooves 3406 have been replaced by circumferential groove 5426.

Figure 84:
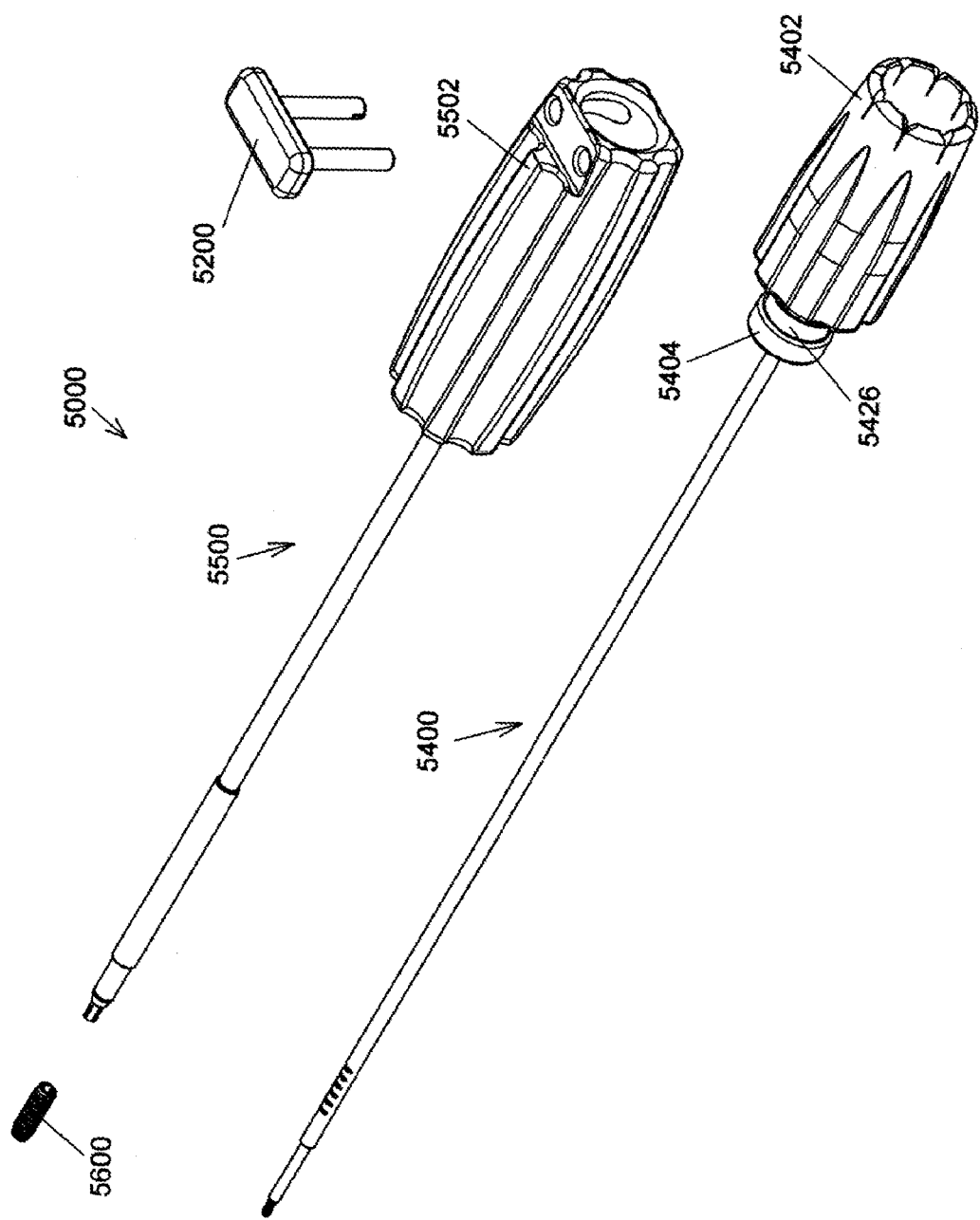
FIG. 84 is an exploded view of the assembly of the fifth embodiment implant placement system with the elements ready for assembly.
Figure 85:
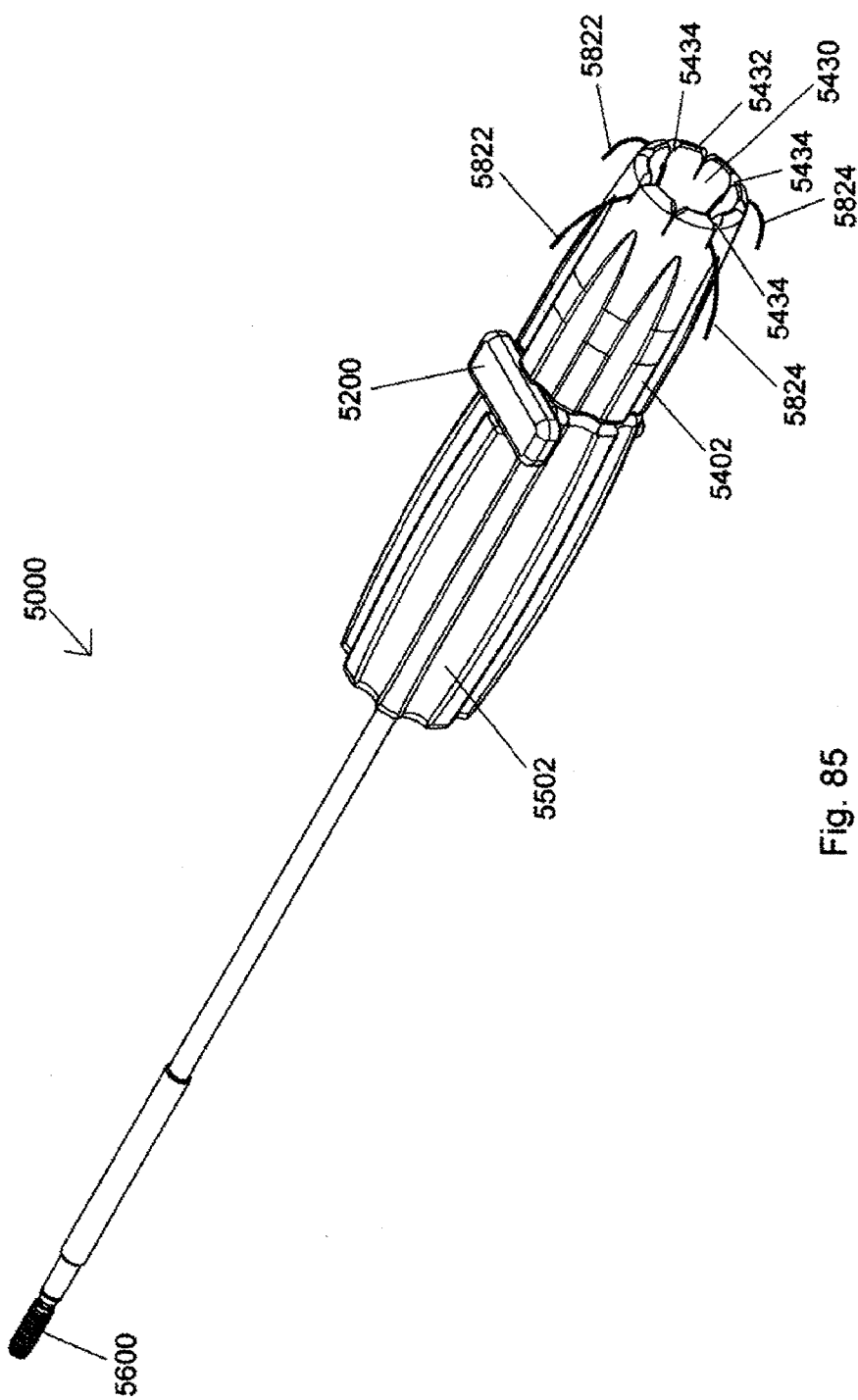
FIG. 85 is a perspective view of the fifth embodiment implant placement system.
Figure 89:
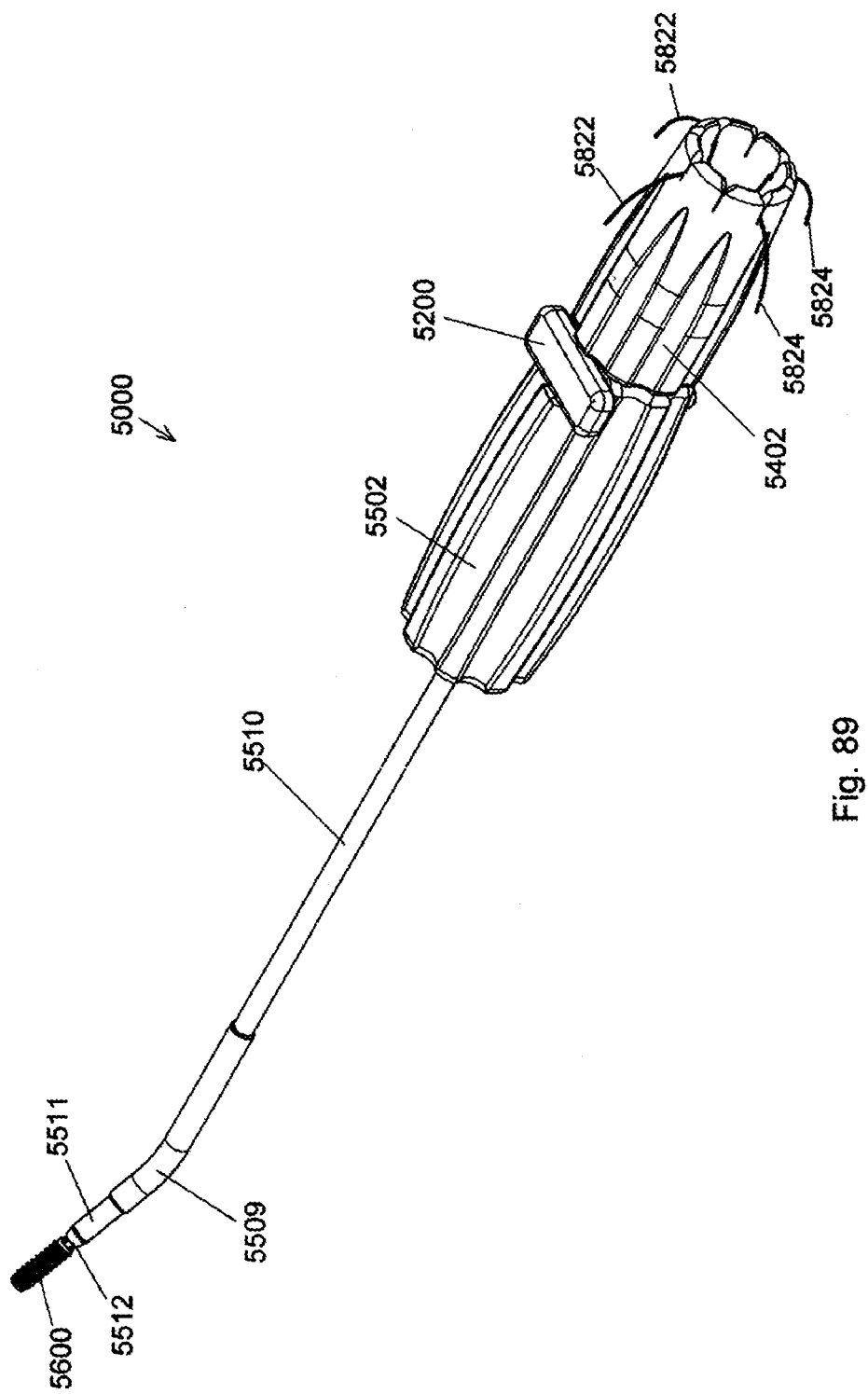
FIG. 89 is a perspective view of the fifth embodiment implant placement system with its distal portion angularly offset.
Figure 92:
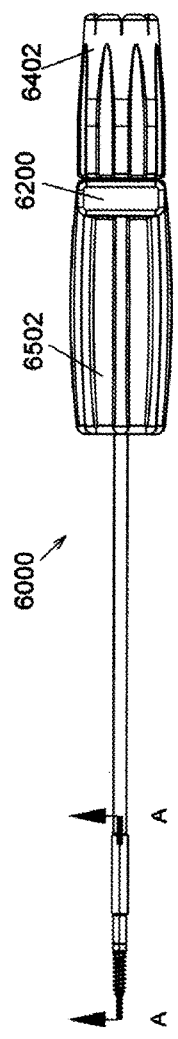
FIG. 92 is a plan view of the objects of FIG. 90.
Figure 93:
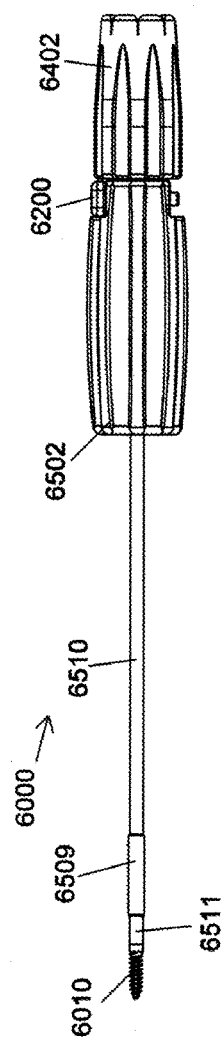
FIG. 93 is a side elevational view of the objects of FIG. 90.
Figure 94:
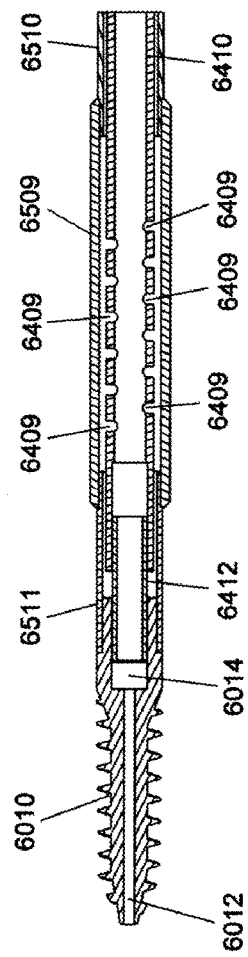
FIG. 94 is an expanded sectional view of the objects of FIG. 92 at location A-A.
Figure 97:
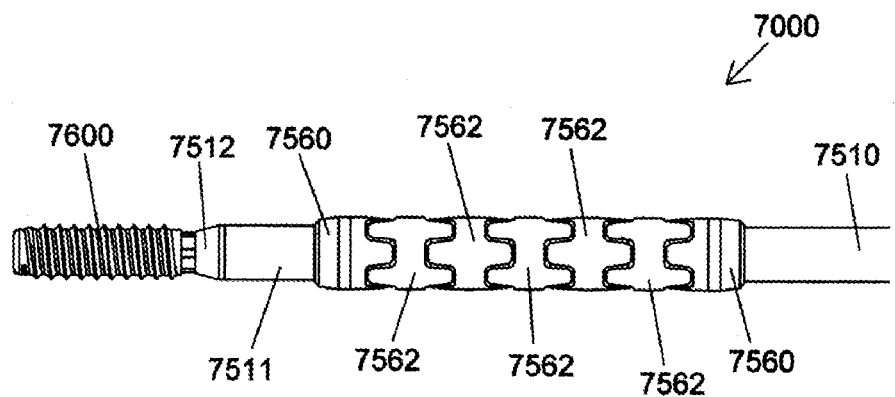
FIG. 97 depicts the distal portion of an alternate embodiment device formed in accordance with principles of the instant invention in which the distal portion is angularly offset from the more proximal portions of the device, and which transmits torque to the rotatable distal element through discreet torque transmitting elements.

FIG. 84 depicts inner assembly 5400, outer assembly 5500 (identical to outer assembly 4500 (FIGS. 65 through 67), key 5200 and anchor 5600 prepared for assembly. To assembly driver assembly 5000, inner assembly is inserted into outer assembly 5500 and key 5200 is inserted into outer handle 5502 in the manner previously herein described, sutures (generally two) are loaded into anchor 5600 such that the mid-point of each suture is wrapped around the proximal end 5624 of laterally extending portion 5622 of anchor 5600 with the suture tails extending from proximal end 5626 of lumen 5620. Using a loading loop (not shown) the sutures are drawn through distal tubular member 5412, tubular member 5410, and proximal cylindrical recess 5430 to the proximal end of handle 5402 of inner assembly 5400. While tension is applied to the suture tails, anchor 5600 is mounted to distal drive element 5512, distal tubular member 5412 being positioned within lumen 5620 of anchor 5600. The sutures are then cleated in cleats 5434 with the sutures under tension so as to retain anchor 5600 on distal drive element 5512 and distal tubular member 5412. In a preferred method, outer assembly 5500 and anchor 5600 mounted thereto are then rotated counter-clockwise a predetermined number of revolutions. The predetermined number of revolutions is the number of turns that are required to fully seat anchor 5600 in the socket with the proximal end recessed to a desired depth below the surface. By twisting the sutures in this manner when anchor 5600 is loaded, screwing the anchor into the socket will untwist the sutures so that when anchor 5600 is seated and driver 5000 withdrawn, the suture tails will not be twisted, or only moderately twisted. Portions of the suture tails extending proximally beyond cleats 5434 can be stored in proximal cylindrical recess 5430.

Conventional pre-loaded anchors are well known in the art, and anchor 5600 is an illustrative example only. Anchor system 5000 may be advantageously used with other conventional pre-loaded anchors. So long as the driver device assembly comprises a bendable non-rotating inner cannulated member through which sutures pass with the cannulated member having a region of locally reduced flexural strength for localization of the bend, and further comprises a rotating torque-transmitting element having a flexible region, the anchor placement system falls within the scope of this invention. It is not necessary that the anchor having a cannulation or a proximal cylindrical recess.

FIGS. 85 through 88 depict anchor system 5000 assembled and ready for use. Anchor 5600 is mounted to distal drive element 5512 and sutures 5822 and 5824 have been loaded to the anchor and the device, tensioned as previously described, and cleated in cleats 5434. Key 5200 engages circumferential groove 5426 in distal cylindrical portion 5404 of handle 5402 so that outer assembly 5500 can rotate freely about inner assembly 5400, but has a fixed axial position. Removal of key 5200 allows disassembly of driver system 5000 for cleaning and replacement of components as required. Key 5200 is not removed during anchor placement.

FIG. 86 depicts driver assembly 5000 with its distal portion angularly offset in preparation for anchor placement in a socket that is not accessible with a driver device without an angular distal offset.

In previous embodiments for placement of knotless anchors, distal tubular section 4412 protrudes beyond the distal end of the anchor and the anchor moves distally along distal tubular section 4412 during anchor placement. In the embodiment of driver device 5000, anchor 5600 does not move axially relative to distal tubular portion 5412, but rotates about it during insertion, distal tubular portion 5412 moving into the socket along with anchor 5600. When anchor placement is complete, sutures 5822 and 5824 are removed from cleats 5434 and device 5000 is withdrawn proximally leaving anchor 5600 in the socket with sutures 5822 and 5824 loaded to the anchor and slidably free.

Certain anchors because of their configuration and/or materials require that preparation of a socket for placement of an anchor therein includes the step of forming threads in the socket using a thread-forming device known as a tap. Taps currently in use are linearly-formed devices in which the distal thread-forming portion of the device is coaxial with the proximal torque-supplying portions of the device. Such tapping devices are incapable of forming threads in sockets which were of necessity formed with drilling devices having an axial offset between the drill and the proximal torque-supplying portion of the drilling device. There is a need for a tapping device having a distal thread-forming portion which may be angularly offset from the proximal torque-supplying portions of the device.

Figure 81:
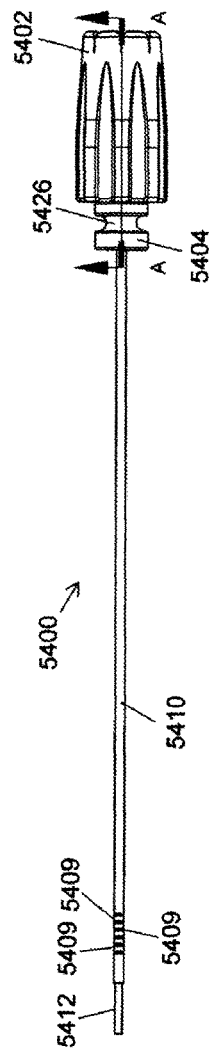
FIG. 81 is a side elevational view of the objects of FIG. 80.
Figure 82:
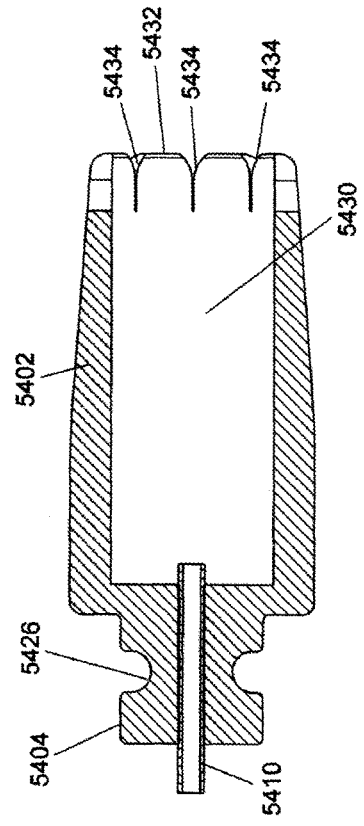
FIG. 82 is an expanded sectional view of the objects of FIG. 81 at location A-A.
Figure 83:
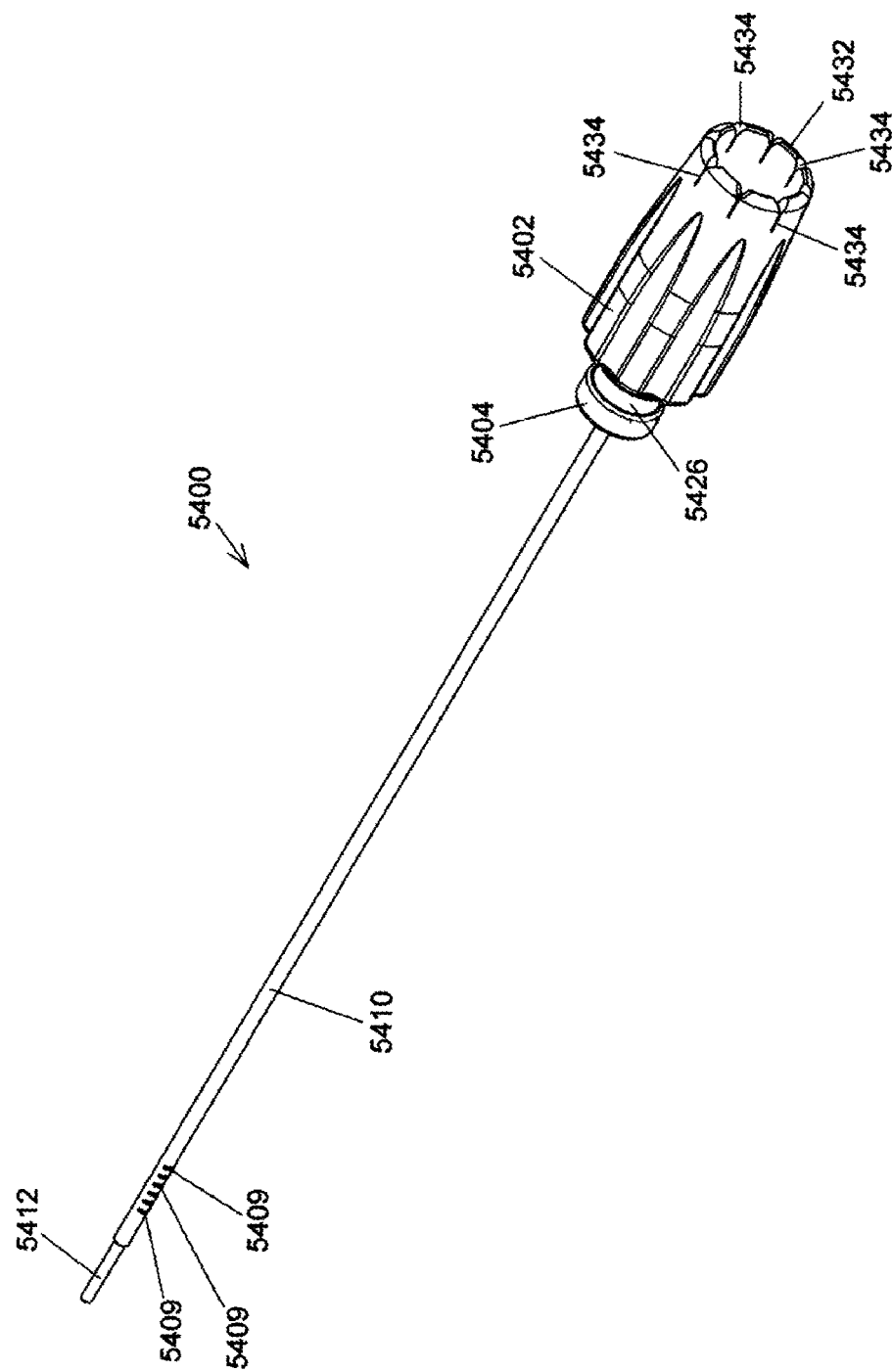
FIG. 83 is a perspective view of the objects of FIG. 80.

This need is addressed by the device depicted in FIGS. 90 to 94. Specifically, FIGS. 90 through 94 depict a tapping device 6000 having a distal thread-forming portion which may be angularly offset from the proximal torque-supplying portion of device 6000. Device 6000 is constructed like device 5000 except for the following aspects. Anchor 5600 is eliminated since device 6000 is a thread forming device. Distal drive element 5512 is replaced by thread-forming element 6010 having a coaxial cannulation 6012 through its length. Suture cleats 5434 have been eliminated from handle 5402 to form handle 6402. As best seen in FIG. 81, distal tubular element 5412 has been shortened to form distal tubular element 6412 which slidably engages coaxial cylindrical recess 6014 in the proximal end of thread-forming element 6010. As with device 5000, notches 6409 in inner tubular member 6410 locally reduce the flexural strength of tubular member 6410 so as to allow localized bending of member 6410 thereby imparting an angular offset to distal outer tubular member 6511 and thread-forming element 6010. Cannulation 6012 in thread-forming element 6010 allows device 6000 to be used with a guidewire, that is, with the location and alignment of thread-forming element 6010 established by a previously placed small diameter protruding wire element positioned at the hole location, the guide-wire engaging cannulation 6012 as thread-forming element 6010 is advanced distally to the hole.

Yet another alternate embodiment of the present invention is depicted in FIGS. 95 and 96. Device 7000 is a driver for screws used with plating systems, particularly in trauma surgery, typical of the screws being those by Acumed (Hillsboro, Oreg.). Device 7000 is identical to device 6000 in all aspects except that thread-forming element 6010 has been replaced by driving element 7030 with cannulation 7032 and distal drive portion 7034.

Figure 98:
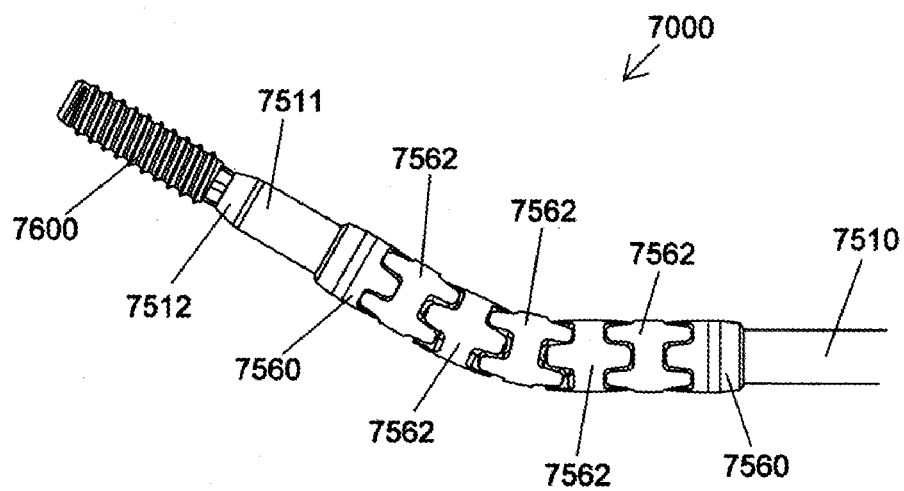
FIG. 98 is a side elevational view of the objects of FIG. 97.
Figure 100:
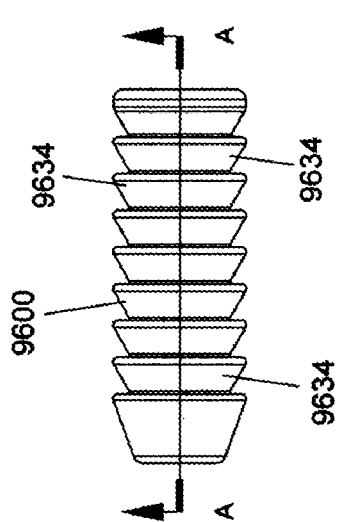
FIG. 100 is a plan view of the interference screw of FIG. 99.
Figure 102:
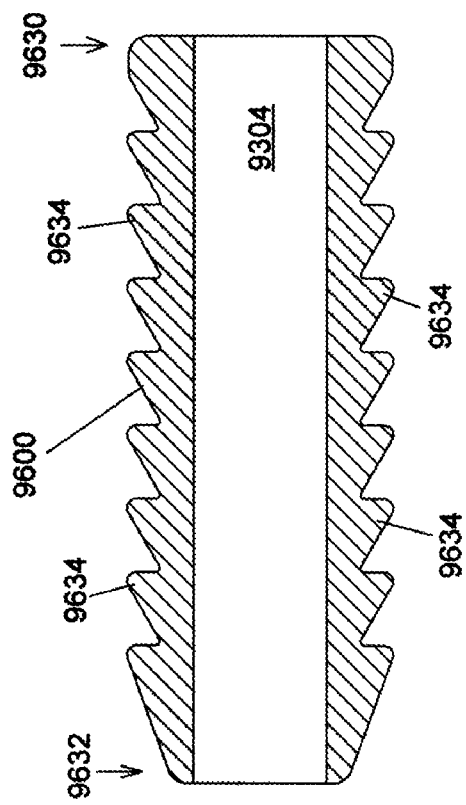
FIG. 102 is an expanded sectional view of the objects of FIG. 100 at location A-A.
Figure 99:
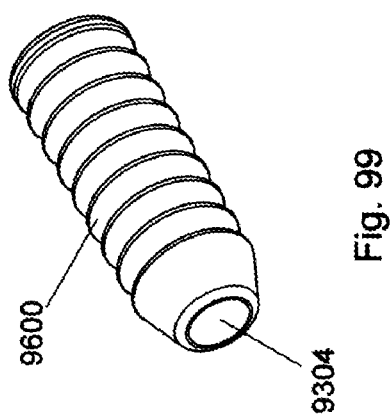
FIG. 99 is a distal perspective view of an alternate embodiment interference screw formed in accordance with the principles of the instant invention.
Figure 101:
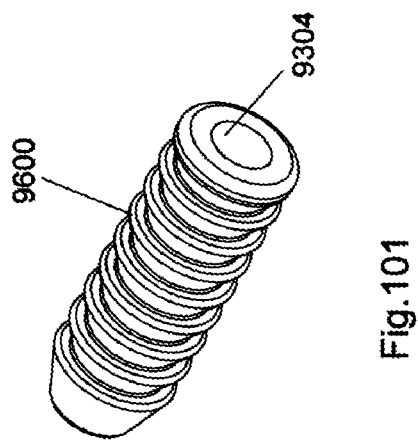
FIG. 101 is a proximal perspective view of the objects of FIG. 99.
Figure 104:
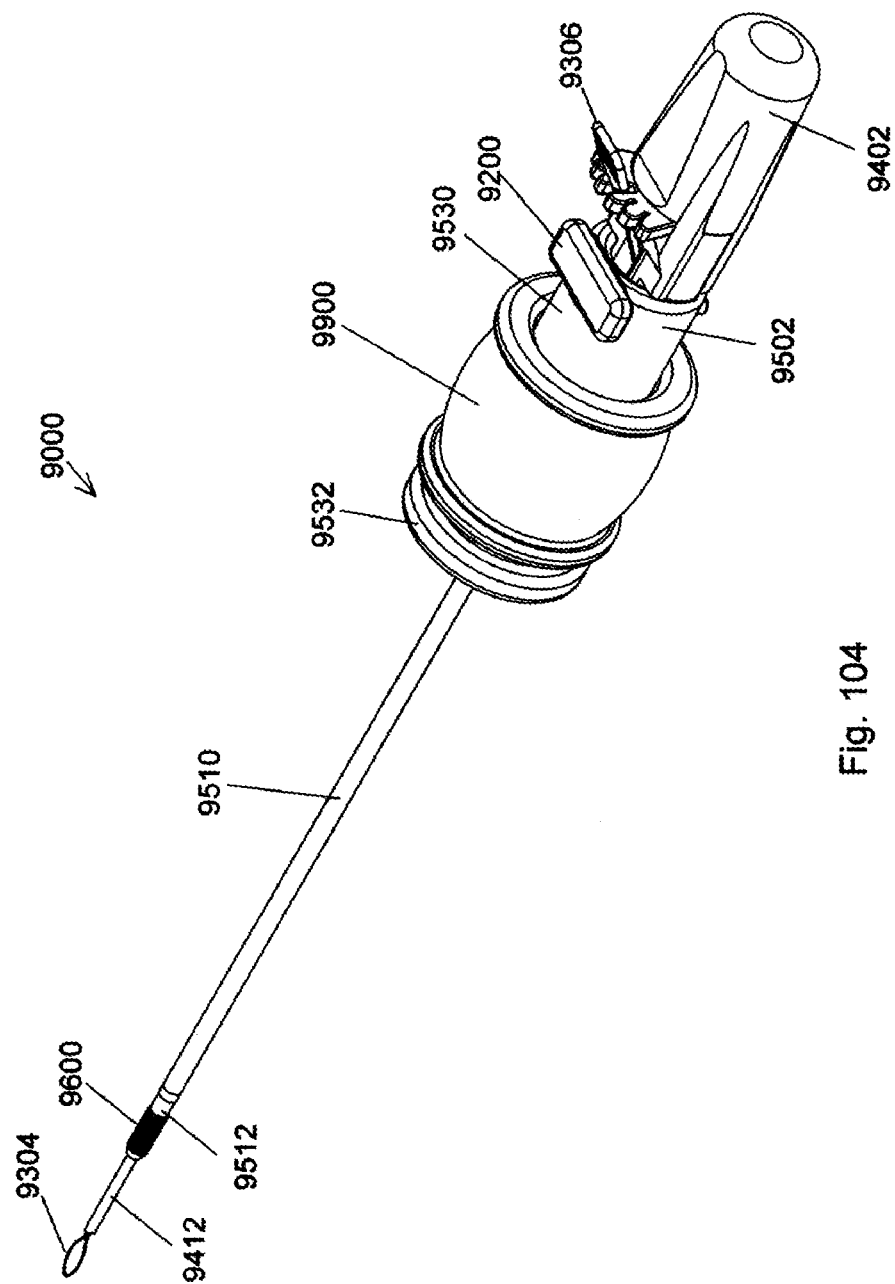
FIG. 104 is a perspective view of the alternate embodiment implant placement system of FIG. 103 with the elements assembled prior to use.
Figure 105:
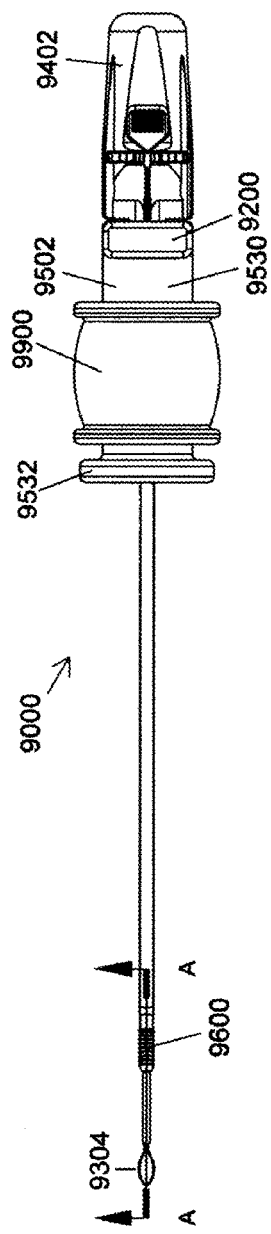
FIG. 105 is a plan view of the objects of FIG. 104.
Figure 106:
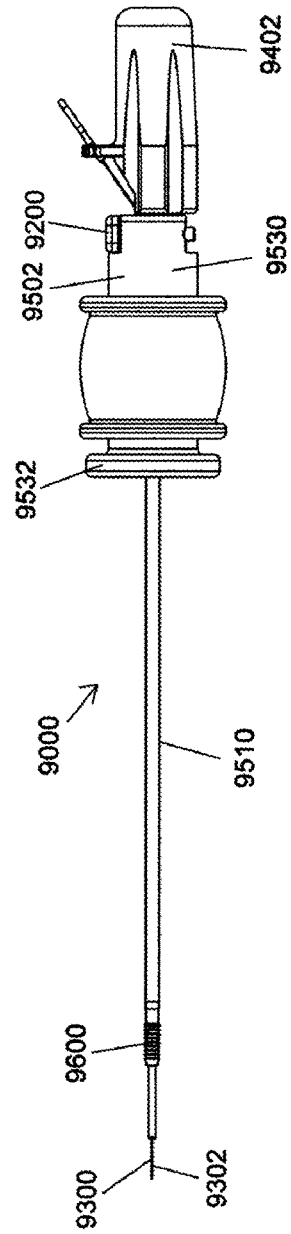
FIG. 106 is a side elevational view of the objects of FIG. 104.

FIGS. 98 and 99 depict an alternate distal portion construction of a driver system 7000 having a distal portion that is angularly offset from its proximal portion. Construction of the outer assembly is like that of driver system 5000 except outer assembly 7500 has replaced flexible element 5511 with discreet interlocking elements 7562 and coupling elements 7560 which link elements 7562 to outer tubular element 7510 an distal tubular element 7509 to as to transmit torque therebetween. The construction of system 7000 with its torque transmitting links 7562 may be advantageously applied to any embodiment of the instant invention in which the distal portion is angularly offset from the proximal portion and which requires enhanced torque transmitting capabilities. This may be particularly advantageous for off-axis placement of interference screws as previously taught in the system 6000 embodiment (FIGS. 46 through 61). Indeed, with enhanced torque transmission capabilities of the 9000 embodiment, the system 6000 interference screw system may be utilized in unique ligament replacement procedures which use large diameter interference screws and are not possible without devices in which the distal portion is angularly offset from the proximal portions.

In previous embodiments, the anchors are threaded and require transmission of torque to the anchor for installation. In certain instances it is preferable to place an anchor that is not threaded in but rather is pressed into the prepared socket. An anchor for axial insertion is depicted in FIGS. 99 through 102. Anchor 9600 has a proximal end 9630 and a distal end 9632 and has formed on its exterior surface ribs 9634 having a planar proximal surface and a conical distal surface. Lumen 9304 has no torsional drive features formed thereon.

Figure 107:
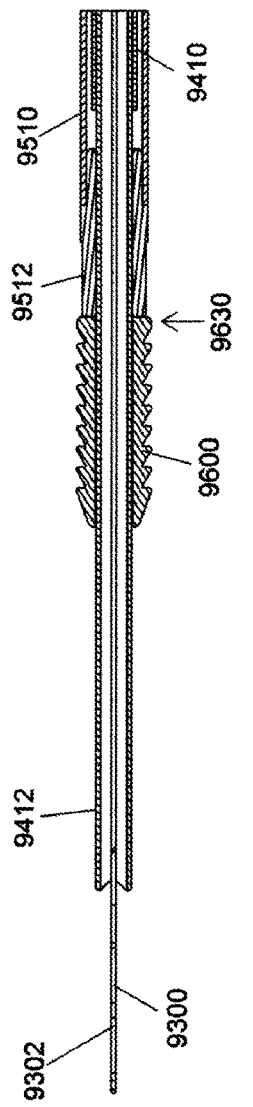
FIG. 107 is an expanded sectional view of the objects of FIG. 105 at location A-A.
Figure 108:
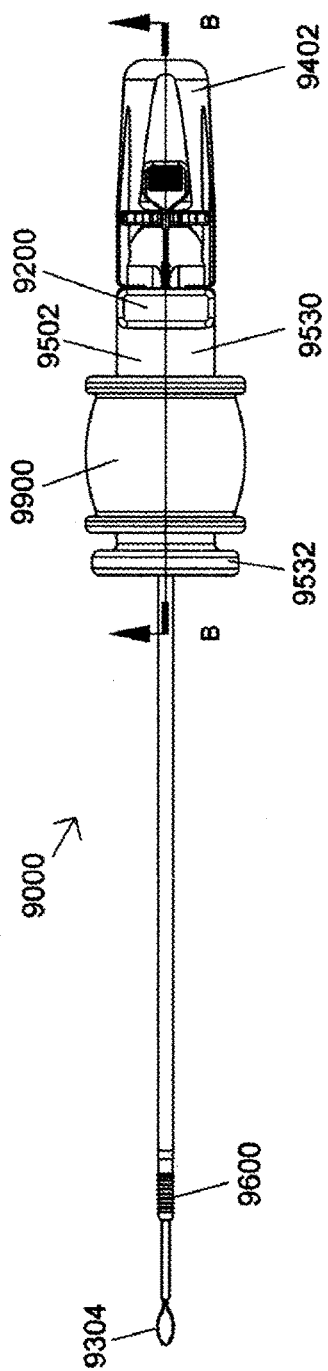
FIG. 108 is a plan view of the objects of FIG. 104.
Figure 109:
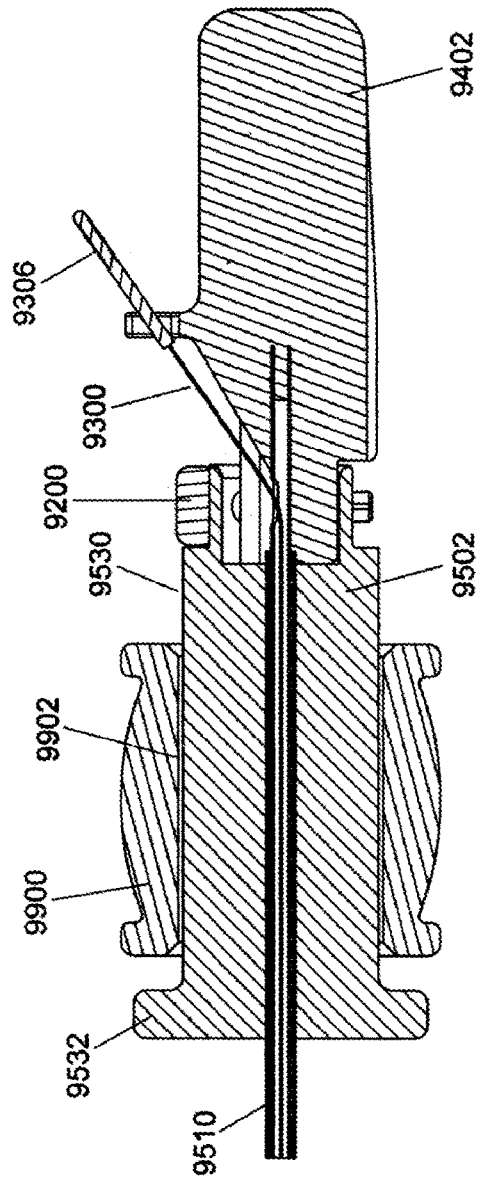
FIG. 109 is an expanded sectional view of the objects of FIG. 108 at location B-B.
Figure 110:
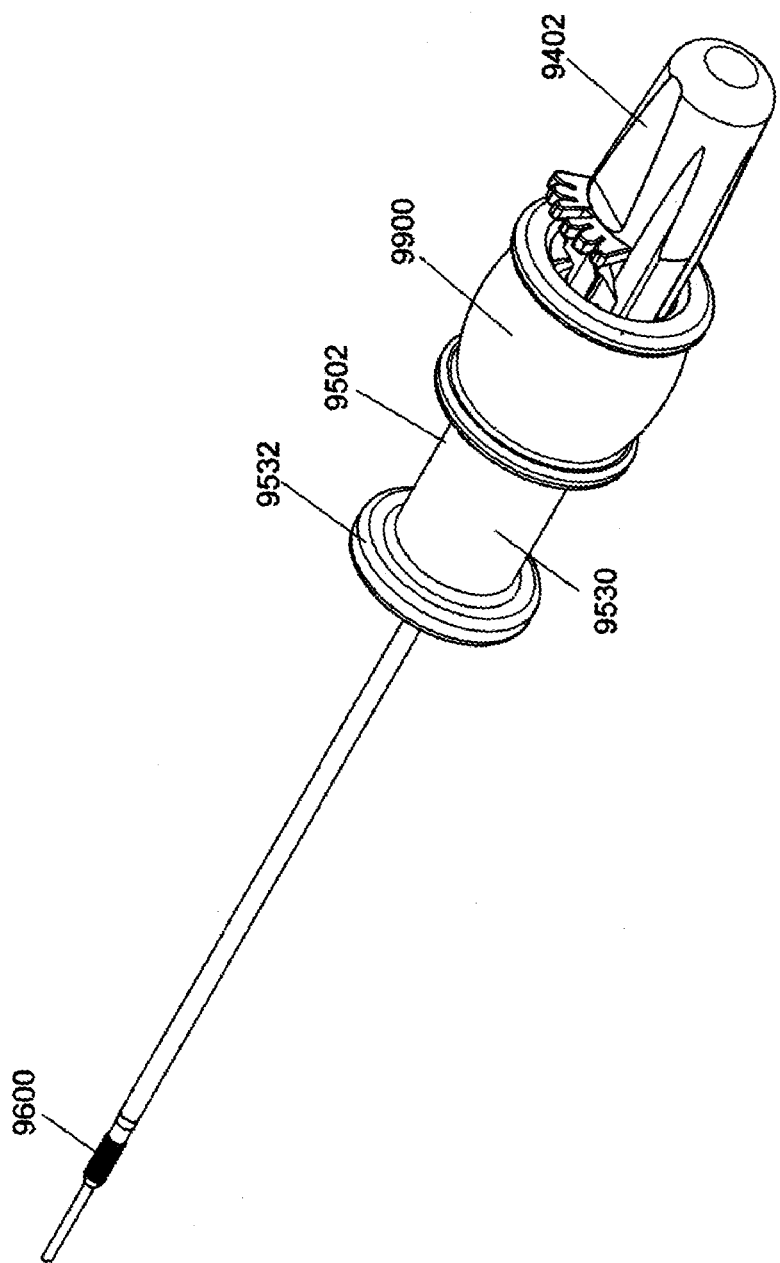
FIG. 110 is a perspective view of the alternate embodiment driver system of FIG. 104 with the slide in its proximal retracted position.
Figure 113:
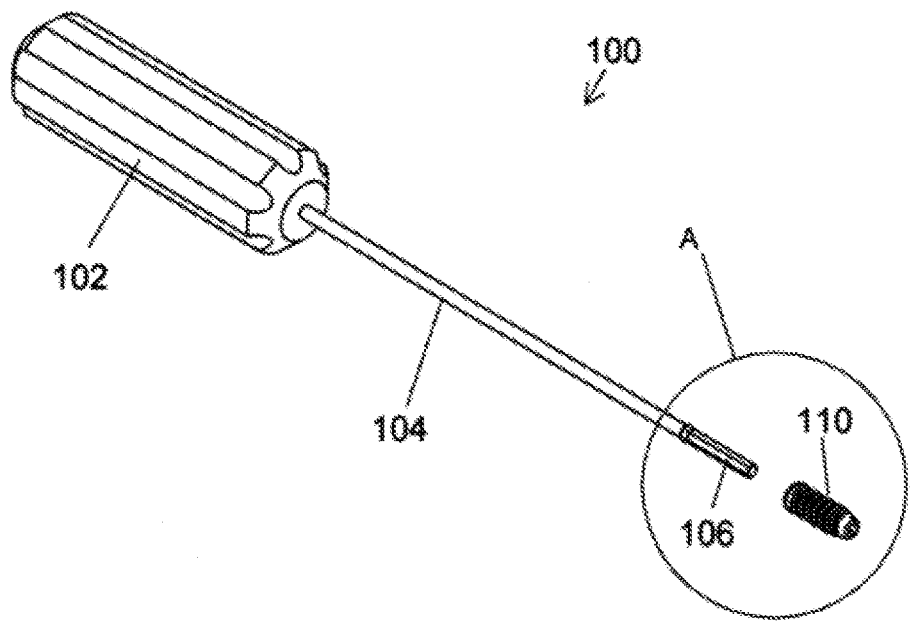
FIG. 113 is a perspective view of a prior art driver and anchor for placement therewith.
Figure 114:
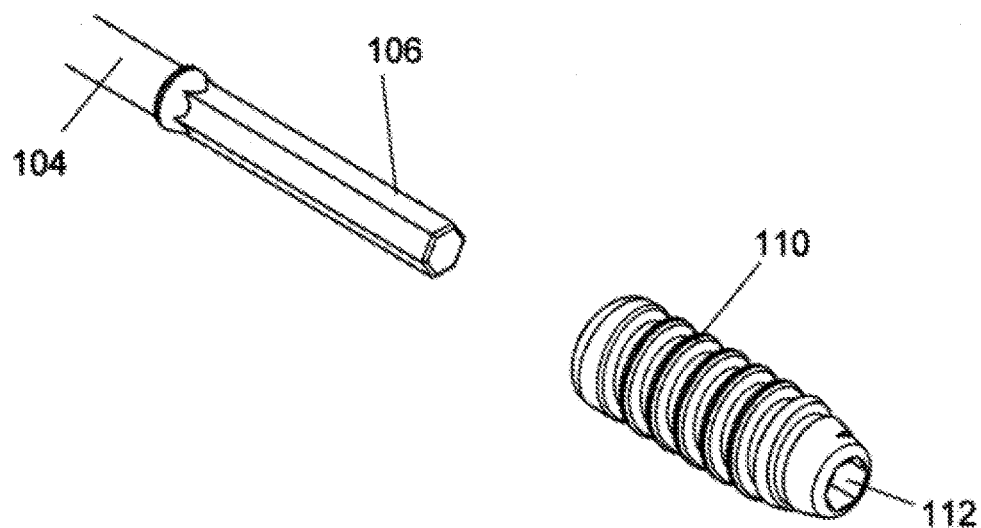
FIG. 114 is an expanded perspective view of the objects of FIG. 113 at location A.
Figure 115:
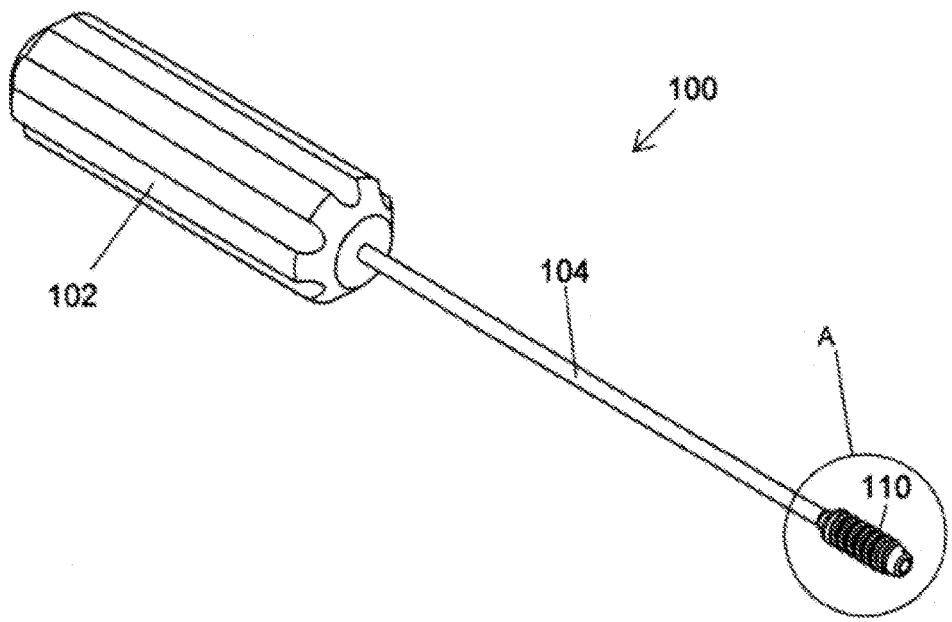
FIG. 115 is a perspective view of the prior art driver and anchor of FIG. 113 with the anchor mounted to the driver in preparation for use.
Figure 116:
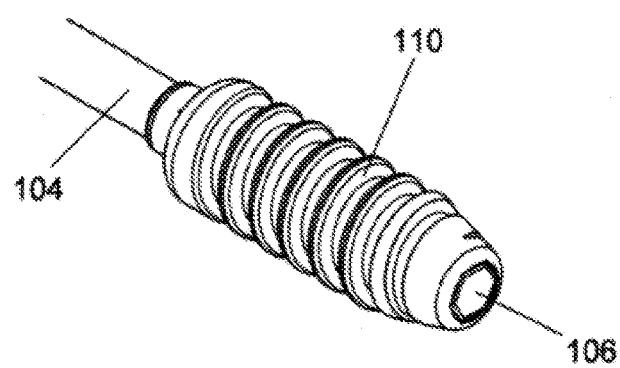

FIG. 103 depicts an anchor placement system 9000 for the placement of anchor 9600 in preparation for assembly for use. In all respects except as specifically indicated hereafter, system 9000 is identical in construction to system 3000 (FIGS. 35 through 45). System outer handle 9502 of outer assembly 9500 has a distal flange 9532 and a cylindrical surface 9530 proximal thereto. Slide 9900 with central lumen 9902 is coaxially assembled to outer handle 9502. FIGS. 104 through 109 depict placement system 9000 assembled for use with inner assembly 9400 assembled to outer assembly 9500 with slide 9900 assembled thereto. Key 9200 prevents axial and rotational motion of outer assembly 9500 with respect to inner assembly 9400 as previously herein described. As best seen in FIG. 107, distal drive element 9512 abuts proximal end 9630 of anchor 9600. Placement of anchor 9600 is accomplished in the same manner as anchor 1600 depicted in FIGS. 22 through 32 except that anchor 9600 is not threaded into the socket, but rather is "tapped in" by percussive force applied to proximal end 9630 of anchor 9600 without rotation. The percussive force is supplied by slide 9900 being retracted proximally as shown in FIGS. 110 through 113 and then moved distally so as to impact flange 9532 of outer handle 9502.

While insertion system 9000 uses slide 9900 to supply percussive force, in alternate embodiments slide 9900 is eliminated and percussive force is supplied by an external mallet to an aspect of external handle 9502 formed for that purpose.

INDUSTRIAL APPLICABILITY

As noted previously, there is a need in the art for simplified placement systems and methods for tissue graft anchors by which the surgeon may introduce one or more sutures into a prepared socket in the boney tissue, apply tension to the sutures to advance a soft tissue graft to a desired location, and then advance an anchor into the bone while maintaining suture tension. The present invention addresses this need by providing a system and method for the placement of an implant, especially a suture anchor, threaded, knotless or otherwise, that allows the surgeon to establish the graft position and, while maintaining that position, secure the anchor without changing the suture tension or causing a shift in the graft position and furthermore, when the anchor is threaded, without spinning of the suture. The present invention also provides off-axis socket drills and implant driving devices that enable implantation in remote and difficult to access boney surfaces using minimally invasive procedures. Although described in detail with respect to ligament repairs, such as repair of a torn rotator cuff, it will be readily apparent to the skilled artisan that the utility of the present invention extends to other tissues and injuries.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An implant placement system for affixing a soft tissue graft to a prepared socket in a boney surface via a rigid implant, said system comprising:

a. a cannulated, single-lumened driver device comprising a proximal handle portion and an elongate tubular distal portion that defines the longitudinal axis of the system, wherein said driver device has a distal end configured to receive said rigid implant and to transmit torque thereto, wherein said driver device further includes a flexible, torque-transmitting portion proximal to said distal portion; and b. a cannulated, single-lumened insertion device rotatably received within said single lumen of said driver device, said insertion device comprising a proximal hub portion having a proximal opening and an elongate tubular distal portion having a distal opening that is configured to receive first ends of one or more elongate sutures, whereby said one or more elongate sutures may be threaded through the single lumen of said insertion device and out said proximal opening, wherein, when said insertion device is rotatably positioned within said single lumen of said driver device, the distal portion of said insertion device is angularly offset from the longitudinal axis of said system such that said torque transmitting portion of said driver device is angularly offset from said system longitudinal axis.

2. The implant placement system of claim 1, wherein said distal portion of said insertion device includes a section in which the flexular yield strength is locally reduced.

3. The system of claim 2, wherein the locally reduced flexular yield strength of said section is due to the presence of one or more notches therein.

4. The system of claim 2, wherein the locally reduced flexular yield strength of said section is due to annealing of metallic material in said section.

5. The system of claim 1, wherein said system further comprises said rigid implant.

6. The system of claim 5, wherein said system includes comprises one or more elongate sutures.

7. The system of claim 6, wherein said sutures are preloaded into said rigid implant.

8. The system of claim 1, wherein said system includes one or more elongate sutures.

* * * * *